United States Patent [19]

Müller et al.

[11] Patent Number: 5,783,722
[45] Date of Patent: Jul. 21, 1998

[54] 2-[4-BIPHENYLOXYMETHYLENE] ANILIDES, PREPARATION THEREOF AND INTERMEDIATES THEREFOR, AND USE THEREOF

[75] Inventors: Bernd Müller, Frankenthal; Wassilios Grammenos, Ludwigshafen; Hubert Sauter, Mannheim; Franz Röhl, Schifferstadt; Eberhard Ammermann, Heppenheim; Gisela Lorenz, Hambach; Norbert Götz, Worms, all of Germany

[73] Assignee: BASF Aktiengesellschaft, Ludwigshafen, Germany

[21] Appl. No.: 836,547

[22] PCT Filed: Nov. 10, 1995

[86] PCT No.: PCT/EP95/04429

§ 371 Date: May 6, 1997

§ 102(e) Date: May 6, 1997

[87] PCT Pub. No.: WO96/16029

PCT Pub. Date: May 30, 1996

[30] Foreign Application Priority Data

Nov. 23, 1994 [DE] Germany ............ 44 41 673.3

[51] Int. Cl.⁶ .................. C07C 26/00; C07C 239/00
[52] U.S. Cl. .............................. 560/27; 560/313
[58] Field of Search ........................ 560/27, 313

[56] References Cited

FOREIGN PATENT DOCUMENTS 619301 12/1994 European Pat. Off. .

Primary Examiner—Paul J. Killos

[57] ABSTRACT

2-[4-Biphenyloxymethylene]anilides of the formula I

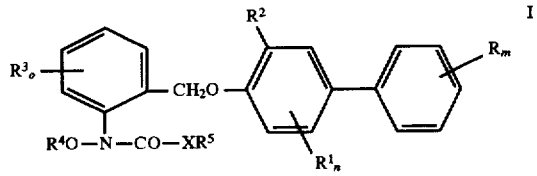

where the indices and the substituents have the following meanings:

R, R¹ and R² are cyano, nitro, halogen, alkyl, haloalkyl, alkoxy, haloalkoxy, alkylthio, haloalkylthio, alkylamino, dialkylamino, alkylcarbonyl, alkoxycarbonyl, alkylaminocarbonyl, dialkylaminocarbonyl, alkylcarbonylamino, alkylcarbonyl(alkylamino), alkenyl, alkenyloxy, alkynyl, alkynyloxy, cycloalkyl or C(R$^a$)=NOR$_b$;

R$^a$ and R$^b$ are hydrogen, alkyl, alkenyl, alkynyl, cycloalkyl or cycloalkenyl;

m is 1, 2, 3, 4 or 5;

n is 0, 1 or 2;

R³ is nitro, cyano, halogen, n is 0, 1 or 2,
  unsubst. or subst. alkyl, alkenyl, alkynyl, alkoxy, alkenyloxy, alkynyloxy or
  alkylcarbonyl, alkoxycarbonyl, alkylaminocarbonyl, dialkylaminocarbonyl, alkylcarbonylamino, alkylcarbonyl(alkylamino), C(R$^a$)=NOR$_b$or o is 0, 1, 2, 3 or 4;

R⁴ is hydrogen,
  unsubst. or subst. alkyl, alkenyl, alkynyl, cycloalkyl, cycloalkenyl, alkylcarbonyl or alkoxycarbonyl;

X is a direct bond or CH₂, O or NR$^c$;
  R$^c$ is hydrogen, alkyl, alkenyl, alkynyl, cycloalkyl or cycloalkenyl;

R⁵ is alkyl, alkenyl, alkynyl, cycloalkyl or cycloalkenyl, or or in the case where X is NR$^c$, is additionally hydrogen, processes and intermediates for their preparation, and their use are described.

12 Claims, No Drawings

2-[4-BIPHENYLOXYMETHYLENE] ANILIDES, PREPARATION THEREOF AND INTERMEDIATES THEREFOR, AND USE THEREOF

The present invention relates to 2-[4-biphenyloxymethylene]-anilides of the formula I

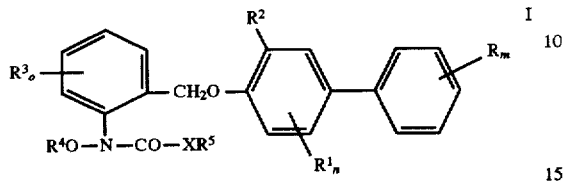

where the indices and the substituents have the following meanings:

R is cyano, nitro, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-halo-alkylthio, $C_1-C_4$-alkylamino, di-$C_1-C_4$-alkylamino, $C_1-C_4$-alkyl-carbonyl, $C_1-C_4$-alkoxycarbonyl, $C_1-C_4$-alkylaminocarbonyl, di($C_1-C_4$-alkyl)aminocarbonyl, $C_1-C_4$-alkylcarbonylamino, $C_1-C_4$-alkylcarbonyl($C_1-C_4$-alkylamino), $C_2-C_4$-alkenyl, $C_3-C_4$-alkenyloxy, $C_2-C_4$-alkynyl, $C_3-C_4$-alkynyloxy, $C_3-C_6$-cyclo-alkyl or $C(R^a)=NOR^b$;

$R^a$ and $R^b$ are hydrogen, alkyl, alkenyl, alkynyl, cycloalkyl or cycloalkenyl;

m is 1, 2, 3, 4 or 5, it being possible for the radicals R to be different if m is greater than 1;

$R^1$ is cyano, nitro, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-halo-alkylthio, $C_1-C_4$-alkylamino, di-$C_1-C_4$-alkylamino, $C_1-C_4$-alkyl-carbonyl, $C_1-C_4$-alkoxycarbonyl, $C_1-C_4$-alkylaminocarbonyl, di($C_1-C_4$-alkyl)aminocarbonyl, $C_1-C_4$-alkylcarbonylamino, $C_1-C_4$-alkylcarbonyl($C_1$ -$C_4$-alkylamino), $C_2-C_4$-alkenyl, $C_3-C_4$-alkenyloxy, $C_2-C_4$-alkynyl, $C_3-C_4$-alkynyloxy, $C_3-C_6$-cyclo-alkyl or $C(R^a)=NOR^b$;

n is 0, 1 or 2, it being possible for the radicals $R^1$ to be different if n is 2;

$R^2$ is cyano, nitro, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-halo- alkylthio, $C_1-C_4$-alkylamino, di-$C_1-C_4$-alkylamino, $C_1-C_4$-alkyl-carbonyl, $C_1-C_4$-alkoxycarbonyl, $C_1-C_4$-alkylaminocarbonyl, di($C_1-C_4$-alkyl)aminocarbonyl, $C_1-C_4$-alkylcarbonylamino, $C_1-C_4$-alkylcarbonyl($C_1-C_4$-alkylamino), $C_2-C_4$-alkenyl, $C_3-C_4$-alkenyloxy, $C_2-C_4$-alkynyl, $C_3-C_4$-alkynyloxy, $C_3-C_6$-cyclo-alkyl or $C(R^a)=NOR^b$;

$R^3$ is nitro, cyano, halogen,
unsubst. or subst. alkyl, alkenyl, alkynyl, alkoxy, alkenyloxy, alkynyloxy or
$C_1-C_4$-alkylcarbonyl, $C_1-C_4$-alkoxycarbonyl, $C_1-C_4$-alkylamino-carbonyl, di($C_1-C_4$-alkyl)aminocarbonyl, $C_1-C_4$-alkylcarbonyl-amino, $C_1-C_4$-alkylcarbonyl ($C_1-C_4$-alkylamino), $C(R^a)=NOR^b$ or in the case where o is greater than 1, is additionally an unsubst. or subst. bridge bonded to two adjacent ring atoms, which can carry three to four members from the group consisting of 3 or 4 carbon atoms, and 2 or 3 carbon atoms and 1 or 2 nitrogen, oxygen and/or sulfur atoms, it being possible for this bridge, together with the ring to which it is bonded, to form a partially unsaturated or aromatic radical;

o is 0, 1, 2, 3 or 4, it being possible for the substituents $R^3$ to be different if n is greater than 1;

$R^4$ is hydrogen,
unsubst. or subst. alkyl, alkenyl, alkynyl, cycloalkyl, cycloalkenyl, alkylcarbonyl or alkoxycarbonyl;

X is a direct bond or $CH_2$, O or $NR^c$;

$R^c$ is hydrogen, alkyl, alkenyl, alkynyl, cycloalkyl or cycloalkenyl;

$R^5$ is alkyl, alkenyl, alkynyl, cycloalkyl or cycloalkenyl, or or in the case where X is $NR^c$, is additionally hydrogen.

In addition, the invention relates to processes and intermediates for preparing these compounds, compositions containing them and their use for controlling animal pests or harmful fungi. WO-A 3/15,046 describes 2-[4-biphenyloxymethylene]anilides in general form for controlling animal pests and harmful fungi, the active compounds of this group described there carrying substituents either on one or the other phenyl ring of the biphenyl system. However, these compounds leave something to be desired in practice with respect to the control success or the application rates required.

It is an object of the present invention to provide compounds having improved properties.

We have found that this object is achieved by the compounds I defined at the outset. Processes and intermediates for their preparation, compositions containing them and their use for controlling animal pests or harmful fungi have additionally been found.

The compounds I are obtainable in various ways.

Those compounds I where $R^4$ is hydrogen and X is a direct bond or oxygen are obtained, for example, by converting a benzyl derivative of the formula II into the corresponding 2-[4-biphenyloxymethylene]nitrobenzene of the formula IV in the presence of a base using a 4-biphenol of the formula III, then reducing IV to the N-hydroxylaniline of the formula Va and converting Va into I using a carbonyl compound of the formula VI.

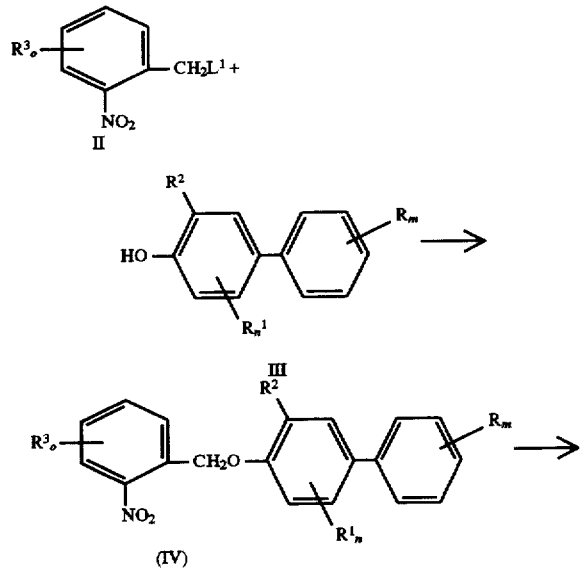

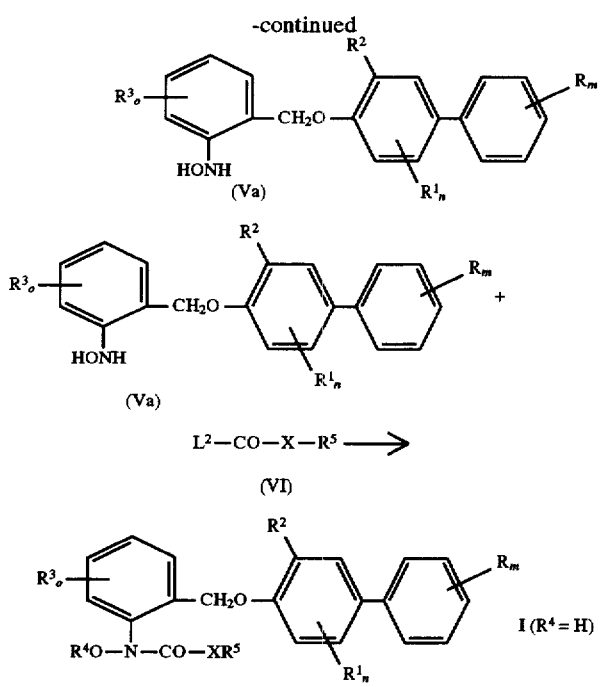

L¹ in the formula II and L² in the formula VI are each a nucleophilically replaceable group, for example halogen (eg. chlorine, bromine or iodine), or an alkyl- or arylsulfonate (eg. methanesulfonate, trifluoromethanesulfonate, benzenesulfonate or 4-toluenesulfonate).

The etherification of the compounds II and III is customarily carried out at from 0° C. to 80° C., preferably 20° C. to 60° C.

Suitable solvents are aromatic hydrocarbons such as toluene, o-,m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, i-propanol, n-butanol and tert-butanol, ketones such as acetone and methylethyl ketone and also dimethyl sulfoxide, dimethyl-formamide, dimethylacetamide, 1,3-dimethylimidazolidin-2-one and 1,2-dimethyltetrahydro-2(1H)-pyrimidine, preferably methylene chloride, acetone and dimethylformamide. Mixtures of the solvents mentioned can also be used.

Suitable bases are generally inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and also alkali metal hydrogen-carbonates (eg. sodium hydrogencarbonate), organometallic compounds, in particular alkali metal alkyls (eg. methyllithium, butyllithium and phenyllithium), alkylmagnesium halides (eg. methylmagnesium chloride) and also alkali metal and alkaline earth metal alkoxides (eg. sodium methoxide, sodium ethoxide, potassium ethoxide, potassium tert-butoxide and dimethoxymagnesium), additionally organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Sodium hydroxide, potassium carbonate and potassium tert-butoxide are particularly preferred.

The bases are in general used in an equimolar amount, in an excess or, if desired, as a solvent.

It may be advantageous for the reaction to add a catalytic amount of a crown ether (eg. 18-crown-6 or 15-crown-5).

The reaction can also be carried out in two-phase systems consisting of a solution of alkali metal or alkaline earth metal hydroxides or carbonates in water and an organic phase (eg. aromatic and/or halogenated hydrocarbons). Suitable phase-transfer catalysts here are, for example, ammonium halides and tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and also phosphonium halides (eg. tetrabutylphosphonium chloride and tetraphenylphosphonium bromide).

It may be advantageous for the reaction first to react the 4-hydroxybiphenyl III with the base to give the corresponding hydroxylate, which is then reacted with the benzyl derivative.

The starting substances II required for preparing the compounds I are disclosed in EP-A 513 580 and WO-A 93/15,046 or can be prepared by the methods described there.

4-Biphenols of the formula III are also known or can be obtained by known processes [cf. Synthesis 1993, 735; Synthesis 1992, 803; Synthesis 1992, 413; Pure and Appl. Chem. 66 (1994), 213; J. Org. Chem. 58 (1993), 2201; Tetrahedron 44 (1992), 9577; Chem. Rev. 93 (1993), 2117; Acc. Chem. Res. 15 (1982), 340; Pure and Appl. Chem. 52 (1980), 669 ].

The reduction of the nitro compounds IV to the corresponding N-hydroxyanilines Va is carried out in a similar manner to methods known from the literature, for example using metals such as zinc [cf. Ann. Chem. 316 (1901), 278] or using hydrogen (cf. EP-A 085 890).

The reaction of the N-hydroxyanilines Va with the carbonyl compounds VI is carried out under alkaline conditions conforming to the conditions described above for the reaction of the compounds II with the 4-biphenols III. The reaction is particularly preferably carried out at from −10° C. to 30° C. The preferred solvents are methylene chloride, toluene, tert-butyl methyl ether or ethyl acetate. The preferred bases are sodium hydrogencarbonate, potassium carbonate or aqueous sodium hydroxide solution.

The compounds of the formula I where X is a direct bond or oxygen are additionally obtained, for example, by reducing a benzyl derivative of the formula IIa first to the corresponding N-hydroxyaniline of the formula Vb, converting Vb into the corresponding anilide of the formula VII using a carbonyl compound of the formula VI, then converting VII into the amide of the formula IX using a compound VIII, then converting IX into the benzyl halide X and converting X into I in the presence of a base using a 4-biphenol of the formula III.

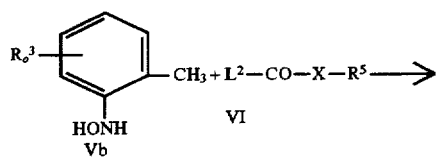

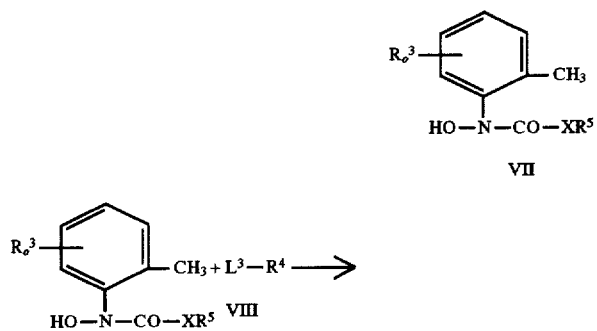

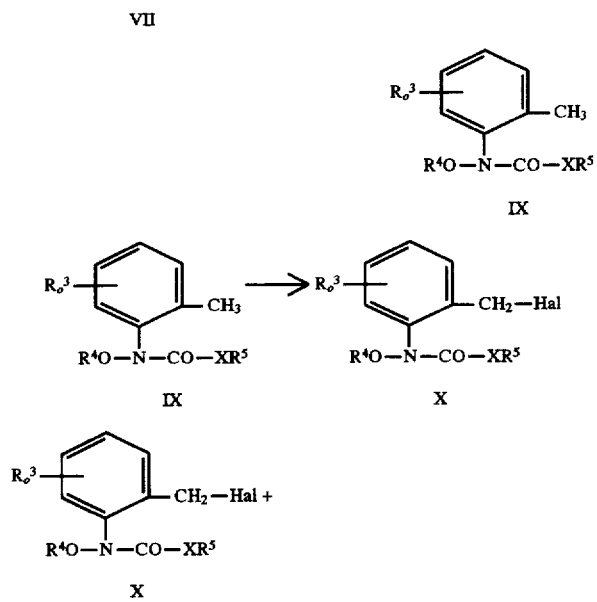

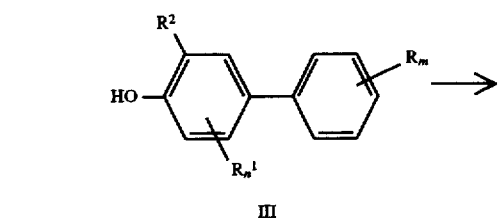

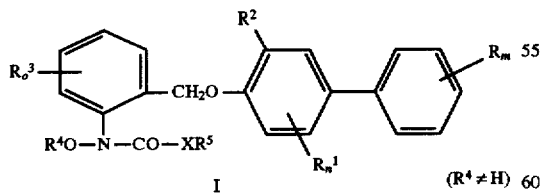

In the formula X, Hal is a halogen atom, in particular chlorine or bromine.

$L^3$ in the formula VIII is a nucleophilically replaceable group, for example halogen (eg.: chlorine, bromine or iodine), or an alkyl- or arylsulfonate (eg. methanesulfonate, trifluoro-methanesulfonate, benzenesulfonate or 4-toluenesulfonate) and $R^4$ is not hydrogen.

The reactions are carried out analogously to the processes explained above.

The halogenation of the compounds IX is carried out using free radicals, it being possible to employ as halogenating agents, for example, N-chloro- or N-bromosuccinimide, elemental halogens (eg. chlorine or bromine) or thionyl chloride, phosphorus trichloride or phosphorus pentachloride and similar compounds. Customarily, a free-radical initiator (eg. azobisisobutyronitrile) is additionally used or the reaction is carried out under irradiation (with UV light). The halogenation is carried out in a manner known per se in a customary organic diluent.

The compounds I where $R^4$ is not hydrogen are additionally obtained by reacting a corresponding compound of the formula I where $R^4$ is hydrogen with a compound of the formula VIII.

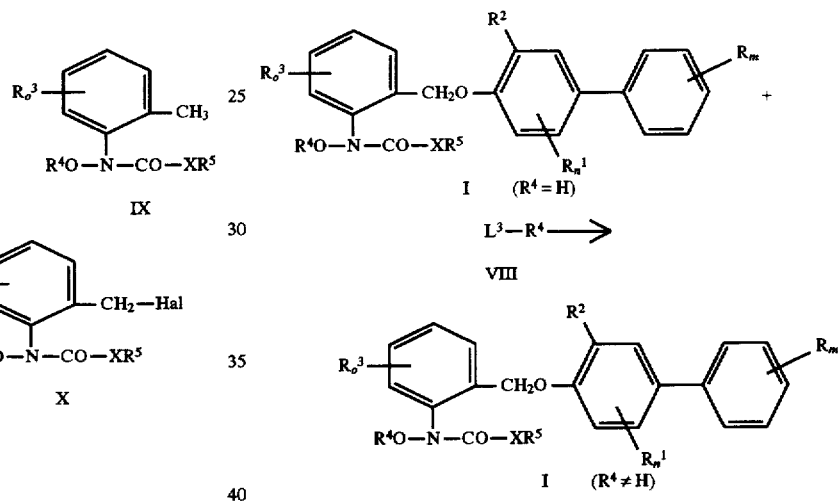

The reaction is carried out in a manner known per se in an inert organic solvent in the presence of a base at from 0° C. to 50° C.

The bases used are, in particular, sodium hydrogencarbonate, potassium carbonate, sodium hydroxide and aqueous sodium hydroxide solutions.

The solvents used are, in particular, acetone, dimethylformamide, toluene, tert-butyl methyl ether, ethyl acetate and methanol.

The compounds of the formula I where X is $NR^c$ are advantageously obtained by converting a benzanilide of the formula IXa into the corresponding benzyl halide of the formula Xa, converting Xa into a compound of the formula I.A in the presence of a base using a 4-biphenol of the formula III and then reacting I.A with an amine of the formula XI to give I.

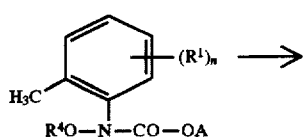

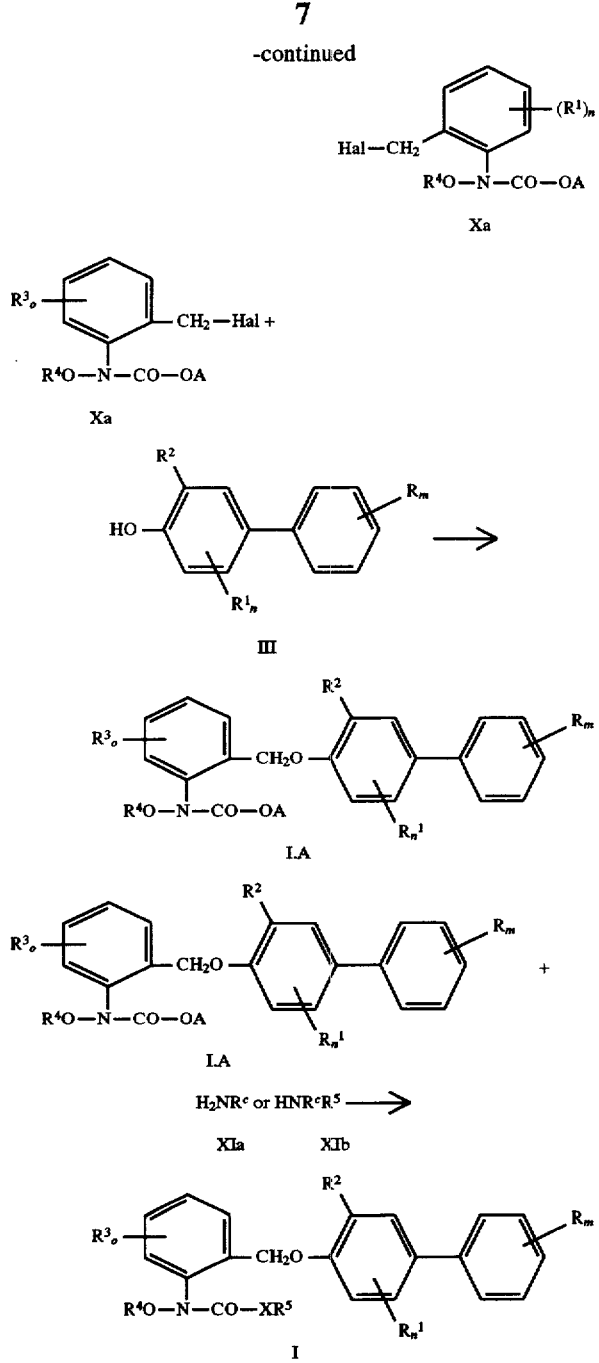

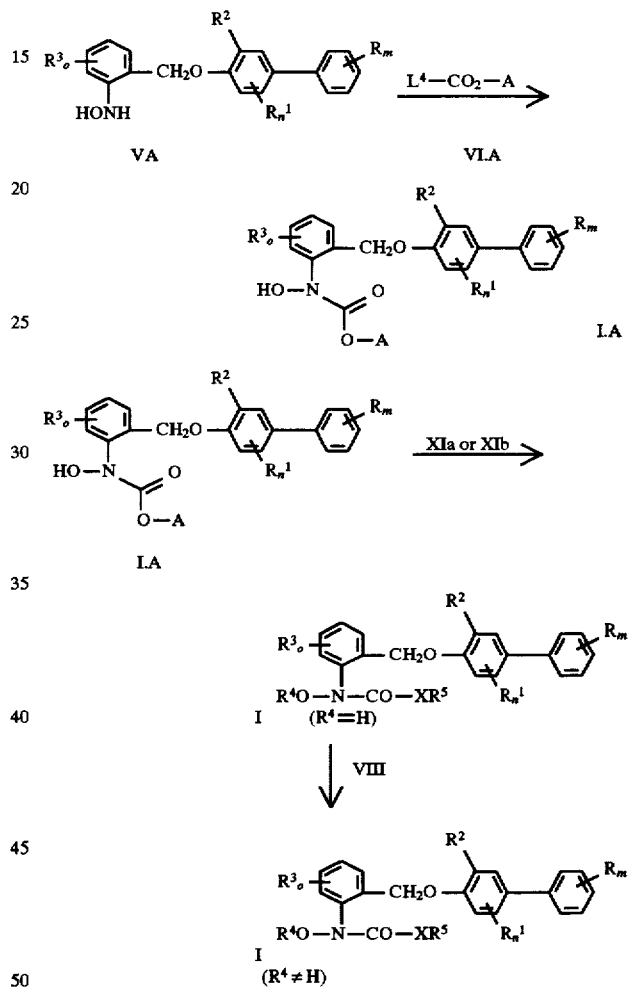

A in the formula IXa is alkyl (in particular $C_1$–$C_6$-alkyl) or phenyl; Hal in the formula Xa is halogen (in particular chlorine or bromine).

The reactions of IXa to Xa and of Xa to I.A are carried out in general and in particular under the conditions described above.

The reaction of the compounds I.A with the primary or secondary amines of the formula XIa or XIb is carried out at from 0° C. to 100° C. in an inert solvent or in a solvent mixture.

Suitable solvents are, in particular, water, tert-butyl methyl ether and toluene or mixtures thereof. It may be advantageous for improving the solubility of the starting materials additionally to add one of the following solvents (as solubilizer): tetrahydrofuran, methanol, dimethylformamide or ethylene glycol ether.

The amines XIa and XIb are customarily employed in an excess of up to 100% based on the compounds X or can be used as solvents. It may be advantageous with respect to the yield to carry out the reaction under pressure.

Amides of the formula I.A (A=phenyl) are obtained by reaction of the hydroxyanilines V.A with an acylating agent VI.A (A=phenyl).

The compound I.A can be reacted with an amine of the formula XIa or XIb to give the compound I ($R^4$=H, X=$NR^c$). Reaction of the compound I ($R^4$=H, X=$NR^c$) with an electrophile VIII gives the compounds I ($R^4 \neq H$, X=$NR^c$).

In addition, the compounds I are also obtained, for example, by reacting a compound XIV with an organometallic compound XV in the presence of a palladium catalyst.

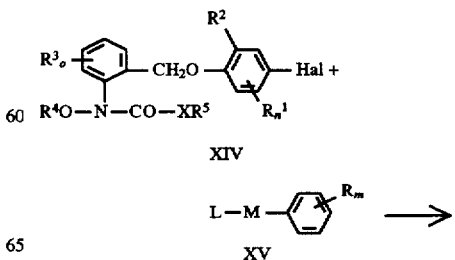

-continued

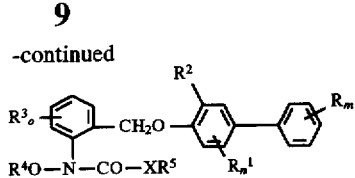

Hal in the formula XIV is a halogen atom (for example chlorine, bromine or iodine).

L-M in the formula XV is an organometallic radical such as a magnesium halide, or $B(OH)_2$ or trialkyltin.

The reaction conditions of the biphenyl synthesis correspond to the biphenyl syntheses known according to the literature [cf. Synthesis 1993, 735; Synthesis 1992, 803; Synthesis 1992, 413; Pure and Appl. Chem. 66 (1994), 213; J. Org. Chem. 58 (1993), 2201; Tetrahedron 44 (1992), 9577; Chem. Rev. 93 (1993), 2117; Acc. Chem. Res. 15 (1982), 340; Pure and Appl. Chem. 52 (1980), 669 ].

The compounds I are prepared analogously to the methods described in WO-A 93/15,046 via intermediates of the formula XII

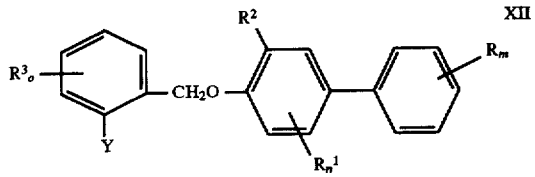

where Y is $NO_2$, NHOH, $NHOR^4$, $N(OH)-CO_2C_6H_5$ or $N(OR^4)-CO_2C_6H_5$ and the indices m, n and o and the substituents R, $R^1$, $R^2$, $R^3$ and $R^4$ have the meanings given in claim 1.

Additionally, the compounds I can be prepared via intermediates of the formula XII.A

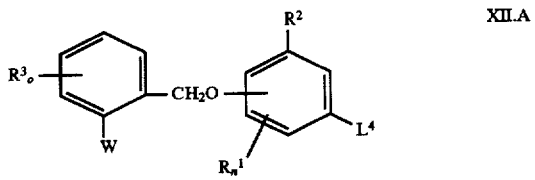

according to the methods of biaryl synthesis (for literature references see above), where W is $NO_2$, NHOH, $NHOR^4$, $N(OR^4)COXR^5$ or $N(oR^4)CO_2$ phenyl, $L^4$ is halogen (Cl, Br, I) or $O-SO_2-CF_3$ or an organometallic group, corresponding to the methods of the abovementioned biaryl syntheses and $R^1_n$, $R^2$, $R^3_o$, $R^4$, $R^5$ and X have the meanings mentioned in claim 1.

The compounds I can contain acidic or basic centers and accordingly form acid addition products or base addition products or salts.

Acids for acid addition products are, inter alia, mineral acids (eg. halohydric acids such as hydrochloric and hydrobromic acids, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin). Bases for base addition products are, inter alia, oxides, hydroxides, carbonates or hydrogencarbonates of alkali metals or alkaline earth metals (eg. potassium or sodium hydroxide or carbonate) or ammonium compounds (eg. ammonium hydroxide).

In the definitions of the symbols indicated in the above formulae, in some cases collective terms were used which are generally representative of the following substituents:

halogen: fluorine, chlorine, bromine and iodine;

alkyl: saturated, straight-chain or branched hydrocarbon radicals having 1 to 4 or 10 carbon atoms, eg. methyl, ethyl, propyl, 1-methylethyl, butyl, 1-methylpropyl, 2-methylpropyl and 1,1-dimethylethyl;

haloalkyl: straight-chain or branched alkyl groups having 1 to 4 carbon atoms (as mentioned above), it being possible in these groups for the hydrogen atoms to be replaced partially or completely by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkylcarbonyl: straight-chain or branched alkyl groups in particular having 1 to 10 carbon atoms (as mentioned above), which are bonded to the structure via a carbonyl group (-CO-);

alkoxy: straight-chain or branched alkyl groups, having 1 to 4 or 10 carbon atoms (as mentioned above), which are bonded to the structure via an oxygen atom (-O-);

alkoxycarbonyl: straight-chain or branched alkoxy groups, having 1 to 4 carbon atoms (as mentioned above), which are bonded to the structure via a carbonyl group (-CO-);

alkylthio: straight-chain or branched alkyl groups, having 1 to 4 carbon atoms (as mentioned above), which are bonded to the structure via a sulfur atom (-S-);

unsubst. or subst. alkyl: saturated, straight-chain or branched hydrocarbon radicals, in particular having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

unsubst. or subst. alkenyl: unsaturated, straight-chain or branched hydrocarbon radicals, in particular having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

unsubst. or subst. alkenyloxy: straight-chain or branched alkenyl groups, having 3 to 10 carbon atoms (as mentioned above), which are bonded to the structure via an oxygen atom (-O-);

alkynyl: straight-chain or branched hydrocarbon groups, in particular having 2 to 20 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

unsubst. or subst. alkynyloxy: straight-chain or branched alkynyl groups having 3 to 10 carbon atoms (as mentioned above), which are bonded to the structure via an oxygen atom (-O-);

unsubst. or subst. cycloalkyl: mono- or bicyclic hydrocarbon radicals having 3 to 10 carbon atoms, eg. $C_3$–$C_{10}$-(bi)cycloalkyl such as cyclopropyl, cyclobutyl, cyclopentyl, cyclohexyl, cycloheptyl, bornanyl, norbornanyl, dicyclohexyl, bicyclo[3.3.0]octyl, bicyclo[3.2.1]octyl, bicyclo[2.2.2]octyl or bicyclo[3.3.1]nonyl;

unsubst. or subst. cycloalkenyl: mono- or bicyclic hydrocarbon radicals having 5 to 10 carbon atoms and a double bond in any desired ring position, eg. $C_5$–$C_{10}$-(bi)cycloalkenyl such as cyclopentenyl, cyclohexenyl, cycloheptenyl, bornenyl, norbornenyl, dicyclohexenyl and bicyclo[3.3.0]octenyl;

an unsubst. or subst. bridge bonded to two adjacent ring atoms, which can carry three or four members from the group consisting of 3 or 4 carbon atoms, and 1 to 3 carbon atoms and 1 or 2 nitrogen, oxygen and/or sulfur atoms, it being possible for this bridge, together with the ring to which it is bonded, to form a partially unsaturated or aromatic radical: bridges which, with the ring to which they are bonded, form, for example, one of the following systems: quinolinyl, benzofuranyl and naphthyl;

an unsubst. or subst. saturated or mono- or diunsaturated ring which, in addition to carbon atoms, can contain one to three of the following heteroatoms as ring members: oxygen, sulfur and nitrogen, for example carbocycles such as cyclopropyl, cyclopentyl, cyclohexyl, cyclopent-2-enyl, cyclohex-2-enyl, 5- to 6-membered, saturated or unsaturated heterocycles, containing one to three nitrogen atoms and/or an oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl and morpholinyl;

or an unsubst. or subst. mono- or dinuclear aromatic ring system which, in addition to carbon atoms, can contain one to four 30 nitrogen atoms, or one or two nitrogen atoms and an oxygen or sulfur atom, or an oxygen or sulfur atom, as ring members, ie. aryl radicals such as phenyl and naphthyl, preferably phenyl or 1- or 2-naphthyl, and hetaryl radicals, for example 5-membered ring heteroaromatics containing one to three nitrogen atoms and/or an oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered ring heteroaromatics containing one to four nitrogen atoms and heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The addition of unsubst. or subst. in relation to alkyl, alkenyl and alkynyl groups is intended to express that these groups can be partially or completely halogenated (ie. the hydrogen atoms of these groups can be partially or completely replaced by identical or different halogen atoms as mentioned above (preferably fluorine, chlorine and bromine, in particular fluorine and chlorine) and/or can carry one to three, in particular one, of the following radicals:

$C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_2$–$C_6$-alkenyloxy, $C_2$–$C_6$-haloalkenyloxy, $C_2$–$C_6$-alkynyloxy, $C_2$–$C_6$-haloalkynyloxy, $C_3$–$C_6$-cycloalkyl, $C_3$–$C_6$-cycloalkyloxy, $C_3$–$C_6$-cycloalkenyl, $C_3$–$C_6$-cycloalkenyloxy, or an unsubst. or subst. mono- or binuclear aromatic ring system which, in addition to carbon atoms, can contain one to four nitrogen atoms or one or two nitrogen atoms and an oxygen or sulfur atom or an oxygen or sulfur atom as ring members (as mentioned above), which can be bonded to the substituents directly or via an oxygen atom (-O-), a sulfur atom (-S-) or an amino group (-NR$^a$-), ie. aryl radicals such as phenyl and naphthyl, preferably phenyl or 1- or 2-naphthyl, and hetaryl radicals, for example 5-membered ring heteroaromatics containing one to three nitrogen atoms and/or an oxygen or sulfur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered ring heteroaromatics containing one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The addition of unsubst. or subst. in relation to the cyclic (saturated, unsaturated or aromatic) groups is intended to express that these groups can be partially or completely halogenated (ie. the hydrogen atoms of these groups can be partially or completely replaced by identical or different halogen atoms such as mentioned above (preferably fluorine, chlorine and bromine, in particular fluorine and chlorine) and/or can carry one to three of the following radicals:

nitro;

cyano, thiocyanato;

alkyl, particularly $C_1$–$C_6$-alkyl as mentioned above, preferably methyl, ethyl, 1-methylethyl, 1,1-dimethylethyl, butyl, hexyl, in particular methyl and 1-methylethyl;

$C_1$–$C_4$-haloalkyl, as mentioned above, preferably trichloromethyl, difluoromethyl, trifluoromethyl, 2,2-difluoroethyl, 2,2,2-trifluoroethyl and pentafluoroethyl;

$C_1$–$C_4$-alkoxy, preferably methoxy, ethoxy, 1-methylethoxy and 1,1-dimethylethoxy, in particular methoxy;

$C_1$–$C_4$-haloalkoxy, particularly $C_1$–$C_2$-haloalkoxy, preferably difluoromethoxy, trifluoromethoxy and 2,2,2-trifluoroethoxy, in particular difluoromethoxy;

$C_1$–$C_4$-alkylthio, preferably methylthio and 1-methylethylthio, in particular methylthio;

$C_1$–$C_4$-alkylamino such as methylamino, ethylamino, propylamino, 1-methylethylamino, butylamino, 1-methylpropylamino, 2-methylpropylamino and 1,1-dimethylethylamino, preferably methylamino and 1,1-dimethylethylamino, in particular methylamino, di-$C_1$–$C_4$-alkylamino such as N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1 -methylethyl)- N-(1-methylpropyl)amino, N-(1-methylethyl)-N-(2-methylpropyl)-amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably N,N-dimethylamino and N,N-diethylamino, in particular N,N-dimethylamino;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxycarbonyl such as methoxycarbonyl, ethoxycarbonyl, 5 propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, pentyloxycarbonyl, 1-methylbutyloxycarbonyl, 2-methylbutyloxycarbonyl, 3-methylbutyloxycarbonyl, 2,2-dimethylpropyloxycarbonyl, 1-ethylpropyloxycarbonyl, hexyloxycarbonyl, 1,1-dimethylpropoxycarbonyl, 1,2-dimethylpropyloxycarbonyl, 1-methylpentyloxycarbonyl, 2-methylpentyloxycarbonyl, 3-methylpentyloxycarbonyl, 4-methylpentyloxycarbonyl, 1,1-dimethylbutyloxycarbonyl, 1,2-dimethylbutyloxycarbonyl, 1,3-dimethylbutyloxycarbonyl, 2,2-dimethylbutyloxycarbonyl, 2,3-dimethylbutyloxycarbonyl, 3,3-dimethylbutyloxycarbonyl, 1-ethylbutyloxycarbonyl, 2-ethylbutyloxycarbonyl, 1,1,2-trimethylpropyloxycarbonyl, 1,2,2-trimethylpropyloxycarbonyl, 1-ethyl-1-methylpropyloxycarbonyl and 1-ethyl-2-methylpropyloxycarbonyl, preferably methoxycarbonyl, ethoxycarbonyl and 1,1-dimethylethoxycarbonyl, in particular ethoxycarbonyl;

$C_1$–$C_6$-alkylaminocarbonyl such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylaminocarbonyl and ethylaminocarbonyl, in particular methylaminocarbonyl;

di-$C_1$–$C_6$-alkylaminocarbonyl, particularly di-$C_1$–$C_4$-alkylaminocarbonyl such as N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl)aminocarbonyl, preferably N,N-dimethylaminocarbonyl and N,N-diethylaminocarbonyl, in particular N,N-dimethylaminocarbonyl;

$C_1$–$C_6$-alkylcarboxyl such as -methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl(1-methylpropylcarboxyl and 1-ethyl-2-methylpropylcarboxyl, preferably methylcarboxyl, ethylcarboxyl and 1,1-dimethylethylcarbonyl, in particular methylcarboxyl and 1,1-dimethylethylcarboxyl;

$C_1$–$C_6$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl(1-methylpropylcarbonylamino and 1-ethyl-2-methylpropylcarbonylamino, preferably methylcarbonylamino and ethylcarbonylamino, in particular ethylcarbonylamino;

$C_3$–$C_7$-cycloalkyl such as cyclopropyl, cyclobutyl, cyclopentyl, cyclohexyl and cycloheptyl, preferably cyclopropyl, cyclopentyl and cyclohexyl, in particular cyclopropyl;

$C_3$–$C_7$-cycloalkoxy such as cyclopropoxy, cyclobutoxy, cyclopentoxy, cyclohexoxy and cycloheptoxy, preferably cyclopentoxy and cyclohexoxy, in particular cyclohexoxy;

$C_3$–$C_7$-cycloalkylthio such as cyclopropylthio, cyclobutylthio, cyclopentylthio, cyclohexylthio and cycloheptylthio, preferably cyclohexylthio;

$C_3$–$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino.

In addition to the abovementioned substituents, the mono- or binuclear aromatic or heteroaromatic systems can also carry a radical -CR'=NOR", where the radicals R' and R" are the following groups:

R' is hydrogen, cyano, alkyl (preferably $C_1$–$C_6$-alkyl, in particular $C_1$–$C_4$-alkyl), haloalkyl (preferably $C_1$–$C_4$-haloalkyl, in particular $C_1$–$C_2$-haloalkyl), alkenyl (preferably $C_2$–$C_6$-alkenyl, in particular $C_2$–$C_4$-alkenyl), haloalkenyl (preferably $C_2$–$C_6$-haloalkenyl, in particular $C_2$–$C_4$-haloalkenyl), alkynyl (preferably $C_2$–$C_6$-alkynyl, in particular $C_2$–$C_4$-alkynyl), haloalkynyl (preferably $C_2$–$C_6$-haloalkynyl, in particular $C_2$–$C4$-haloalkynyl) and cycloalkyl (preferably $C_3$–$C_8$-cycloalkyl, in particular $C_3$–$C_6$-cycloalkyl);

R" is alkyl (preferably $C_1$–$C_6$-alkyl, in particular $C_1$–$C_4$-alkyl), haloalkyl (preferably $C_1$–$C_4$-haloalkyl, in particular $C_1$–$C_2$-haloalkyl), alkenyl (preferably $C_2$–$C_6$-alkenyl, in particular $C_2$–$C_4$-alkenyl), haloalkenyl (preferably $C_2$–$C_6$-haloalkenyl, in particular $C_2$–$C_4$-haloalkenyl), alkynyl (preferably $C_2$–$C_6$-alkynyl, in particular $C_2$–$C_4$-alkynyl), haloalkynyl (preferably $C_2$–$C_6$-haloalkynyl, in particular $C_2$–$C_4$-haloalkynyl) and cycloalkyl (preferably $C_3$–$C_8$-cycloalkyl, in particular C3–$C_6$-cycloalkyl).

With respect to their biological action, compounds I are preferred where R is $C_1$–$C_4$-alkyl.

In addition, compounds I are preferred where R is halogen, in particular fluorine, chlorine and bromine.

Equally, compounds I are preferred where R is $C_1$–$C_4$-alkoxy.

Additionally, compounds I are preferred where R is cyano or nitro.

Equally, compounds I are preferred where R is $C_1$–$C_4$-haloalkyl (in particular trifluoromethyl) or $C_1$–$C_4$-haloalkoxy (in particular trifluoromethoxy).

Additionally, compounds I are preferred where R is a group C($R^a$)=NO$R^b$, where $R^a$ and $R^b$ in particular represent $C_1$–$C_4$-alkyl groups.

In addition, compounds I are preferred where m is 1, 2 or 3, in particular 1 or 2.

In addition, compounds I are preferred where $R^1$ is $C_1$–$C_4$-alkyl or $C_1$–$C_4$-haloalkyl.

In addition, compounds I are preferred where $R^1$ is halogen (in particular fluorine, chlorine or bromine).

Equally, compounds I are preferred where $R^1$ is cyano or nitro.

Additionally, compounds I are preferred where $R^1$ is $C_1$–$C_4$-alkoxy or $C_1$–$C_4$-haloalkoxy.

In addition, compounds I are preferred where n is 0, 1 or 2 (in particular 0 or 1).

In addition, compounds I are preferred where $R^2$ is $C_1$–$C_4$-alkyl or $C_1$–$C_4$-haloalkyl.

In addition, compounds I are preferred where $R^2$ is halogen (in particular fluorine, chlorine or bromine).

Equally, compounds I are preferred where $R^2$ is cyano or nitro.

Additionally, compounds I are preferred where $R^2$ is $C_1$–$C_4$-alkoxy or $C_1$–$C_4$-haloalkoxy.

In addition compounds I are preferred where $R^3$ is cyano, halogen, $C_1$–$C_4$-alkyl, $C_1$–$C_2$-haloalkyl, $C_1$–$C_4$-alkoxy or $C_1$–$C_2$-haloalkoxy.

Equally, compounds I are preferred where o is 0 or 1,in particular 0.

In the case where o is not 0, compounds I are preferred where there is a radical $R^3$ in the 3- or 6-position.

In addition, compounds I are preferred where $R^4$ is hydrogen, $C_1$–$C_4$-alkyl or $C_1$–$C_2$-haloalkyl.

Additionally, compounds I are preferred where $R^5X$ is methyl, ethyl, methoxy or methylamino.

In particular, with respect to their use, the compounds I compiled in the following tables are preferred. The groups mentioned for a substituent in the tables are additionally considered per se (independently of the combination in which they are mentioned) to be a particularly preferred embodiment of the substituents concerned.

Table 1

Compounds of the general formula I (o=0), where $R^4$ is methyl, $R^5X$ is hydrogen and the combination of the substituents $R_m$, $R^1_n$ and $R^2$ for a compound in each case corresponds to one line of Table A.

Table 2

Compounds of the general formula I (o=0), where $R^4$ is methyl, $R^5X$ is methyl and the combination of the substituents $R_m$, $R^1_n$ and $R^2$ for a compound in each case corresponds to one line of Table A.

Table 3

Compounds of the general formula I (o=0), where $R^4$ is methyl, $R^5X$ is ethyl and the combination of the substituents $R_m$, $R^1_n$ and $R^2$ for a compound in each case corresponds to one line of Table A.

Table 4

Compounds of the general formula I (o=0), where $R^4$ is methyl, $R^5X$ is methoxy and the combination of the substituents $R_m$, $R^1_n$ and $R^2$ for a compound in each case corresponds to one line of Table A.

Table 5

Compounds of the general formula I (o=0), where $R^4$ is methyl, $R^5X$ is methylamino and the combination of the substituents $R_m$, $R^1_n$ and $R^2$ for a compound in each case corresponds to one line of Table A.

Table 6

Compounds of the general formula I (o=0), where $R^4$ is ethyl, $R^5X$ is hydrogen and the combination of the substituents $R_m$, $R^1_n$ and $R^2$ for a compound in each case corresponds to one line of Table A.

Table 7

Compounds of the general formula I (o=0), where $R^4$ is ethyl, $R^5X$ is methyl and the combination of the substituents $R_m$, $R^1$ and $R^2$ for a compound in each case corresponds to one line of Table A.

Table 8

Compounds of the general formula I (o=0), where $R^4$ is ethyl, $R^5X$ is ethyl and the combination of the substituents $R_m$, $R^1_n$ and $R^2$ for a compound in each case corresponds to one line of Table A.

Table 9

Compounds of the general formula I (o=0), where $R^4$ is ethyl, $R^5X$ is methoxy and the combination of the substituents $R_m$, $R^1_n$ and $R^2$ for a compound in each case corresponds to one line of Table A.

Table 10

Compounds of the general formula I (o=0), where $R^4$ is ethyl, $R^5X$ is methylamino and the combination of the substituents $R_m$, $R^1_n$ and $R^2$ for a compound in each case corresponds to one line of Table A.

Table 11

Compounds of the general formula I (o=1), where $R^3$ is 3-fluorine, $R^4$ is methyl, $R^5X$ is hydrogen and the combination of the substituents $R_m$, $R^1_n$ and $R^2$ for a compound in each case corresponds to one line of Table A.

Table 12

Compounds of the general formula I (o=1), where $R^3$ is 3-fluorine, $R^4$ is methyl, $R^5X$ is methyl and the combination of the substituents $R_m$, $R^1_n$ and $R^2$ for a compound in each case corresponds to one line of Table A.

Table 13

Compounds of the general formula I (o=1), where $R^3$ is 3-fluorine, $R^4$ is methyl, $R^5X$ is ethyl and the combination of the substituents $R_m$, $R^1_n$ and $R^2$ for a compound in each case corresponds to one line of Table A.

Table 14

Compounds of the general formula I (o=1), where $R^3$ is 3-fluorine, $R^4$ is methyl, $R^5X$ is methoxy and the combination of the substituents $R_m$, $R^1_n$ and $R^2$ for a compound in each case corresponds to one line of Table A.

Table 15

Compounds of the general formula I (o=1), where $R^3$ is 3-fluorine, $R^4$ is methyl, $R^5X$ is methylamino and the combination of the substituents $R_m$, $R^1_n$ and $R^2$ for a compound in each case corresponds to one line of Table A.

Table 16

Compounds of the general formula I (o=1), where $R^3$ is 3-chlorine, $R^4$ is methyl, $R^5X$ is hydrogen and the combination of the substituents $R_m$, $R^1_n$ and $R^2$ for a compound in each case corresponds to one line of Table A.

Table 17

Compounds of the general formula I (o=1), where $R^3$ is 3-chlorine, $R^4$ is methyl, $R^5X$ is methyl and the combination of the substituents $R_m$, $R^1_n$ and $R^2$ for a compound in each case corresponds to one line of Table A.

Table 18

Compounds of the general formula I (o=1), where $R^3$ is 3-chlorine, $R^4$ is methyl, $R^5X$ is ethyl and the combination of the substituents $R_m$, $R^1_n$ and $R^2$ for a compound in each case corresponds to one line of Table A.

Table 19

Compounds of the general formula I (o=1), where $R^3$ is 3chlorine, $R^4$ is methyl, $R^5X$ is methoxy and the combination of the substituents $R_m$, $R^1_n$ and $R^2$ for a compound in each case corresponds to one line of Table A.

Table 20

Compounds of the general formula I (o=1), where $R^3$ is 3-chlorine, $R^4$ is methyl, $R^5X$ is methylamino and the combination of the substituents $R_m$, $R^1_n$ and $R^2$ for a compound in each case corresponds to one line of Table A.

Table 21

Compounds of the general formula I (o=1), where $R^3$ is 6-chlorine, $R^4$ is methyl, $R^5X$ is hydrogen and the combination of the substituents $R_m$, $R^1_n$ and $R^2$ for a compound in each case corresponds to one line of Table A.

Table 22

Compounds of the general formula I (o=1), where $R^3$ is 6-chlorine, $R^4$ is methyl, $R^5X$ is methyl and the combination of the substituents $R_m$, $R^1_n$ and $R^2$ for a compound in each case corresponds to one line of Table A.

Table 23

Compounds of the general formula I (o=1), where $R^3$ is 6-chlorine, $R^4$ is methyl, $R^5X$ is ethyl and the combination of the substituents $R_m$, $R^1_n$ and $R^2$ for a compound in each case corresponds to one line of Table A.

Table 24

Compounds of the general formula I (o=1), where $R^3$ is 6-chlorine, $R^4$ is methyl, $R^5X$ is methoxy and the combination of the substituents $R_m$, $R^1_n$ and $R^2$ for a compound in each case corresponds to one line of Table A.

Table 25

Compounds of the general formula I (o=1), where $R^3$ is 6-chlorine, $R^4$ is methyl, $R^5X$ is methylamino and the combination of the substituents $R_m$, $R^1_n$ and $R^2$ for a compound in each case corresponds to one line of Table A.

Table 26

Compounds of the general formula I (o=0), where $R^4$ is hydrogen, $R^5X$ is hydrogen and the combination of the substituents $R_m$, $R^1_n$ and $R^2$ for a compound in each case corresponds to one line of Table A.

Table 27

Compounds of the general formula I (o=0), where $R^4$ is hydrogen, $R^5X$ is methyl and the combination of the substituents $R_m$, $R^1_n$ and $R^2$ for a compound in each case corresponds to one line of Table A.

Table 28

Compounds of the general formula I (o=0), where $R^4$ is hydrogen, $R^5X$ is ethyl and the combination of the substituents $R_m$, $R^1_n$ and $R^2$ for a compound in each case corresponds to one line of Table A.

Table 29

Compounds of the general formula I (o=0), where $R^4$ is hydrogen, $R^5X$ is methoxy and the combination of the substituents $R_m$, $R^1_n$ and $R^2$ for a compound in each case corresponds to one line of Table A.

Table 30

Compounds of the general formula I (o=0), where $R^4$ is hydrogen, $R^5X$ is methylamino and the combination of the substituents $R_m$, $R^1_n$ and $R^2$ for a compound in each case corresponds to one line of Table A.

Table 31

Compounds of the general formula I (o=1), where $R^3$ is 6-methyl, $R^4$ is methyl, $R^5X$ is hydrogen and the combination of the substituents $R_m$, $R^1_n$ and $R^2$ for a compound in each case corresponds to one line of Table A.

Table 32

Compounds of the general formula I (o=1), where $R^3$ is 6-methyl, $R^4$ is methyl, $R^5X$ is methyl and the combination of the substituents $R_m$, $R^1_n$ and $R^2$ for a compound in each case corresponds to one line of Table A.

Table 33

Compounds of the general formula I (o=1), where $R^3$ is 6-methyl, $R^4$ is methyl, $R^5X$ is ethyl and the combination of the substituents $R_m$, $R^1_n$ and $R^2$ for a compound in each case corresponds to one line of Table A.

Table 34

Compounds of the general formula I (o=1), where $R^3$ is 6-methyl, $R^4$ is methyl, $R^5X$ is methoxy and the combination of the substituents $R_m$, $R^1_n$ and $R^2$ for a compound in each case corresponds to one line of Table A.

Table 35

Compounds of the general formula I (o=1), where $R^3$ is 6-methyl, $R^4$ is methyl, $R^5X$ is methylamino and the combination of the substituents $R_m$, $R^1_n$ and $R^2$ for a compound in each case corresponds to one line of Table A.

Table 36

Compounds of the general formula I (o=1), where $R^3$ is 6-methyl, $R^4$ is hydrogen, $R^5X$ is hydrogen and the combination of the substituents $R_m$, $R^1_n$ and $R^2$ for a compound in each case corresponds to one line of Table A.

Table 37

Compounds of the general formula I (o=1), where $R^3$ is 6-methyl, $R^4$ is hydrogen, $R^5X$ is methyl and the combination of the substituents $R_m$, $R^1_n$ and $R^2$ for a compound in each case corresponds to one line of Table A.

Table 38

Compounds of the general formula I (o=1), where $R^3$ is 6-methyl, $R^4$ is hydrogen, $R^5X$ is ethyl and the combination of the substituents $R_m$, $R^1_n$ and $R^2$ for a compound in each case corresponds to one line of Table A.

Table 39

Compounds of the general formula I (o=1), where $R^3$ is 6-methyl, $R^4$ is hydrogen, $R^5X$ is methoxy and the combination of the substituents $R_m$, $R^1_n$ and $R^2$ for a compound in each case corresponds to one line of Table A.

Table 40

Compounds of the general formula I (o=1), where $R^3$ is 6-methyl, $R^4$ is hydrogen, $R^5X$ is methylamino and the combination of the substituents $R_m$, $R^1_n$ and $R^2$ for a compound in each case corresponds to one line of Table A.

Table 41

Compounds of the general formula I (o=1), where $R^3$ is 6-chlorine, $R^4$ is hydrogen, $R^5X$ is hydrogen and the combination of the substituents $R_m$, $R^1_n$ and $R^2$ for a compound in each case corresponds to one line of Table A.

Table 42

Compounds of the general formula I (o=1), where $R^3$ is 6-chlorine, $R^4$ is hydrogen, $R^5X$ is methyl and the combination of the substituents $R_m$, $R^1_n$ and $R^2$ for a compound in each case corresponds to one line of Table A.

Table 43

Compounds of the general formula I (o=1), where $R^3$ is 6-chlorine, $R^4$ is hydrogen, $R^5X$ is ethyl and the combination of the substituents $R_m$, $R^1_n$ and $R^2$ for a compound in each case corresponds to one line of Table A.

Table 44

Compounds of the general formula I (o=1), where $R^3$ is 6-chlorine, $R^4$ is hydrogen, $R^5X$ is methoxy and the combination of the substituents $R_m$, $R^1_n$ and $R^2$ for a compound in each case corresponds to one line of Table A.

Table 45

Compounds of the general formula I (o=1), where $R^3$ is 6-chlorine, $R^4$ is hydrogen, $R^5X$ is methylamino and the combination of the substituents $R_m$, $R^1_n$ and $R^2$ for a compound in each case corresponds to one line of Table A.

Table 46

Compounds of the general formula I (o=1), where $R^3$ is 3-chlorine, $R^4$ is hydrogen, $R^5X$ is hydrogen and the combination of the substituents $R_m$, $R^1_n$ and $R^2$ for a compound in each case corresponds to one line of Table A.

Table 47

Compounds of the general formula I (o=1), where $R^3$ is 3-chlorine, $R^4$ is hydrogen, $R^5X$ is methyl and the combination of the substituents $R_m$, $R^1_n$ and $R^2$ for a compound in each case corresponds to one line of Table A.

Table 48

Compounds of the general formula I (o=1), where $R^3$ is 3-chlorine, $R^4$ is hydrogen, $R^5X$ is ethyl and the combination of the substituents $R_m$, $R^1_n$ and $R^2$ for a compound in each case corresponds to one line of Table A.

Table 49

Compounds of the general formula I (o=1), where $R^3$ is 3-chlorine, $R^4$ is hydrogen, $R^5X$ is methoxy and the combination of the substituents $R_m$, $R^1_n$ and $R^2$ for a compound in each case corresponds to one line of Table A.

Table 50

Compounds of the general formula I (o=1), where $R^3$ is 3-chlorine, $R^4$ is hydrogen, $R^5X$ is methylamino and the combination of the substituents $R_m$, $R^1_n$ and $R^2$ for a compound in each case corresponds to one line of Table A.

Table 51

Compounds of the general formula I (o=1), where $R^3$ is 3-fluorine, $R^4$ is hydrogen, $R^5X$ is hydrogen and the combination of the substituents $R_m$, $R^1_n$ and $R^2$ for a compound in each case corresponds to one line of Table A.

Table 52

Compounds of the general formula I (o=1), where $R^3$ is 3-fluorine, $R^4$ is hydrogen, $R^5X$ is methyl and the combination of the substituents $R_m$, $R^1_n$ and $R^2$ for a compound in each case corresponds to one line of Table A.

Table 53

Compounds of the general formula I (o=1), where $R^3$ is 3-fluorine, $R^4$ is hydrogen, $R^5X$ is ethyl and the combination of the substituents $R_m$, $R^1_n$ and $R^2$ for a compound in each case corresponds to one line of Table A.

Table 54

Compounds of the general formula I (o=1), where $R^3$ is 3-fluorine, $R^4$ is hydrogen, $R^5X$ is methoxy and the combination of the substituents $R_m$, $R^1_n$ and $R^2$ for a compound in each case corresponds to one line of Table A.

Table 55

Compounds of the general formula I (o=1), where $R^3$ is 3-fluorine, $R^4$ is hydrogen, $R^5X$ is methylamino and the combination of the substituents $R_m$, $R^1_n$ and $R^2$ for a compound in each case corresponds to one line of Table A.

TABLE A

| Number | $R_m$ | $R^2$ | $R^1_n$ |
|---|---|---|---|
| 12 | 2-F | $CH_3$ | H |
| 13 | 3-F | $CH_3$ | H |
| 14 | 4-F | $CH_3$ | H |
| 15 | 2,4-$F_2$ | $CH_3$ | H |
| 16 | 2,4,6-$F_3$ | $CH_3$ | H |

TABLE A-continued

| Number | $R_m$ | $R^2$ | $R^1_n$ |
|---|---|---|---|
| 17 | 2,3,4,5,6-$F_5$ | $CH_3$ | H |
| 18 | 2,3-$F_2$ | $CH_3$ | H |
| 19 | 2-Cl | $CH_3$ | H |
| 20 | 3-Cl | $CH_3$ | H |
| 21 | 4-Cl | $CH_3$ | H |
| 22 | 2,3-$Cl_2$ | $CH_3$ | H |
| 23 | 2,4-$Cl_2$ | $CH_3$ | H |
| 24 | 2,5-$Cl_2$ | $CH_3$ | H |
| 25 | 2,6-$Cl_2$ | $CH_3$ | H |
| 26 | 3,4-$Cl_2$ | $CH_3$ | H |
| 27 | 3,5-$Cl_2$ | $CH_3$ | H |
| 28 | 2,3,4-$Cl_3$ | $CH_3$ | H |
| 29 | 2,3,5-$Cl_3$ | $CH_3$ | H |
| 30 | 2,3,6-$Cl_3$ | $CH_3$ | H |
| 31 | 2,4,5-$Cl_3$ | $CH_3$ | H |
| 32 | 2,4,6-$Cl_3$ | $CH_3$ | H |
| 33 | 3,4,5-$Cl_3$ | $CH_3$ | H |
| 34 | 2,3,4,6-$Cl_4$ | $CH_3$ | H |
| 35 | 2,3,5,6-$Cl_4$ | $CH_3$ | H |
| 36 | 2,3,4,5,6-$Cl_5$ | $CH_3$ | H |
| 37 | 2-Br | $CH_3$ | H |
| 38 | 3-Br | $CH_3$ | H |
| 39 | 4-Br | $CH_3$ | H |
| 40 | 2,4-$Br_2$ | $CH_3$ | H |
| 41 | 2,5-$Br_2$ | $CH_3$ | H |
| 42 | 2,6-$Br_2$ | $CH_3$ | H |
| 43 | 2,4,6-$Br_3$ | $CH_3$ | H |
| 44 | 2,3,4,5,6-$Br_5$ | $CH_3$ | H |
| 45 | 2-I | $CH_3$ | H |
| 46 | 3-I | $CH_3$ | H |
| 47 | 4-I | $CH_3$ | H |
| 48 | 2,4-$I_2$ | $CH_3$ | H |
| 49 | 2-Cl, 3-F | $CH_3$ | H |
| 50 | 2-Cl, 4-F | $CH_3$ | H |
| 51 | 2-Cl, 5-F | $CH_3$ | H |
| 52 | 2-Cl, 6-F | $CH_3$ | H |
| 53 | 2-Cl, 3-Br | $CH_3$ | H |
| 54 | 2-Cl, 4-Br | $CH_3$ | H |
| 55 | 2-Cl, 5-Br | $CH_3$ | H |
| 56 | 2-Cl, 6-Br | $CH_3$ | H |
| 57 | 2-Br, 3-Cl | $CH_3$ | H |
| 58 | 2-Br, 4-Cl | $CH_3$ | H |
| 59 | 2-Br, 5-Cl | $CH_3$ | H |
| 60 | 2-Br, 3-F | $CH_3$ | H |
| 61 | 2-Br, 4-F | $CH_3$ | H |
| 62 | 2-Br, 5-F | $CH_3$ | H |
| 63 | 2-Br, 6-F | $CH_3$ | H |
| 64 | 2-F, 3-Cl | $CH_3$ | H |
| 65 | 2-F, 4-Cl | $CH_3$ | H |
| 66 | 2-F, 5-Cl | $CH_3$ | H |
| 67 | 3-Cl, 4-F | $CH_3$ | H |
| 68 | 3-Cl, 5-F | $CH_3$ | H |
| 69 | 3-Cl, 4-Br | $CH_3$ | H |
| 70 | 3-Cl, 5-Br | $CH_3$ | H |
| 71 | 3-F, 4-Cl | $CH_3$ | H |
| 72 | 3-F, 4-Br | $CH_3$ | H |
| 73 | 3-Br, 4-Cl | $CH_3$ | H |
| 74 | 3-Br, 4-F | $CH_3$ | H |
| 75 | 2,6-$Cl_2$, 4-Br | $CH_3$ | H |
| 76 | 2-$CH_3$ | $CH_3$ | H |
| 77 | 3-$CH_3$ | $CH_3$ | H |
| 78 | 4-$CH_3$ | $CH_3$ | H |
| 79 | 2,3-$(CH_3)_2$ | $CH_3$ | H |
| 80 | 2,4-$(CH_3)_2$ | $CH_3$ | H |
| 81 | 2,5-$(CH_3)_2$ | $CH_3$ | H |
| 82 | 2,6-$(CH_3)_2$ | $CH_3$ | H |
| 83 | 3,4-$(CH_3)_2$ | $CH_3$ | H |
| 84 | 3,5-$(CH_3)_2$ | $CH_3$ | H |
| 85 | 2,3,5-$(CH_3)_3$ | $CH_3$ | H |
| 86 | 2,3,4-$(CH_3)_3$ | $CH_3$ | H |
| 87 | 2,3,6-$(CH_3)_3$ | $CH_3$ | H |
| 88 | 2,4,5-$(CH_3)_3$ | $CH_3$ | H |
| 89 | 2,4,6-$(CH_3)_3$ | $CH_3$ | H |
| 90 | 3,4,5-$(CH_3)_3$ | $CH_3$ | H |
| 91 | 2,3,4,6-$(CH_3)_4$ | $CH_3$ | H |
| 92 | 2,3,5,6-$(CH_3)_4$ | $CH_3$ | H |
| 93 | 2,3,4,5,6-$(CH_3)_5$ | $CH_3$ | H |
| 94 | 2-$C_2H_5$ | $CH_3$ | H |
| 95 | 3-$C_2H_5$ | $CH_3$ | H |
| 96 | 4-$C_2H_5$ | $CH_3$ | H |
| 97 | 2,4-$(C_2H_5)_5$ | $CH_3$ | H |
| 98 | 2,6-$(C_2H_5)_2$ | $CH_3$ | H |
| 99 | 3,5-$(C_2H_5)_2$ | $CH_3$ | H |
| 100 | 2,4,6-$(C_2H_5)_3$ | $CH_3$ | H |
| 101 | 2-n-$C_3H_7$ | $CH_3$ | H |
| 102 | 3-n-$C_3H_7$ | $CH_3$ | H |
| 103 | 4-n-$C_3H_7$ | $CH_3$ | H |
| 104 | 2-i-$C_3H_7$ | $CH_3$ | H |
| 105 | 3-i-$C_3H_7$ | $CH_3$ | H |
| 106 | 4-i-$C_3H_7$ | $CH_3$ | H |
| 107 | 2,4-(i-$C_3H_7)_2$ | $CH_3$ | H |
| 108 | 2,6-(i-$C_3H_7)_2$ | $CH_3$ | H |
| 109 | 3,5-(i-$C_3H_7)_2$ | $CH_3$ | H |
| 110 | 2-s-$C_4H_9$ | $CH_3$ | H |
| 111 | 3-s-$C_4H_9$ | $CH_3$ | H |
| 112 | 4-s-$C_4H_9$ | $CH_3$ | H |
| 113 | 2-t-$C_4H_9$ | $CH_3$ | H |
| 114 | 3-t-$C_4H_9$ | $CH_3$ | H |
| 115 | 4-t-$C_4H_9$ | $CH_3$ | H |
| 116 | 4-n-$C_9H_{19}$ | $CH_3$ | H |
| 117 | 2-$CH_3$, 4-t-$C_4H_9$ | $CH_3$ | H |
| 118 | 2-$CH_3$, 6-t-$C_4H_9$ | $CH_3$ | H |
| 119 | 2-$CH_3$, 4-i-$C_3H_7$ | $CH_3$ | H |
| 120 | 2-$CH_3$, 5-i-$C_3H_7$ | $CH_3$ | H |
| 121 | 3-$CH_3$, 4-i-$C_3H_7$ | $CH_3$ | H |
| 122 | 2-cyclo-$C_6H_{11}$ | $CH_3$ | H |
| 123 | 3-cyclo-$C_6H_{11}$ | $CH_3$ | H |
| 124 | 4-cyclo-$C_6H_{11}$ | $CH_3$ | H |
| 125 | 2-Cl, 4-$C_6H_5$ | $CH_3$ | H |
| 126 | 2-Br, 4-$C_6H_5$ | $CH_3$ | H |
| 127 | 2-$OCH_3$ | $CH_3$ | H |
| 128 | 3-$OCH_3$ | $CH_3$ | H |
| 129 | 4-$OCH_3$ | $CH_3$ | H |
| 130 | 2-$OC_2H_5$ | $CH_3$ | H |
| 131 | 3-O—$C_2H_5$ | $CH_3$ | H |
| 132 | 4-O—$C_2H_5$ | $CH_3$ | H |
| 133 | 2-O-n-$C_3H_7$ | $CH_3$ | H |
| 134 | 3-O-n-$C_3H_7$ | $CH_3$ | H |
| 135 | 4-O-n-$C_3H_7$ | $CH_3$ | H |
| 136 | 2-O-i-$C_3H_7$ | $CH_3$ | H |
| 137 | 3-O-i-$C_3H_7$ | $CH_3$ | H |
| 138 | 4-O-i-$C_3H_7$ | $CH_3$ | H |
| 139 | 2-O-n-$C_6H_{13}$ | $CH_3$ | H |
| 140 | 3-O-n-$C_6H_{13}$ | $CH_3$ | H |
| 141 | 4-O-n-$C_6H_{13}$ | $CH_3$ | H |
| 142 | 2-O—$CH_2C_6H_5$ | $CH_3$ | H |
| 143 | 3-O—$CH_2C_6H_5$ | $CH_3$ | H |
| 144 | 4-O—$CH_2C_6H_5$ | $CH_3$ | H |
| 145 | 2-O—$(CH_2)_3C_6H_5$ | $CH_3$ | H |
| 146 | 4-O—$(CH_2)_3C_6H_5$ | $CH_3$ | H |
| 147 | 2,3-$(OCH_3)_2$ | $CH_3$ | H |
| 148 | 2,4-$(OCH_3)_2$ | $CH_3$ | H |
| 149 | 2,5-$(OCH_3)_2$ | $CH_3$ | H |
| 150 | 2,6-$(OCH_3)_2$ | $CH_3$ | H |
| 151 | 3,4-$(OCH_3)_2$ | $CH_3$ | H |
| 152 | 3,5-$(OCH_3)_2$ | $CH_3$ | H |
| 153 | 2-O-t-$C_4H_9$ | $CH_3$ | H |
| 154 | 3-O-t-$C_4H_9$ | $CH_3$ | H |
| 155 | 4-O-t-$C_4H_9$ | $CH_3$ | H |
| 156 | 3-(3'-Cl—$C_6H_4$) | $CH_3$ | H |
| 157 | 4-(4'-$CH_3$—$C_6H_4$) | $CH_3$ | H |
| 158 | 2-O—$C_6H_5$ | $CH_3$ | H |
| 159 | 3-O—$C_6H_5$ | $CH_3$ | H |
| 160 | 4-O—$C_6H_5$ | $CH_3$ | H |
| 161 | 2-O-(2'-F—$C_6H_4$) | $CH_3$ | H |
| 162 | 3-O-(3'-Cl—$C_6H_4$) | $CH_3$ | H |
| 163 | 4-O-(4'-$CH_3$—$C_6H_4$) | $CH_3$ | H |
| 164 | 2,3,6-$(CH_3)_3$, 4-F | $CH_3$ | H |
| 165 | 2,3,6-$(CH_3)_3$, 4-Cl | $CH_3$ | H |
| 166 | 2,3,6-$(CH_3)_3$, 4-Br | $CH_3$ | H |
| 167 | 2,4-$(CH_3)_2$, 6-F | $CH_3$ | H |
| 168 | 2,4-$(CH_3)_2$, 6-Cl | $CH_3$ | H |
| 169 | 2,4-$(CH_3)_2$, 6-Br | $CH_3$ | H |
| 170 | 2-i-$CH_3H_1$, 4-Cl, 5-$CH_3$ | $CH_3$ | H |

TABLE A-continued

| Number | $R_m$ | $R^2$ | $R^1_n$ |
|---|---|---|---|
| 171 | 2-Cl, 4-NO$_2$ | CH$_3$ | H |
| 172 | 2-NO$_2$, 4-Cl | CH$_3$ | H |
| 173 | 2-OCH$_3$, 5-NO$_2$ | CH$_3$ | H |
| 174 | 2,4-Cl$_2$, 5-NO$_2$ | CH$_3$ | H |
| 175 | 2,4-Cl$_2$, 6-NO$_2$ | CH$_3$ | H |
| 176 | 2,6-Cl$_2$, 4-NO$_2$ | CH$_3$ | H |
| 177 | 2,6-Br$_2$, 4-NO$_2$ | CH$_3$ | H |
| 178 | 2,6-I$_2$, 4-NO$_2$ | CH$_3$ | H |
| 179 | 2-CH$_3$, 5-i-C$_3$H$_7$, 4-Cl | CH$_3$ | H |
| 180 | 2-CO$_2$CH$_3$ | CH$_3$ | H |
| 181 | 3-CO$_2$CH$_3$ | CH$_3$ | H |
| 182 | 4-CO$_2$CH$_3$ | CH$_3$ | H |
| 183 | 2-CH$_2$—OCH$_3$ | CH$_3$ | H |
| 184 | 3-CH$_2$—OCH$_3$ | CH$_3$ | H |
| 185 | 4-CH$_2$—OCH$_3$ | CH$_3$ | H |
| 186 | 2-Me-4-CH$_3$—CH(CH$_3$)—CO | CH$_3$ | H |
| 187 | 2-CH$_3$-4-(CH$_3$—C=NOCH$_3$) | CH$_3$ | H |
| 188 | 2-CH$_3$-4-(CH$_3$—C=NOC$_2$H$_5$) | CH$_3$ | H |
| 189 | 2-CH$_3$-4-(CH$_3$—C=NO-n-C$_3$H$_7$) | CH$_3$ | H |
| 190 | 2-CH$_3$-4-(CH$_3$—C=NO-i-C$_3$H$_7$) | CH$_3$ | H |
| 191 | 2,5-(CH$_3$)2-4-(CH$_3$—C=NOCH$_3$) | CH$_3$ | H |
| 192 | 2,5-(CH$_3$)2-4-(CH$_3$—C=NOC$_2$H$_5$) | CH$_3$ | H |
| 193 | 2,5-(CH$_3$)$_2$-4-(CH$_3$—C=NO-n-C$_3$H$_7$) | CH$_3$ | H |
| 194 | 2,5-(CH$_3$)$_2$-4-(CH$_3$—C=NO-i-C$_3$H$_7$) | CH$_3$ | H |
| 195 | 2-C$_6$H$_5$ | CH$_3$ | H |
| 196 | 3-C$_6$H$_5$ | CH$_3$ | H |
| 197 | 4-C$_6$H$_5$ | CH$_3$ | H |
| 198 | 2-(2'-F—C$_6$H$_4$) | CH$_3$ | H |
| 199 | 2-CH$_3$, 5-Br | CH$_3$ | H |
| 200 | 2-CH$_3$, 6-Br | CH$_3$ | H |
| 201 | 2-Cl, 3-CH$_3$ | CH$_3$ | H |
| 202 | 2-Cl, 4-CH$_3$ | CH$_3$ | H |
| 203 | 2-Cl, 5-CH$_3$ | CH$_3$ | H |
| 204 | 2-F, 3-CH$_3$ | CH$_3$ | H |
| 205 | 2-F, 4-CH$_3$ | CH$_3$ | H |
| 206 | 2-F, 5-CH$_3$ | CH$_3$ | H |
| 207 | 2-Br, 3-CH$_3$ | CH$_3$ | H |
| 208 | 2-Br, 4-CH$_3$ | CH$_3$ | H |
| 209 | 2-Br, 5-CH$_3$ | CH$_3$ | H |
| 210 | 3-CH$_3$, 4-Cl | CH$_3$ | H |
| 211 | 3-CH$_3$, 5-Cl | CH$_3$ | H |
| 212 | 3-CH$_3$, 4-F | CH$_3$ | H |
| 213 | 3-CH$_3$, 5-F | CH$_3$ | H |
| 214 | 3-CH$_3$, 4-Br | CH$_3$ | H |
| 215 | 3-CH$_3$, 5-Br | CH$_3$ | H |
| 216 | 3-F, 4-CH$_3$ | CH$_3$ | H |
| 217 | 3-Cl, 4-CH$_3$ | CH$_3$ | H |
| 218 | 3-Br, 4-CH$_3$ | CH$_3$ | H |
| 219 | 2-Cl, 4,5-(CH$_3$)$_2$ | CH$_3$ | H |
| 220 | 2-Br, 4,5-(CH$_3$)$_2$ | CH$_3$ | H |
| 221 | 2-Cl, 3,5-(CH$_3$)$_2$ | CH$_3$ | H |
| 222 | 2-Br, 3,5-(CH$_3$)$_2$ | CH$_3$ | H |
| 223 | 2,6-Cl$_2$, 4-CH$_3$ | CH$_3$ | H |
| 224 | 2,6-F$_2$, 4-CH$_3$ | CH$_3$ | H |
| 225 | 2,6-Br$_2$, 4-CH$_3$ | CH$_3$ | H |
| 226 | 2,4-Br$_2$, 6-CH$_3$ | CH$_3$ | H |
| 227 | 2,4-F$_2$, 6-CH$_3$ | CH$_3$ | H |
| 228 | 2,4-Br$_2$, 6-CH$_3$ | CH$_3$ | H |
| 229 | 2,6-(CH$_3$)$_2$, 4-F | CH$_3$ | H |
| 230 | 2,6-(CH$_3$)$_2$, 4-Cl | CH$_3$ | H |
| 231 | 2,6-(CH$_3$)$_2$, 4-Br | CH$_3$ | H |
| 232 | 3,5-(CH$_3$)$_2$, 4-F | CH$_3$ | H |
| 233 | 3,5-(CH$_3$)$_2$, 4-Cl | CH$_3$ | H |
| 234 | 3,5-(CH$_3$)$_2$, 4-Br | CH$_3$ | H |
| 235 | 2-CF$_3$ | CH$_3$ | H |
| 236 | 3-CF$_3$ | CH$_3$ | H |
| 237 | 4-CF$_3$ | CH$_3$ | H |
| 238 | 2-OCF$_3$ | CH$_3$ | H |
| 239 | 3-OCF$_3$ | CH$_3$ | H |
| 240 | 4-OCF$_3$ | CH$_3$ | H |
| 241 | 3-OCH$_2$CHF$_2$ | CH$_3$ | H |
| 242 | 2-NO$_2$ | CH$_3$ | H |
| 243 | 3-NO$_2$ | CH$_3$ | H |
| 244 | 4-NO$_2$ | CH$_3$ | H |
| 245 | 2-CN | CH$_3$ | H |
| 246 | 3-CN | CH$_3$ | H |
| 247 | 4-CN | CH$_3$ | H |
| 248 | 2-CH$_3$, 3-Cl | CH$_3$ | H |
| 249 | 2-CH$_3$, 4-Cl | CH$_3$ | H |
| 250 | 2-CH$_3$, 5-Cl | CH$_3$ | H |
| 251 | 2-CH$_3$, 6-Cl | CH$_3$ | H |
| 252 | 2-CH$_3$, 3-F | CH$_3$ | H |
| 253 | 2-CH$_3$, 4-F | CH$_3$ | H |
| 254 | 2-CH$_3$, 5-F | CH$_3$ | H |
| 255 | 2-CH$_3$, 6-F | CH$_3$ | H |
| 256 | 2-CH$_3$, 3-Br | CH$_3$ | H |
| 257 | 2-CH$_3$, 4-Br | CH$_3$ | H |
| 258 | 2-Pyridyl-2' | CH$_3$ | H |
| 259 | 3-Pyridyl-3' | CH$_3$ | H |
| 260 | 4-Pyridyl-4' | CH$_3$ | H |
| 261 | 2-CO—CH$_3$ | CH$_3$ | H |
| 262 | 3-CO—CH$_3$ | CH$_3$ | H |
| 263 | 4-CO—CH$_3$ | CH$_3$ | H |
| 264 | 2-C(=N—OCH$_3$)—CH$_3$ | CH$_3$ | H |
| 265 | 3-C(=N—OCH$_3$)—CH$_3$ | CH$_3$ | H |
| 266 | 4-C(=N—OCH$_3$)—CH$_3$ | CH$_3$ | H |
| 267 | 2-F | F | H |
| 268 | 3-F | F | H |
| 269 | 4-F | F | H |
| 270 | 2,4-F$_2$ | F | H |
| 271 | 2,4,6-F$_3$ | F | H |
| 272 | 2,3,4,5,6-F$_5$ | F | H |
| 273 | 2,3-F$_2$ | F | H |
| 274 | 2-Cl | F | H |
| 275 | 3-Cl | F | H |
| 276 | 4-Cl | F | H |
| 277 | 2,3-Cl$_2$ | F | H |
| 278 | 2,4-Cl$_2$ | F | H |
| 279 | 2,5-Cl$_2$ | F | H |
| 280 | 2,6-Cl$_2$ | F | H |
| 281 | 3,4-Cl$_2$ | F | H |
| 282 | 3,5-Cl$_2$ | F | H |
| 283 | 2,3,4-Cl$_3$ | F | H |
| 284 | 2,3,5-Cl$_3$ | F | H |
| 285 | 2,3,6-Cl$_3$ | F | H |
| 286 | 2,4,5-Cl$_3$ | F | H |
| 287 | 2,4,6-Cl$_3$ | F | H |
| 288 | 3,4,5-Cl$_3$ | F | H |
| 289 | 2,3,4,6-Cl$_4$ | F | H |
| 290 | 2,3,5,6-Cl$_4$ | F | H |
| 291 | 2,3,4,5,6-Cl$_5$ | F | H |
| 292 | 2-Br | F | H |
| 293 | 3-Br | F | H |
| 294 | 4-Br | F | H |
| 295 | 2,4-Br$_2$ | F | H |
| 296 | 2,5-Br$_2$ | F | H |
| 297 | 2,6-Br$_2$ | F | H |
| 298 | 2,4,6-Br$_3$ | F | H |
| 299 | 2,3,4,5,6-Br$_5$ | F | H |
| 300 | 2-I | F | H |
| 301 | 3-I | F | H |
| 302 | 4-I | F | H |
| 303 | 2,4-I$_2$ | F | H |
| 304 | 2-Cl, 3-F | F | H |
| 305 | 2-Cl, 4-F | F | H |
| 306 | 2-Cl, 5-F | F | H |
| 307 | 2-Cl, 6-F | F | H |
| 308 | 2-Cl, 3-Br | F | H |
| 309 | 2-Cl, 4-Br | F | H |
| 310 | 2-Cl, 5-Br | F | H |
| 311 | 2-Cl, 6-Br | F | H |
| 312 | 2-Br, 3-Cl | F | H |
| 313 | 2-Br, 4-Cl | F | H |
| 314 | 2-Br, 5-Cl | F | H |
| 315 | 2-Br, 3-F | F | H |
| 316 | 2-Br, 4-F | F | H |
| 317 | 2-Br, 5-F | F | H |
| 318 | 2-Br, 6-F | F | H |
| 319 | 2-F, 3-Cl | F | H |
| 320 | 2-F, 4-Cl | F | H |
| 321 | 2-F, 5-Cl | F | H |
| 322 | 3-Cl, 4-F | F | H |
| 323 | 3-Cl, 5-F | F | H |
| 324 | 3-Cl, 4-Br | F | H |

TABLE A-continued

| Number | $R_m$ | $R^2$ | $R^1_n$ |
|---|---|---|---|
| 325 | 3-Cl, 5-Br | F | H |
| 326 | 3-F, 4-Cl | F | H |
| 327 | 3-F, 4-Br | F | H |
| 328 | 3-Br, 4-Cl | F | H |
| 329 | 3-Br, 4-F | F | H |
| 330 | 2,6-Cl$_2$, 4-Br | F | H |
| 331 | 2-CH$_3$ | F | H |
| 332 | 3-CH$_3$ | F | H |
| 333 | 4-CH$_3$ | F | H |
| 334 | 2,3-(CH$_3$)$_2$ | F | H |
| 335 | 2,4-(CH$_3$)$_2$ | F | H |
| 336 | 2,5-(CH$_3$)$_2$ | F | H |
| 337 | 2,6-(CH$_3$)$_2$ | F | H |
| 338 | 3,4-(CH$_3$)$_2$ | F | H |
| 339 | 3,5-(CH$_3$)$_2$ | F | H |
| 340 | 2,3,5-(CH$_3$)$_3$ | F | H |
| 341 | 2,3,4-(CH$_3$)$_3$ | F | H |
| 342 | 2,3,6-(CH$_3$)$_3$ | F | H |
| 343 | 2,4,5-(CH$_3$)$_3$ | F | H |
| 344 | 2,4,6-(CH$_3$)$_3$ | F | H |
| 345 | 3,4,5-(CH$_3$)$_3$ | F | H |
| 346 | 2,3,4,6-(CH$_3$)$_4$ | F | H |
| 347 | 2,3,5,6-(CH$_3$)$_4$ | F | H |
| 348 | 2,3,4,5,6-(CH$_3$)$_5$ | F | H |
| 349 | 2-C$_2$H$_5$ | F | H |
| 350 | 3-C$_2$H$_5$ | F | H |
| 351 | 4-C$_2$H$_5$ | F | H |
| 352 | 2,4-(C$_2$H$_5$)$_2$ | F | H |
| 353 | 2,6-(C$_2$H$_5$)$_2$ | F | H |
| 354 | 3,5-(C$_2$H$_5$)$_2$ | F | H |
| 355 | 2,4,6-(C$_2$H$_5$)$_3$ | F | H |
| 356 | 2-n-C$_3$H$_7$ | F | H |
| 357 | 3-n-C$_3$H$_7$ | F | H |
| 358 | 4-n-C$_3$H$_7$ | F | H |
| 359 | 2-i-C$_3$H$_7$ | F | H |
| 360 | 3-i-C$_3$H$_7$ | F | H |
| 361 | 4-i-C$_3$H$_7$ | F | H |
| 362 | 2,4-(i-C$_3$H$_7$)$_2$ | F | H |
| 363 | 2,6-(i-C$_3$H$_7$)$_2$ | F | H |
| 364 | 3,5-(i-C$_3$H$_7$)$_2$ | F | H |
| 365 | 2-s-C$_4$H$_9$ | F | H |
| 366 | 3-s-C$_4$H$_9$ | F | H |
| 367 | 4-s-C$_4$H$_9$ | F | H |
| 368 | 2-t-C$_4$H$_9$ | F | H |
| 369 | 3-t-C$_4$H$_9$ | F | H |
| 370 | 4-t-C$_4$H$_9$ | F | H |
| 371 | 4-n-C$_9$H$_{19}$ | F | H |
| 372 | 2-CH$_3$, 4-t-C$_4$H$_9$ | F | H |
| 373 | 2-CH$_3$, 6-t-C$_4$H$_9$ | F | H |
| 374 | 2-CH$_3$, 4-i-C$_3$H$_7$ | F | H |
| 375 | 2-CH$_3$, 5-i-C$_3$H$_7$ | F | H |
| 376 | 3-CH$_3$, 4-i-C$_3$H$_7$ | F | H |
| 377 | 2-cyclo-C$_6$H$_{11}$ | F | H |
| 378 | 3-cyclo-C$_6$H$_{11}$ | F | H |
| 379 | 4-cyclo-C$_6$H$_{11}$ | F | H |
| 380 | 2-Cl, 4-C$_6$H$_5$ | F | H |
| 381 | 2-Br, 4-C$_6$H$_5$ | F | H |
| 382 | 2-OCH$_3$ | F | H |
| 383 | 3-OCH$_3$ | F | H |
| 384 | 4-OCH$_3$ | F | H |
| 385 | 2-OC$_2$H$_5$ | F | H |
| 386 | 3-O—C$_2$H$_5$ | F | H |
| 387 | 4-O—C$_2$H$_5$ | F | H |
| 388 | 2-O-n-C$_3$H$_7$ | F | H |
| 389 | 3-O-n-C$_3$H$_7$ | F | H |
| 390 | 4-O-n-C$_3$H$_7$ | F | H |
| 391 | 2-O-i-C$_3$H$_7$ | F | H |
| 392 | 3-O-i-C$_3$H$_7$ | F | H |
| 393 | 4-O-i-C$_3$H$_7$ | F | H |
| 394 | 2-O-n-C$_6$H$_{13}$ | F | H |
| 395 | 3-O-n-C$_6$H$_{13}$ | F | H |
| 396 | 4-O-n-C$_6$H$_{13}$ | F | H |
| 397 | 2-O—CH$_2$C$_6$H$_5$ | F | H |
| 398 | 3-O—CH$_2$C$_6$H$_5$ | F | H |
| 399 | 4-O—CH$_2$C$_6$H$_5$ | F | H |
| 400 | 2-O—(CH$_2$)$_3$C$_6$H$_5$ | F | H |
| 401 | 4-O—(CH$_2$)$_3$C$_6$H$_5$ | F | H |
| 402 | 2,3-(OCH$_3$)$_2$ | F | H |
| 403 | 2,4-(OCH$_3$)$_2$ | F | H |
| 404 | 2,5-(OCH$_3$)$_2$ | F | H |
| 405 | 2,6-(OCH$_3$)$_2$ | F | H |
| 406 | 3,4-(OCH$_3$)$_2$ | F | H |
| 407 | 3,5-(OCH$_3$)$_2$ | F | H |
| 408 | 2-O-t-C$_4$H$_9$ | F | H |
| 409 | 3-O-t-C$_4$H$_9$ | F | H |
| 410 | 4-O-t-C$_4$H$_9$ | F | H |
| 411 | 3-(3'-Cl—C$_6$H$_4$) | F | H |
| 412 | 4-(4'-CH$_3$—C$_6$H$_4$) | F | H |
| 413 | 2-O—C$_6$H$_5$ | F | H |
| 414 | 3-O—C$_6$H$_5$ | F | H |
| 415 | 4-O—C$_6$H$_5$ | F | H |
| 416 | 2-O-(2'-F—C$_6$H$_4$) | F | H |
| 417 | 3-O-(3'-Cl—C$_6$H$_4$) | F | H |
| 418 | 4-O-(4'-CH$_3$—C$_6$H$_4$) | F | H |
| 419 | 2,3,6-(CH$_3$)$_3$, 4-F | F | H |
| 420 | 2,3,6-(CH$_3$)$_3$, 4-Cl | F | H |
| 421 | 2,3,6-(CH$_3$)$_3$, 4-Br | F | H |
| 422 | 2,4-(CH$_3$)2, 6-F | F | H |
| 423 | 2,4-(CH$_3$)2, 6-Cl | F | H |
| 424 | 2,4-(CH$_3$)2, 6-Br | F | H |
| 425 | 2-i-C$_3$H$_7$, 4-Cl, 5-CH$_3$ | F | H |
| 426 | 2-Cl, 4-NO$_2$ | F | H |
| 427 | 2-NO$_2$, 4-Cl | F | H |
| 428 | 2-OCH$_3$, 5-NO$_2$ | F | H |
| 429 | 2,4-Cl$_2$, 5-NO$_2$ | F | H |
| 430 | 2,4-Cl$_2$, 6-NO$_2$ | F | H |
| 431 | 2,6-Cl$_2$, 4-NO$_2$ | F | H |
| 432 | 2,6-Br$_2$, 4-NO$_2$ | F | H |
| 433 | 2,6-I$_2$, 4-NO$_2$ | F | H |
| 434 | 2-CH$_3$, 5-i-C$_3$H$_7$, 4-Cl | F | H |
| 435 | 2-CO$_2$CH$_3$ | F | H |
| 436 | 3-CO$_2$CH$_3$ | F | H |
| 437 | 4-CO$_2$CH$_3$ | F | H |
| 438 | 2-CH$_2$—OCH$_3$ | F | H |
| 439 | 3-CH$_2$—OCH$_3$ | F | H |
| 440 | 4-CH$_2$—OCH$_3$ | F | H |
| 441 | 2-Me-4-CH$_3$—CH(CH$_3$)—CO | F | H |
| 442 | 2-CH$_3$-4-(CH$_3$—C=NOCH$_3$) | F | H |
| 443 | 2-CH$_3$-4-(CH$_3$—C=NOC$_2$H$_5$) | F | H |
| 444 | 2-CH$_3$-4-(CH$_3$—C=NO-n-C$_3$H$_7$) | F | H |
| 445 | 2-CH$_3$-4- ( CH$_3$—C=NO-i-C$_3$H$_7$) | F | H |
| 446 | 2,5-(CH$_3$)2-4-(CH$_3$—C=NOCH$_3$) | F | H |
| 447 | 2,5-(CH$_3$)2-4-(CH$_3$—C=NOC$_2$H$_5$) | F | H |
| 448 | 2,5-(CH$_3$-4-(CH$_3$—C=NO-n-C$_3$H$_7$) | F | H |
| 449 | 2,5-(CH$_3$)2-4-(CH$_3$—C=NO-i-C$_3$H$_7$) | F | H |
| 450 | 2-C$_6$H$_5$ | F | H |
| 451 | 3-C$_6$H$_5$ | F | H |
| 452 | 4-C$_6$H$_5$ | F | H |
| 453 | 2-(2'-F—C$_6$H$_4$) | F | H |
| 454 | 2-CH$_3$, 5-Br | F | H |
| 455 | 2-CH$_3$, 6-Br | F | H |
| 456 | 2-Cl, 3-CH$_3$ | F | H |
| 457 | 2-Cl, 4-CH$_3$ | F | H |
| 458 | 2-Cl, 5-CH$_3$ | F | H |
| 459 | 2-F, 3-CH$_3$ | F | H |
| 460 | 2-F, 4-CH$_3$ | F | H |
| 461 | 2-F, 5-CH$_3$ | F | H |
| 462 | 2-Br, 3-CH$_3$ | F | H |
| 463 | 2-Br, 4-CH$_3$ | F | H |
| 464 | 2-Br, 5-CH$_3$ | F | H |
| 465 | 3-CH$_3$, 4-Cl | F | H |
| 466 | 3-CH$_3$, 5-Cl | F | H |
| 467 | 3-CH$_3$, 4-F | F | H |
| 468 | 3-CH$_3$, 5-F | F | H |
| 469 | 3-CH$_3$, 4-Br | F | H |
| 470 | 3-CH$_3$, 5-Br | F | H |
| 471 | 3-F, 4-CH$_3$ | F | H |
| 472 | 3-Cl, 4-CH$_3$ | F | H |
| 473 | 3-Br, 4-CH$_3$ | F | H |
| 474 | 2-Cl, 4,5-(CH$_3$)$_2$ | F | H |
| 475 | 2-Br, 4,5-(CH$_3$)$_2$ | F | H |
| 476 | 2-Cl, 3,5-(CH$_3$)$_2$ | F | H |
| 477 | 2-Br, 3,5-(CH$_3$)$_2$ | F | H |
| 478 | 2,6-Cl$_2$, 4-CH$_3$ | F | H |

TABLE A-continued

| Number | $R_m$ | $R^2$ | $R^1_n$ |
|---|---|---|---|
| 479 | 2,6-F$_2$, 4-CH$_3$ | F | H |
| 480 | 2,6-Br$_2$, 4-CH$_3$ | F | H |
| 481 | 2,4-Br$_2$, 6-CH$_3$ | F | H |
| 482 | 2,4-F$_2$, 6-CH$_3$ | F | H |
| 483 | 2,4-Br$_2$, 6-CH$_3$ | F | H |
| 484 | 2,6-(CH$_3$)$_2$, 4-F | F | H |
| 485 | 2,6-(CH$_3$)$_2$, 4-Cl | F | H |
| 486 | 2,6-(CH$_3$)$_2$, 4-Br | F | H |
| 487 | 3,5-(CH$_3$)$_2$, 4-F | F | H |
| 488 | 3,5-(CH$_3$)$_2$, 4-Cl | F | H |
| 489 | 3,5-(CH$_3$)$_2$, 4-Br | F | H |
| 490 | 2-CF$_3$ | F | H |
| 491 | 3-CF$_3$ | F | H |
| 492 | 4-CF$_3$ | F | H |
| 493 | 2-OCF$_3$ | F | H |
| 494 | 3-OCF$_3$ | F | H |
| 495 | 4-OCF$_3$ | F | H |
| 496 | 3-OCH$_2$CHF$_2$ | F | H |
| 497 | 2-NO$_2$ | F | H |
| 498 | 3-NO$_2$ | F | H |
| 499 | 4-NO$_2$ | F | H |
| 500 | 2-CN | F | H |
| 501 | 3-CN | F | H |
| 502 | 4-CN | F | H |
| 503 | 2-CH$_3$, 3-Cl | F | H |
| 504 | 2-CH$_3$, 4-Cl | F | H |
| 505 | 2-CH$_3$, 5-Cl | F | H |
| 506 | 2-CH$_3$, 6-Cl | F | H |
| 507 | 2-CH$_3$, 3-F | F | H |
| 508 | 2-CH$_3$, 4-F | F | H |
| 509 | 2-CH$_3$, 5-F | F | H |
| 510 | 2-CH$_3$, 6-F | F | H |
| 511 | 2-CH$_3$, 3-Br | F | H |
| 512 | 2-CH$_3$, 4-Br | F | H |
| 513 | 2-Pyridyl-2' | F | H |
| 514 | 3-Pyridyl-3' | F | H |
| 515 | 4-Pyridyl-4' | F | H |
| 516 | 2-CO—CH$_3$ | F | H |
| 517 | 3-CO—CH$_3$ | F | H |
| 518 | 4-CO—CH$_3$ | F | H |
| 519 | 2-C(=N—OCH$_3$)—CH$_3$ | F | H |
| 520 | 3-C(=N—OCH$_3$)—CH$_3$ | F | H |
| 521 | 4-C(=N—OCH$_3$)—CH$_3$ | F | H |
| 522 | 2-F | Cl | H |
| 523 | 3-F | Cl | H |
| 524 | 4-F | Cl | H |
| 525 | 2,4-F$_2$ | Cl | H |
| 526 | 2,4,6-F$_3$ | Cl | H |
| 527 | 2,3,4,5,6-F$_5$ | Cl | H |
| 528 | 2,3-F$_2$ | Cl | H |
| 529 | 2-Cl | Cl | H |
| 530 | 3-Cl | Cl | H |
| 531 | 4-Cl | Cl | H |
| 532 | 2,3-Cl$_2$ | Cl | H |
| 533 | 2,4-Cl$_2$ | Cl | H |
| 534 | 2,5-Cl$_2$ | Cl | H |
| 535 | 2,6-Cl$_2$ | Cl | H |
| 536 | 3,4-Cl$_2$ | Cl | H |
| 537 | 3,5-Cl$_2$ | Cl | H |
| 538 | 2,3,4-Cl$_3$ | Cl | H |
| 539 | 2,3,5-Cl$_3$ | Cl | H |
| 540 | 2,3,6-Cl$_3$ | Cl | H |
| 541 | 2,4,5-Cl$_3$ | Cl | H |
| 542 | 2,4,6-Cl$_3$ | Cl | H |
| 543 | 3,4,5-Cl$_3$ | Cl | H |
| 544 | 2,3,4,6-Cl$_4$ | Cl | H |
| 545 | 2,3,5,6-Cl$_4$ | Cl | H |
| 546 | 2,3,4,5,6-Cl$_5$ | Cl | H |
| 547 | 2-Br | Cl | H |
| 548 | 3-Br | Cl | H |
| 549 | 4-Br | Cl | H |
| 550 | 2,4-Br$_2$ | Cl | H |
| 551 | 2,5-Br$_2$ | Cl | H |
| 552 | 2,6-Br$_2$ | Cl | H |
| 553 | 2,4,6-Br$_3$ | Cl | H |
| 554 | 2,3,4,5,6-Br$_5$ | Cl | H |
| 555 | 2-I | Cl | H |
| 556 | 3-I | Cl | H |
| 557 | 4-I | Cl | H |
| 558 | 2,4-I$_2$ | Cl | H |
| 559 | 2-Cl, 3-F | Cl | H |
| 560 | 2-Cl, 4-F | Cl | H |
| 561 | 2-Cl, 5-F | Cl | H |
| 562 | 2-Cl, 6-F | Cl | H |
| 563 | 2-Cl, 3-Br | Cl | H |
| 564 | 2-Cl, 4-Br | Cl | H |
| 565 | 2-Cl, 5-Br | Cl | H |
| 566 | 2-Cl, 6-Br | Cl | H |
| 567 | 2-Br, 3-Cl | Cl | H |
| 568 | 2-Br, 4-Cl | Cl | H |
| 569 | 2-Br, 5-Cl | Cl | H |
| 570 | 2-Br, 3-F | Cl | H |
| 571 | 2-Br, 4-F | Cl | H |
| 572 | 2-Br, 5-F | Cl | H |
| 573 | 2-Br, 6-F | Cl | H |
| 574 | 2-F, 3-Cl | Cl | H |
| 575 | 2-F, 4-Cl | Cl | H |
| 576 | 2-F, 5-Cl | Cl | H |
| 577 | 3-Cl, 4-F | Cl | H |
| 578 | 3-Cl, 5-F | Cl | H |
| 579 | 3-Cl, 4-Br | Cl | H |
| 580 | 3-Cl, 5-Br | Cl | H |
| 581 | 3-F, 4-Cl | Cl | H |
| 582 | 3-F, 4-Br | Cl | H |
| 583 | 3-Br, 4-Cl | Cl | H |
| 584 | 3-Br, 4-F | Cl | H |
| 585 | 2,6-Cl$_2$, 4-Br | Cl | H |
| 586 | 2-CH$_3$ | Cl | H |
| 587 | 3-CH$_3$ | Cl | H |
| 588 | 4-CH$_3$ | Cl | H |
| 589 | 2,3-(CH$_3$)$_2$ | Cl | H |
| 590 | 2,4-(CH$_3$)$_2$ | Cl | H |
| 591 | 2,5-(CH$_3$)$_2$ | Cl | H |
| 592 | 2,6-(CH$_3$)$_2$ | Cl | H |
| 593 | 3,4-(CH$_3$)$_2$ | Cl | H |
| 594 | 3,5-(CH$_3$)$_2$ | Cl | H |
| 595 | 2,3,5-(CH$_3$)$_3$ | Cl | H |
| 596 | 2,3,4-(CH$_3$)$_3$ | Cl | H |
| 597 | 2,3,6-(CH$_3$)$_3$ | Cl | H |
| 598 | 2,4,5-(CH$_3$)$_3$ | Cl | H |
| 599 | 2,4,6-(CH$_3$)$_3$ | Cl | H |
| 600 | 3,4,5-(CH$_3$)$_3$ | Cl | H |
| 601 | 2,3,4,6-(CH$_3$)$_4$ | Cl | H |
| 602 | 2,3,5,6-(CH$_3$)$_4$ | Cl | H |
| 603 | 2,3,4,5,6-(CH$_3$)$_5$ | Cl | H |
| 604 | 2-C$_2$H$_5$ | Cl | H |
| 605 | 3-C$_2$H$_5$ | Cl | H |
| 606 | 4-C$_2$H$_5$ | Cl | H |
| 607 | 2,4-(C$_2$H$_5$)$_2$ | Cl | H |
| 608 | 2,6-(C$_2$H$_5$)$_2$ | Cl | H |
| 609 | 3,5-(C$_2$H$_5$)$_2$ | Cl | H |
| 610 | 2,4,6-(C$_2$H$_5$)$_3$ | Cl | H |
| 611 | 2-n-C$_3$H$_7$ | Cl | H |
| 612 | 3-n-C$_3$H$_7$ | Cl | H |
| 613 | 4-n-C$_3$H$_7$ | Cl | H |
| 614 | 2-i-C$_3$H$_7$ | Cl | H |
| 615 | 3-i-C$_3$H$_7$ | Cl | H |
| 616 | 4-i-C$_3$H$_7$ | Cl | H |
| 617 | 2,4-(i-C$_3$H$_7$)$_2$ | Cl | H |
| 618 | 2,6-(i-C$_3$H$_7$)$_2$ | Cl | H |
| 619 | 3,5-(i-C$_3$H$_7$)$_2$ | Cl | H |
| 620 | 2-s-C$_4$H$_9$ | Cl | H |
| 621 | 3-s-C$_4$H$_9$ | Cl | H |
| 622 | 4-s-C$_4$H$_9$ | Cl | H |
| 623 | 2-t-C$_4$H$_9$ | Cl | H |
| 624 | 3-t-C$_4$H$_9$ | Cl | H |
| 625 | 4-t-C$_4$H$_9$ | Cl | H |
| 626 | 4-n-C$_9$H$_{19}$ | Cl | H |
| 627 | 2-CH$_3$, 4-t-C$_4$H$_9$ | Cl | H |
| 628 | 2-CH$_3$, 6-t-C$_4$H$_9$ | Cl | H |
| 629 | 2-CH$_3$, 4-i-C$_3$H$_7$ | Cl | H |
| 630 | 2-CH$_3$, 5-i-C$_3$H$_7$ | Cl | H |
| 631 | 3-CH$_3$, 4-i-C$_3$H$_7$ | Cl | H |
| 632 | 2-cyclo-C$_6$H$_{11}$ | Cl | H |

TABLE A-continued

| Number | $R_m$ | $R^2$ | $R^1_n$ |
|---|---|---|---|
| 633 | 3-cyclo-$C_6H_{11}$ | Cl | H |
| 634 | 4-cyclo-$C_6H_{11}$ | Cl | H |
| 635 | 2-Cl, 4-$C_6H_5$ | Cl | H |
| 636 | 2-Br, 4-$C_6H_5$ | Cl | H |
| 637 | 2-$OCH_3$ | Cl | H |
| 638 | 3-$OCH_3$ | Cl | H |
| 639 | 4-$OCH_3$ | Cl | H |
| 640 | 2-$OC_2H_5$ | Cl | H |
| 641 | 3-O—$C_2H_5$ | Cl | H |
| 642 | 4-O—$C_2H_5$ | Cl | H |
| 643 | 2-O-n-$C_3H_7$ | Cl | H |
| 644 | 3-O-n-$C_3H_7$ | Cl | H |
| 645 | 4-O-n-$C_3H_7$ | Cl | H |
| 646 | 2-O-i-$C_3H_7$ | Cl | H |
| 647 | 3-O-i-$C_3H_7$ | Cl | H |
| 648 | 4-O-i-$C_3H_7$ | Cl | H |
| 649 | 2-O-n-$C_6H_{13}$ | Cl | H |
| 650 | 3-O-n-$C_6H_{13}$ | Cl | H |
| 651 | 4-O-n-$C_6H_{13}$ | Cl | H |
| 652 | 2-O—$CH_2C_6H_5$ | Cl | H |
| 653 | 3-O—$CH_2C_6H_5$ | Cl | H |
| 654 | 4-O—$CH_2C_6H_5$ | Cl | H |
| 655 | 2-O—$(CH_2)_3C_6H_5$ | Cl | H |
| 656 | 4-O—$(CH_2)_3C_6H_5$ | Cl | H |
| 657 | 2,3-$(OCH_3)_2$ | Cl | H |
| 658 | 2,4-$(OCH_3)_2$ | Cl | H |
| 659 | 2,5-$(OCH_3)_2$ | Cl | H |
| 660 | 2,6-$(OCH_3)_2$ | Cl | H |
| 661 | 3,4-$(OCH_3)_2$ | Cl | H |
| 662 | 3,5-$(OCH_3)_2$ | Cl | H |
| 663 | 2-O-t-$C_4H_9$ | Cl | H |
| 664 | 3-O-t-$C_4H_9$ | Cl | H |
| 665 | 4-O-t-$C_4H_9$ | Cl | H |
| 666 | 3-(3'-Cl—$C_6H_4$) | Cl | H |
| 667 | 4-(4'-$CH_3$—$C_6H_4$) | Cl | H |
| 668 | 2-O—$C_6H_5$ | Cl | H |
| 669 | 3-O—$C_6H_5$ | Cl | H |
| 670 | 4-O—$C_6H_5$ | Cl | H |
| 671 | 2-O-(2'-F—$C_6H_4$) | Cl | H |
| 672 | 3-O-(3'-Cl—$C_6H_4$) | Cl | H |
| 673 | 4-O-(4'-$CH_3$—$C_6H_4$) | Cl | H |
| 674 | 2,3,6-$(CH_3)_3$, 4-F | Cl | H |
| 675 | 2,3,6-$(CH_3)_3$, 4-Cl | Cl | H |
| 676 | 2,3,6-$(CH_3)_3$, 4-Br | Cl | H |
| 677 | 2,4-$(CH_3)_2$, 6-F | Cl | H |
| 678 | 2,4-$(CH_3)_2$, 6-Cl | Cl | H |
| 679 | 2,4-$(CH_3)_2$, 6-Br | Cl | H |
| 680 | 2-i-$CH_3H_{11}$, 4-Cl, 5-$CH_3$ | Cl | H |
| 681 | 2-Cl, 4-$NO_2$ | Cl | H |
| 682 | 2-$NO_2$, 4-Cl | Cl | H |
| 683 | 2-$OCH_3$, 5-$NO_2$ | Cl | H |
| 684 | 2,4-$Cl_2$, 5-$NO_2$ | Cl | H |
| 685 | 2,4-$Cl_2$, 6-$NO_2$ | Cl | H |
| 686 | 2,6-$Cl_2$, 4-$NO_2$ | Cl | H |
| 687 | 2,6-$Br_2$, 4-$NO_2$ | Cl | H |
| 688 | 2,6-$I_2$, 4-$NO_2$ | Cl | H |
| 689 | 2-$CH_3$, 5-i-$C_3H_7$, 4-Cl | Cl | H |
| 690 | 2-$CO_2CH_3$ | Cl | H |
| 691 | 3-$CO_2CH_3$ | Cl | H |
| 692 | 4-$CO_2CH_3$ | Cl | H |
| 693 | 2-$CH_2$—$OCH_3$ | Cl | H |
| 694 | 3-$CH_2$—$OCH_3$ | Cl | H |
| 695 | 4-$CH_2$—$OCH_3$ | Cl | H |
| 696 | 2-Me-4-$CH_3$—$CH(CH_3)$—CO | Cl | H |
| 697 | 2-$CH_3$-4-($CH_3$—C=$NOCH_3$) | Cl | H |
| 698 | 2-$CH_3$-4-($CH_3$—C=$NOC_2H_5$) | Cl | H |
| 699 | 2-$CH_3$-4-($CH_3$—C=NO-n-$C_3H_7$) | Cl | H |
| 700 | 2-$CH_3$-4-($CH_3$—C=NO-i-$C_3H_7$) | Cl | H |
| 701 | 2,5-$(CH_3)_2$-4-($CH_3$—C=$NOCH_3$) | Cl | H |
| 702 | 2,5-$(CH_3)_2$-4-($CH_3$—C=$NOC_2H_5$) | Cl | H |
| 703 | 2,5-$(CH_3)_2$-4-($CH_3$—C=NO-n-$C_3H_7$) | Cl | H |
| 704 | 2,5-$(CH_3)_2$-4-($CH_3$—C=NO-i-$C_3H_7$) | Cl | H |
| 705 | 2-$C_6H_5$ | Cl | H |
| 706 | 3-$C_6H_5$ | Cl | H |
| 707 | 4-$C_6H_5$ | Cl | H |
| 708 | 2-(2'-F—$C_6H_4$) | Cl | H |
| 709 | 2-$CH_3$, 5-Br | Cl | H |
| 710 | 2-$CH_3$, 6-Br | Cl | H |
| 711 | 2-Cl, 3-$CH_3$ | Cl | H |
| 712 | 2-Cl, 4-$CH_3$ | Cl | H |
| 713 | 2-Cl, 5-$CH_3$ | Cl | H |
| 714 | 2-F, 3-$CH_3$ | Cl | H |
| 715 | 2-F, 4-$CH_3$ | Cl | H |
| 716 | 2-F, 5-$CH_3$ | Cl | H |
| 717 | 2-Br, 3-$CH_3$ | Cl | H |
| 716 | 2-Br, 4-$CH_3$ | Cl | H |
| 719 | 2-Br, 5-$CH_3$ | Cl | H |
| 720 | 3-$CH_3$, 4-Cl | Cl | H |
| 721 | 3-$CH_3$, 5-Cl | Cl | H |
| 722 | 3-$CH_3$, 4-F | Cl | H |
| 723 | 3-$CH_3$, 5-F | Cl | H |
| 724 | 3-$CH_3$, 4-Br | Cl | H |
| 725 | 3-$CH_3$, 5-Br | Cl | H |
| 726 | 3-F, 4-$CH_3$ | Cl | H |
| 727 | 3-Cl, 4-$CH_3$ | Cl | H |
| 728 | 3-Br, 4-$CH_3$ | Cl | H |
| 729 | 2-Cl, 4,5-$(CH_3)_2$ | Cl | H |
| 730 | 2-Br, 4,5-$(CH_3)_2$ | Cl | H |
| 731 | 2-Cl, 3,5-$(CH_3)_2$ | Cl | H |
| 732 | 2-Br, 3,5-$(CH_3)_2$ | Cl | H |
| 733 | 2,6-$Cl_2$, 4-$CH_3$ | Cl | H |
| 734 | 2,6-$F_2$, 4-$CH_3$ | Cl | H |
| 735 | 2,6-$Br_2$, 4-$CH_3$ | Cl | H |
| 736 | 2,4-$Br_2$, 6-$CH_3$ | Cl | H |
| 737 | 2,4-$F_2$, 6-$CH_3$ | Cl | H |
| 738 | 2,4-$Br_2$, 6-$CH_3$ | Cl | H |
| 739 | 2,6-$(CH_3)_2$, 4-F | Cl | H |
| 740 | 2,6-$(CH_3)_2$, 4-Cl | Cl | H |
| 741 | 2,6-$(CH_3)_2$, 4-Br | Cl | H |
| 742 | 3,5-$(CH_3)_2$, 4-F | Cl | H |
| 743 | 3,5-$(CH_3)_2$, 4-Cl | Cl | H |
| 744 | 3,5-$(CH_3)_2$, 4-Br | Cl | H |
| 745 | 2-$CF_3$ | Cl | H |
| 746 | 3-$CF_3$ | Cl | H |
| 747 | 4-$CF_3$ | Cl | H |
| 748 | 2-$OCF_3$ | Cl | H |
| 749 | 3-$OCF_3$ | Cl | H |
| 750 | 4-$OCF_3$ | Cl | H |
| 751 | 3-$OCH_2CHF_2$ | Cl | H |
| 752 | 2-$NO_2$ | Cl | H |
| 753 | 3-$NO_2$ | Cl | H |
| 754 | 4-$NO_2$ | Cl | H |
| 755 | 2-CN | Cl | H |
| 756 | 3-CN | Cl | H |
| 757 | 4-CN | Cl | H |
| 758 | 2-$CH_3$, 3-Cl | Cl | H |
| 759 | 2-$CH_3$, 4-Cl | Cl | H |
| 760 | 2-$CH_3$, 5-Cl | Cl | H |
| 761 | 2-$CH_3$, 6-Cl | Cl | H |
| 762 | 2-$CH_3$, 3-F | Cl | H |
| 763 | 2-$CH_3$, 4-F | Cl | H |
| 764 | 2-$CH_3$, 5-F | Cl | H |
| 765 | 2-$CH_3$, 6-F | Cl | H |
| 766 | 2-$CH_3$, 3-Br | Cl | H |
| 767 | 2-$CH_3$, 4-Br | Cl | H |
| 768 | 2-Pyridyl-2' | Cl | H |
| 769 | 3-Pyridyl-3' | Cl | H |
| 770 | 4-Pyridyl-4' | Cl | H |
| 771 | 2-CO—$CH_3$ | Cl | H |
| 772 | 3-CO—$CH_3$ | Cl | H |
| 773 | 4-CO—$CH_3$ | Cl | H |
| 774 | 2-C(=N—$OCH_3$)—$CH_3$ | Cl | H |
| 775 | 3-C(=N—$OCH_3$)—$CH_3$ | Cl | H |
| 776 | 4-C(=N—$OCH_3$)—$CH_3$ | Cl | H |
| 777 | 2-F | CN | H |
| 778 | 3-F | CN | H |
| 779 | 4-F | CN | H |
| 780 | 2,4-$F_2$ | CN | H |
| 781 | 2,4,6-$F_3$ | CN | H |
| 782 | 2,3,4,5,6-$F_5$ | CN | H |
| 783 | 2,3-$F_2$ | CN | H |
| 784 | 2-Cl | CN | H |
| 785 | 3-Cl | CN | H |
| 786 | 4-Cl | CN | H |

TABLE A-continued

| Number | $R_m$ | $R^2$ | $R^1_n$ |
|---|---|---|---|
| 787 | 2,3-Cl$_2$ | CN | H |
| 788 | 2,4-Cl$_2$ | CN | H |
| 789 | 2,5-Cl$_2$ | CN | H |
| 790 | 2,6-Cl$_2$ | CN | H |
| 791 | 3,4-Cl$_2$ | CN | H |
| 792 | 3,5-Cl$_2$ | CN | H |
| 793 | 2,3,4-Cl$_3$ | CN | H |
| 794 | 2,3,5-Cl$_3$ | CN | H |
| 795 | 2,3,6-Cl$_3$ | CN | H |
| 796 | 2,4,5-Cl$_3$ | CN | H |
| 797 | 2,4,6-Cl$_3$ | CN | H |
| 798 | 3,4,5-Cl$_3$ | CN | H |
| 799 | 2,3,4,6-Cl$_4$ | CN | H |
| 800 | 2,3,5,6-Cl$_4$ | CN | H |
| 801 | 2,3,4,5,6-Cl$_5$ | CN | H |
| 802 | 2-Br | CN | H |
| 803 | 3-Br | CN | H |
| 804 | 4-Br | CN | H |
| 805 | 2,4-Br$_2$ | CN | H |
| 806 | 2,5-Br$_2$ | CN | H |
| 807 | 2,6-Br$_2$ | CN | H |
| 808 | 2,4,6-Br$_3$ | CN | H |
| 809 | 2,3,4,5,6-Br$_5$ | CN | H |
| 810 | 2-I | CN | H |
| 811 | 3-I | CN | H |
| 812 | 4-I | CN | H |
| 813 | 2,4-I$_2$ | CN | H |
| 814 | 2-Cl, 3-F | CN | H |
| 815 | 2-Cl, 4-F | CN | H |
| 816 | 2-Cl, 5-F | CN | H |
| 817 | 2-Cl, 6-F | CN | H |
| 818 | 2-Cl, 3-Br | CN | H |
| 819 | 2-Cl, 4-Br | CN | H |
| 820 | 2-Cl, 5-Br | CN | H |
| 821 | 2-Cl, 6-Br | CN | H |
| 822 | 2-Br, 3-Cl | CN | H |
| 823 | 2-Br, 4-Cl | CN | H |
| 824 | 2-Br, 5-Cl | CN | H |
| 625 | 2-Br, 3-F | CN | H |
| 826 | 2-Br, 4-F | CN | H |
| 827 | 2-Br, 5-F | CN | H |
| 828 | 2-Br, 6-F | CN | H |
| 829 | 2-F, 3-Cl | CN | H |
| 830 | 2-F, 4-Cl | CN | H |
| 831 | 2-F, 5-Cl | CN | H |
| 832 | 3-Cl, 4-F | CN | H |
| 833 | 3-Cl, 5-F | CN | H |
| 834 | 3-Cl, 4-Br | CN | H |
| 835 | 3-Cl, 5-Br | CN | H |
| 836 | 3-F, 4-Cl | CN | H |
| 837 | 3-F, 4-Br | CN | H |
| 838 | 3-Br, 4-Cl | CN | H |
| 839 | 3-Br, 4-F | CN | H |
| 840 | 2,6-Cl$_2$, 4-Br | CN | H |
| 841 | 2-CH$_3$ | CN | H |
| 842 | 3-CH$_3$ | CN | H |
| 843 | 4-CH$_3$ | CN | H |
| 844 | 2,3-(CH$_3$)$_2$ | CN | H |
| 845 | 2,4-(CH$_3$)$_2$ | CN | H |
| 846 | 2,5-(CH$_3$)$_2$ | CN | H |
| 847 | 2,6-(CH$_3$)$_2$ | CN | H |
| 848 | 3,4-(CH$_3$)$_2$ | CN | H |
| 849 | 3,5-(CH$_3$)$_2$ | CN | H |
| 850 | 2,3,5-(CH$_3$)$_3$ | CN | H |
| 851 | 2,3,4-(CH$_3$)$_3$ | CN | H |
| 852 | 2,3,6-(CH$_3$)$_3$ | CN | H |
| 853 | 2,4,5-(CH$_3$)$_3$ | CN | H |
| 854 | 2,4,6-(CH$_3$)$_3$ | CN | H |
| 855 | 3,4,5-(CH$_3$)$_3$ | CN | H |
| 856 | 2,3,4,6-(CH$_3$)$_4$ | CN | H |
| 857 | 2,3,5,6-(CH$_3$)$_4$ | CN | H |
| 858 | 2,3,4,5,6-(CH$_3$)$_5$ | CN | H |
| 859 | 2-C$_2$H$_5$ | CN | H |
| 860 | 3-C$_2$H$_5$ | CN | H |
| 861 | 4-C$_2$H$_5$ | CN | H |
| 862 | 2,4-(C$_2$H$_5$)$_2$ | CN | H |
| 863 | 2,6-(C$_2$H$_5$)$_2$ | CN | H |
| 864 | 3,5-(C$_2$H$_5$)$_2$ | CN | H |
| 865 | 2,4,6-(C$_2$H$_5$)$_3$ | CN | H |
| 866 | 2-n-C$_3$H$_7$ | CN | H |
| 867 | 3-n-C$_3$H$_7$ | CN | H |
| 868 | 4-n-C$_3$H$_7$ | CN | H |
| 869 | 2-i-C$_3$H$_7$ | CN | H |
| 870 | 3-i-C$_3$H$_7$ | CN | H |
| 871 | 4-i-C$_3$H$_7$ | CN | H |
| 872 | 2,4-(i-C$_3$H$_7$)$_2$ | CN | H |
| 873 | 2,6-(i-C$_3$H$_7$)$_2$ | CN | H |
| 874 | 3,5-(i-C$_3$H$_7$)$_2$ | CN | H |
| 875 | 2-s-C$_4$H$_9$ | CN | H |
| 876 | 3-s-C$_4$H$_9$ | CN | H |
| 877 | 4-s-C$_4$H$_9$ | CN | H |
| 878 | 2-t-C$_4$H$_9$ | CN | H |
| 879 | 3-t-C$_4$H$_9$ | CN | H |
| 880 | 4-t-C$_4$H$_9$ | CN | H |
| 881 | 4-n-C$_9$H$_{19}$ | CN | H |
| 882 | 2-CH$_3$, 4-t-C$_4$H$_9$ | CN | H |
| 883 | 2-CH$_3$, 6-t-C$_4$H$_9$ | CN | H |
| 884 | 2-CH$_3$, 4-i-C$_3$H$_7$ | CN | H |
| 885 | 2-CH$_3$, 5-i-C$_3$H$_7$ | CN | H |
| 886 | 3-CH$_3$, 4-i-C$_3$H$_7$ | CN | H |
| 887 | 2-cyclo-C$_6$H$_{11}$ | CN | H |
| 888 | 3-cyclo-C$_6$H$_{11}$ | CN | H |
| 889 | 4-cyclo-C$_6$H$_{11}$ | CN | H |
| 890 | 2-Cl, 4-C$_6$H$_5$ | CN | H |
| 891 | 2-Br, 4-C$_6$H$_5$ | CN | H |
| 892 | 2-OCH$_3$ | CN | H |
| 893 | 3-OCH$_3$ | CN | H |
| 894 | 4-OCH$_3$ | CN | H |
| 895 | 2-OC$_2$H$_5$ | CN | H |
| 896 | 3-O—C$_2$H$_5$ | CN | H |
| 897 | 4-O—C$_2$H$_5$ | CN | H |
| 898 | 2-O-n-C$_3$H$_7$ | CN | H |
| 899 | 3-O-n-C$_3$H$_7$ | CN | H |
| 900 | 4-O-n-C$_3$H$_7$ | CN | H |
| 901 | 2-O-i-C$_3$H$_7$ | CN | H |
| 902 | 3-O-i-C$_3$H$_7$ | CN | H |
| 903 | 4-O-i-C$_3$H$_7$ | CN | H |
| 904 | 2-O-n-C$_6$H$_{13}$ | CN | H |
| 905 | 3-O-n-C$_6$H$_{13}$ | CN | H |
| 906 | 4-O-n-C$_6$H$_{13}$ | CN | H |
| 907 | 2-O—CH$_2$C$_6$H$_5$ | CN | H |
| 908 | 3-O—CH$_2$C$_6$H$_5$ | CN | H |
| 909 | 4-O—CH$_2$C$_6$H$_5$ | CN | H |
| 910 | 2-O—(CH$_2$)$_3$C$_6$H$_5$ | CN | H |
| 911 | 4-O—(CH$_2$)$_3$C$_6$H$_5$ | CN | H |
| 912 | 2,3-(OCH$_3$)$_2$ | CN | H |
| 913 | 2,4-(OCH$_3$)$_2$ | CN | H |
| 914 | 2,5-(OCH$_3$)$_2$ | CN | H |
| 915 | 2,6-(OCH$_3$)$_2$ | CN | H |
| 916 | 3,4-(OCH$_3$)$_2$ | CN | H |
| 917 | 3,5-(OCH$_3$)$_2$ | CN | H |
| 918 | 2-O-t-C$_4$H$_9$ | CN | H |
| 919 | 3-O-t-C$_4$H$_9$ | CN | H |
| 920 | 4-O-t-C$_4$H$_9$ | CN | H |
| 921 | 3-(3'-Cl—C$_6$H$_4$) | CN | H |
| 922 | 4-(4'-CH$_3$—C$_6$H$_4$) | CN | H |
| 923 | 2-O—C$_6$H$_5$ | CN | H |
| 924 | 3-O—C$_6$H$_5$ | CN | H |
| 925 | 4-O—C$_6$H$_5$ | CN | H |
| 926 | 2-O-(2'-F—C$_6$H$_4$) | CN | H |
| 927 | 3-O-(3'-Cl—C$_6$H$_4$) | CN | H |
| 928 | 4-O-(4'-CH$_3$—C$_6$H$_4$) | CN | H |
| 929 | 2,3,6-(CH$_3$)$_3$, 4-F | CN | H |
| 930 | 2,3,6-(CH$_3$)$_3$, 4-Cl | CN | H |
| 931 | 2,3,6-(CH$_3$)$_3$, 4-Br | CN | H |
| 932 | 2,4-(CH$_3$)$_2$, 6-F | CN | H |
| 933 | 2,4-(CH$_3$)$_2$, 6-Cl | CN | H |
| 934 | 2,4-(CH$_3$)$_2$, 6-Br | CN | H |
| 935 | 2-i-CH$_3$H$_{11}$, 4-Cl, 5-CH$_3$ | CN | H |
| 936 | 2-Cl, 4-NO$_2$ | CN | H |
| 937 | 2-NO$_2$, 4-Cl | CN | H |
| 938 | 2-OCH$_3$, 5-NO$_2$ | CN | H |
| 939 | 2,4-Cl$_2$, 5-NO$_2$ | CN | H |
| 940 | 2,4-Cl$_2$, 6-NO$_2$ | CN | H |

TABLE A-continued

| Number | R$_m$ | R$^2$ | R$^1_n$ |
|---|---|---|---|
| 941 | 2,6-Cl$_2$, 4-NO$_2$ | CN | H |
| 942 | 2,6-Br$_2$, 4-NO$_2$ | CN | H |
| 943 | 2,6-I$_2$, 4-NO$_2$ | CN | H |
| 944 | 2-CH$_3$, 5-i-CH$_3$H$_7$, 4-Cl | CN | H |
| 945 | 2-CO$_2$CH$_3$ | CN | H |
| 946 | 3-CO$_2$CH$_3$ | CN | H |
| 947 | 4-CO$_2$CH$_3$ | CN | H |
| 948 | 2-CH$_2$—OCH$_3$ | CN | H |
| 949 | 3-CH$_2$—OCH$_3$ | CN | H |
| 950 | 4-CH$_2$—OCH$_3$ | CN | H |
| 951 | 2-Me-4-CH$_3$—CH(CH$_3$)—CO | CN | H |
| 952 | 2-CH$_3$-4-(CH$_3$—C=NOCH$_3$) | CN | H |
| 953 | 2-CH$_3$-4-(CH$_3$—C=NOC$_2$H$_5$) | CN | H |
| 954 | 2-CH$_3$-4-(CH$_3$—C=NO-n-C$_3$H$_7$) | CN | H |
| 955 | 2-CH$_3$-4-(CH$_3$—C=NO-i-C$_3$H$_7$) | CN | H |
| 956 | 2,5-(CH$_3$)$_2$-4-(CH$_3$—C=NOCH$_3$) | CN | H |
| 957 | 2,5-(CH$_3$)$_2$-4-(CH$_3$—C=NOC$_2$H$_5$) | CN | H |
| 958 | 2,5-CH$_3$-4-(CH$_3$—C=NO-n-C$_3$H$_7$) | CN | H |
| 959 | 2,5-(CH$_3$)$_2$-4-(CH$_3$—C=NO-i-C$_3$H$_7$) | CN | H |
| 960 | 2-C$_6$H$_5$ | CN | H |
| 961 | 3-C$_6$H$_5$ | CN | H |
| 962 | 4-C$_6$H$_5$ | CN | H |
| 963 | 2-(2'-F—C$_6$H$_4$) | CN | H |
| 964 | 2-CH$_3$, 5-Br | CN | H |
| 965 | 2-CH$_3$, 6-Br | CN | H |
| 966 | 2-Cl, 3-CH$_3$ | CN | H |
| 967 | 2-Cl, 4-CH$_3$ | CN | H |
| 968 | 2-Cl, 5-CH$_3$ | CN | H |
| 969 | 2-F, 3-CH$_3$ | CN | H |
| 970 | 2-F, 4-CH$_3$ | CN | H |
| 971 | 2-F, 5-CH$_3$ | CN | H |
| 972 | 2-Br, 3-CH$_3$ | CN | H |
| 973 | 2-Br, 4-CH$_3$ | CN | H |
| 974 | 2-Br, 5-CH$_3$ | CN | H |
| 975 | 3-CH$_3$, 4-Cl | CN | H |
| 976 | 3-CH$_3$, 5-Cl | CN | H |
| 977 | 3-CH$_3$, 4-F | CN | H |
| 978 | 3-CH$_3$, 5-F | CN | H |
| 979 | 3-CH$_3$, 4-Br | CN | H |
| 980 | 3-CH$_3$, 5-Br | CN | H |
| 981 | 3-F, 4-CH$_3$ | CN | H |
| 982 | 3-Cl, 4-CH$_3$ | CN | H |
| 983 | 3-Br, 4-CH$_3$ | CN | H |
| 984 | 2-Cl, 4,5-(CH$_3$)$_2$ | CN | H |
| 985 | 2-Br, 4,5-(CH$_3$)$_2$ | CN | H |
| 986 | 2-Cl, 3,5-(CH$_3$)$_2$ | CN | H |
| 987 | 2-Br, 3,5-(CH$_3$)$_2$ | CN | H |
| 988 | 2,6-Cl$_2$, 4-CH$_3$ | CN | H |
| 989 | 2,6-F$_2$, 4-CH$_3$ | CN | H |
| 990 | 2,6-Br$_2$, 4-CH$_3$ | CN | H |
| 991 | 2,4-Br$_2$, 6-CH$_3$ | CN | H |
| 992 | 2,4-F$_2$, 6-CH$_3$ | CN | H |
| 993 | 2,4-Br$_2$, 6-CH$_3$ | CN | H |
| 994 | 2,6-(CH$_3$)$_2$, 4-F | CN | H |
| 995 | 2,6-(CH$_3$)$_2$, 4-Cl | CN | H |
| 996 | 2,6-(CH$_3$)$_2$, 4-Br | CN | H |
| 997 | 3,5-(CH$_3$)$_2$, 4-F | CN | H |
| 998 | 3,5-(CH$_3$)$_2$, 4-Cl | CN | H |
| 999 | 3,5-(CH$_3$)$_2$, 4-Br | CN | H |
| 1000 | 2-CF$_3$ | CN | H |
| 1001 | 3-CF$_3$ | CN | H |
| 1002 | 4-CF$_3$ | CN | H |
| 1003 | 2-OCF$_3$ | CN | H |
| 1004 | 3-OCF$_3$ | CN | H |
| 1005 | 4-OCF$_3$ | CN | H |
| 1006 | 3-OCH$_2$CHF$_2$ | CN | H |
| 1007 | 2-NO$_2$ | CN | H |
| 1008 | 3-NO$_2$ | CN | H |
| 1009 | 4-NO$_2$ | CN | H |
| 1010 | 2-CN | CN | H |
| 1011 | 3-CN | CN | H |
| 1012 | 4-CN | CN | H |
| 1013 | 2-CH$_3$, 3-Cl | CN | H |
| 1014 | 2-CH$_3$, 4-Cl | CN | H |
| 1015 | 2-CH$_3$, 5-Cl | CN | H |
| 1016 | 2-CH$_3$, 6-Cl | CN | H |
| 1017 | 2-CH$_3$, 3-F | CN | H |
| 1018 | 2-CH$_3$, 4-F | CN | H |
| 1019 | 2-CH$_3$, 5-F | CN | H |
| 1020 | 2-CH$_3$, 6-F | CN | H |
| 1021 | 2-CH$_3$, 3-Br | CN | H |
| 1022 | 2-CH$_3$, 4-Br | CN | H |
| 1023 | 2-Pyridyl-2' | CN | H |
| 1024 | 3-Pyridyl-3' | CN | H |
| 1025 | 4-Pyridyl-4' | CN | H |
| 1026 | 2-CO—CH$_3$ | CN | H |
| 1027 | 3-CO—CH$_3$ | CN | H |
| 1028 | 4-CO—CH$_3$ | CN | H |
| 1029 | 2-C(=N—OCH$_3$)—CH$_3$ | CN | H |
| 1030 | 3-C(=N—OCH$_3$)—CH$_3$ | CN | H |
| 1031 | 4-C(=N—OCH$_3$)—CH$_3$ | CN | H |
| 1032 | 2-F | OCH$_3$ | H |
| 1033 | 3-F | OCH$_3$ | H |
| 1034 | 4-F | OCH$_3$ | H |
| 1035 | 2,4-F$_2$ | OCH$_3$ | H |
| 1036 | 2,4,6-F$_3$ | OCH$_3$ | H |
| 1037 | 2,3,4,5,6-F$_5$ | OCH$_3$ | H |
| 1038 | 2,3-F$_2$ | OCH$_3$ | H |
| 1039 | 2-Cl | OCH$_3$ | H |
| 1040 | 3-Cl | OCH$_3$ | H |
| 1041 | 4-Cl | OCH$_3$ | H |
| 1042 | 2,3-Cl$_2$ | OCH$_3$ | H |
| 1043 | 2,4-Cl$_2$ | OCH$_3$ | H |
| 1044 | 2,5-Cl$_2$ | OCH$_3$ | H |
| 1045 | 2,6-Cl$_2$ | OCH$_3$ | H |
| 1046 | 3,4-Cl$_2$ | OCH$_3$ | H |
| 1047 | 3,5-Cl$_2$ | OCH$_3$ | H |
| 1048 | 2,3,4-Cl$_3$ | OCH$_3$ | H |
| 1049 | 2,3,5-Cl$_3$ | OCH$_3$ | H |
| 1050 | 2,3,6-Cl$_3$ | OCH$_3$ | H |
| 1051 | 2,4,5-Cl$_3$ | OCH$_3$ | H |
| 1052 | 2,4,6-Cl$_3$ | OCH$_3$ | H |
| 1053 | 3,4,5-Cl$_3$ | OCH$_3$ | H |
| 1054 | 2,3,4,6-Cl$_4$ | OCH$_3$ | H |
| 1055 | 2,3,5,6-Cl$_4$ | OCH$_3$ | H |
| 1056 | 2,3,4,5,6-Cl$_5$ | OCH$_3$ | H |
| 1057 | 2-Br | OCH$_3$ | H |
| 1058 | 3-Br | OCH$_3$ | H |
| 1059 | 4-Br | OCH$_3$ | H |
| 1060 | 2,4-Br$_2$ | OCH$_3$ | H |
| 1061 | 2,5-Br$_2$ | OCH$_3$ | H |
| 1062 | 2,6-Br$_2$ | OCH$_3$ | H |
| 1063 | 2,4,6-Br$_3$ | OCH$_3$ | H |
| 1064 | 2,3,4,5,6-Br$_5$ | OCH$_3$ | H |
| 1065 | 2-I | OCH$_3$ | H |
| 1066 | 3-I | OCH$_3$ | H |
| 1067 | 4-I | OCH$_3$ | H |
| 1068 | 2,4-I$_2$ | OCH$_3$ | H |
| 1069 | 2-Cl, 3-F | OCH$_3$ | H |
| 1070 | 2-Cl, 4-F | OCH$_3$ | H |
| 1071 | 2-Cl, 5-F | OCH$_3$ | H |
| 1072 | 2-Cl, 6-F | OCH$_3$ | H |
| 1073 | 2-Cl, 3-Br | OCH$_3$ | H |
| 1074 | 2-Cl, 4-Br | OCH$_3$ | H |
| 1075 | 2-Cl, 5-Br | OCH$_3$ | H |
| 1076 | 2-Cl, 6-Br | OCH$_3$ | H |
| 1077 | 2-Br, 3-Cl | OCH$_3$ | H |
| 1078 | 2-Br, 4-Cl | OCH$_3$ | H |
| 1079 | 2-Br, 5-Cl | OCH$_3$ | H |
| 1080 | 2-Br, 3-F | OCH$_3$ | H |
| 1081 | 2-Br, 4-F | OCH$_3$ | H |
| 1082 | 2-Br, 5-F | OCH$_3$ | H |
| 1083 | 2-Br, 6-F | OCH$_3$ | H |
| 1084 | 2-F, 3-Cl | OCH$_3$ | H |
| 1085 | 2-F, 4-Cl | OCH$_3$ | H |
| 1086 | 2-F, 5-Cl | OCH$_3$ | H |
| 1087 | 3-Cl, 4-F | OCH$_3$ | H |
| 1088 | 3-Cl, 5-F | OCH$_3$ | H |
| 1089 | 3-Cl, 4-Br | OCH$_3$ | H |
| 1090 | 3-Cl, 5-Br | OCH$_3$ | H |
| 1091 | 3-F, 4-Cl | OCH$_3$ | H |
| 1092 | 3-F, 4-Br | OCH$_3$ | H |
| 1093 | 3-Br, 4-Cl | OCH$_3$ | H |
| 1094 | 3-Br, 4-F | OCH$_3$ | H |

TABLE A-continued

| Number | $R_m$ | $R^2$ | $R^1_n$ |
|---|---|---|---|
| 1095 | 2,6-Cl$_2$, 4-Br | OCH$_3$ | H |
| 1096 | 2-CH$_3$ | OCH$_3$ | H |
| 1097 | 3-CH$_3$ | OCH$_3$ | H |
| 1098 | 4-CH$_3$ | OCH$_3$ | H |
| 1099 | 2,3-(CH$_3$)$_2$ | OCH$_3$ | H |
| 1100 | 2,4-(CH$_3$)$_2$ | OCH$_3$ | H |
| 1101 | 2,5-(CH$_3$)$_2$ | OCH$_3$ | H |
| 1102 | 2,6-(CH$_3$)$_2$ | OCH$_3$ | H |
| 1103 | 3,4-(CH$_3$)$_2$ | OCH$_3$ | H |
| 1104 | 3,5-(CH$_3$)$_2$ | OCH$_3$ | H |
| 1105 | 2,3,5-(CH$_3$)$_3$ | OCH$_3$ | H |
| 1106 | 2,3,4-(CH$_3$)$_3$ | OCH$_3$ | H |
| 1107 | 2,3,6-(CH$_3$)$_3$ | OCH$_3$ | H |
| 1108 | 2,4,5-(CH$_3$)$_3$ | OCH$_3$ | H |
| 1109 | 2,4,6-(CH$_3$)$_3$ | OCH$_3$ | H |
| 1110 | 3,4,5-(CH$_3$)$_3$ | OCH$_3$ | H |
| 1111 | 2,3,4,6-(CH$_3$)$_4$ | OCH$_3$ | H |
| 1112 | 2,3,5,6-(CH$_3$)$_4$ | OCH$_3$ | H |
| 1113 | 2,3,4,5,6-(CH$_3$)$_5$ | OCH$_3$ | H |
| 1114 | 2-C$_2$H$_5$ | OCH$_3$ | H |
| 1115 | 3-C$_2$H$_5$ | OCH$_3$ | H |
| 1116 | 4-C$_2$H$_5$ | OCH$_3$ | H |
| 1117 | 2,4-(C$_2$H$_5$)$_2$ | OCH$_3$ | H |
| 1118 | 2,6-(C$_2$H$_5$)$_2$ | OCH$_3$ | H |
| 1119 | 3,5-(C$_2$H$_5$)$_2$ | OCH$_3$ | H |
| 1120 | 2,4,6-(C$_2$H$_5$)$_3$ | OCH$_3$ | H |
| 1121 | 2-n-C$_3$H$_7$ | OCH$_3$ | H |
| 1122 | 3-n-C$_3$H$_7$ | OCH$_3$ | H |
| 1123 | 4-n-C$_3$H$_7$ | OCH$_3$ | H |
| 1124 | 2-i-C$_3$H$_7$ | OCH$_3$ | H |
| 1125 | 3-i-C$_3$H$_7$ | OCH$_3$ | H |
| 1126 | 4-i-C$_3$H$_7$ | OCH$_3$ | H |
| 1127 | 2,4-(i-C$_3$H$_7$)$_2$ | OCH$_3$ | H |
| 1128 | 2,6-(i-C$_3$H$_7$)$_2$ | OCH$_3$ | H |
| 1129 | 3,5-(i-C$_3$H$_7$)$_2$ | OCH$_3$ | H |
| 1130 | 2-s-C$_4$H$_9$ | OCH$_3$ | H |
| 1131 | 3-s-C$_4$H$_9$ | OCH$_3$ | H |
| 1132 | 4-s-C$_4$H$_9$ | OCH$_3$ | H |
| 1133 | 2-t-C$_4$H$_9$ | OCH$_3$ | H |
| 1134 | 3-t-C$_4$H$_9$ | OCH$_3$ | H |
| 1135 | 4-t-C$_4$H$_9$ | OCH$_3$ | H |
| 1136 | 4-n-C$_9$H$_{19}$ | OCH$_3$ | H |
| 1137 | 2-CH$_3$, 4-t-C$_4$H$_9$ | OCH$_3$ | H |
| 1138 | 2-CH$_3$, 6-t-C$_4$H$_9$ | OCH$_3$ | H |
| 1139 | 2-CH$_3$, 4-i-C$_3$H$_7$ | OCH$_3$ | H |
| 1140 | 2-CH$_3$, 5-i-C$_3$H$_7$ | OCH$_3$ | H |
| 1141 | 3-CH$_3$, 4-i-C$_3$H$_7$ | OCH$_3$ | H |
| 1142 | 2-cyclo-C$_6$H$_{11}$ | OCH$_3$ | H |
| 1143 | 3-cyclo-C$_6$H$_{11}$ | OCH$_3$ | H |
| 1144 | 4-cyclo-C$_6$H$_{11}$ | OCH$_3$ | H |
| 1145 | 2-Cl, 4-C$_6$H$_5$ | OCH$_3$ | H |
| 1146 | 2-Br, 4-C$_6$H$_5$ | OCH$_3$ | H |
| 1147 | 2-OCH$_3$ | OCH$_3$ | H |
| 1148 | 3-OCH$_3$ | OCH$_3$ | H |
| 1149 | 4-OCH$_3$ | OCH$_3$ | H |
| 1150 | 2-OC$_2$H$_5$ | OCH$_3$ | H |
| 1151 | 3-O—C$_2$H$_5$ | OCH$_3$ | H |
| 1152 | 4-O—C$_2$H$_5$ | OCH$_3$ | H |
| 1153 | 2-O-n-C$_3$H$_7$ | OCH$_3$ | H |
| 1154 | 3-O-n-C$_3$H$_7$ | OCH$_3$ | H |
| 1155 | 4-O-n-C$_3$H$_7$ | OCH$_3$ | H |
| 1156 | 2-O-i-C$_3$H$_7$ | OCH$_3$ | H |
| 1157 | 3-O-i-C$_3$H$_7$ | OCH$_3$ | H |
| 1158 | 4-O-i-C$_3$H$_7$ | OCH$_3$ | H |
| 1159 | 2-O-n-C$_6$H$_{13}$ | OCH$_3$ | H |
| 1160 | 3-O-n-C$_6$H$_{13}$ | OCH$_3$ | H |
| 1161 | 4-O-n-C$_6$H$_{13}$ | OCH$_3$ | H |
| 1162 | 2-O—CH$_2$C$_6$H$_5$ | OCH$_3$ | H |
| 1163 | 3-O—CH$_2$C$_6$H$_5$ | OCH$_3$ | H |
| 1164 | 4-O—CH$_2$C$_6$H$_5$ | OCH$_3$ | H |
| 1165 | 2-O—(CH$_2$)$_3$C$_6$H$_5$ | OCH$_3$ | H |
| 1166 | 4-O—(CH$_2$)$_3$C$_6$H$_5$ | OCH$_3$ | H |
| 1167 | 2,3-(OCH$_3$)$_2$ | OCH$_3$ | H |
| 1168 | 2,4-(OCH$_3$)$_2$ | OCH$_3$ | H |
| 1169 | 2,5-(OCH$_3$)$_2$ | OCH$_3$ | H |
| 1170 | 2,6-(OCH$_3$)$_2$ | OCH$_3$ | H |
| 1171 | 3,4-(OCH$_3$)$_2$ | OCH$_3$ | H |
| 1172 | 3,5-(OCH$_3$)$_2$ | OCH$_3$ | H |
| 1173 | 2-O-t-C$_4$H$_9$ | OCH$_3$ | H |
| 1174 | 3-O-t-C$_4$H$_9$ | OCH$_3$ | H |
| 1175 | 4-O-t-C$_4$H$_9$ | OCH$_3$ | H |
| 1176 | 3-(3'-Cl—C$_6$H$_4$) | OCH$_3$ | H |
| 1177 | 4-(4'-CH$_3$—C$_6$H$_4$) | OCH$_3$ | H |
| 1178 | 2-O—C$_6$H$_5$ | OCH$_3$ | H |
| 1179 | 3-O—C$_6$H$_5$ | OCH$_3$ | H |
| 1180 | 4-O—C$_6$H$_5$ | OCH$_3$ | H |
| 1181 | 2-O-(2'-F—C$_6$H$_4$) | OCH$_3$ | H |
| 1182 | 3-O-(3'-Cl—C$_6$H$_4$) | OCH$_3$ | H |
| 1183 | 4-O-(4'-CH$_3$—C$_6$H$_4$) | OCH$_3$ | H |
| 1184 | 2,3,6-(CH$_3$)$_3$, 4-F | OCH$_3$ | H |
| 1185 | 2,3,6-(CH$_3$)$_3$, 4-Cl | OCH$_3$ | H |
| 1186 | 2,3,6-(CH$_3$)$_3$, 4-Br | OCH$_3$ | H |
| 1187 | 2,4-(CH$_3$)$_2$, 6-F | OCH$_3$ | H |
| 1188 | 2,4-(CH$_3$)$_2$, 6-Cl | OCH$_3$ | H |
| 1189 | 2,4-(CH$_3$)$_2$, 6-Br | OCH$_3$ | H |
| 1190 | 2-i-CH$_3$H$_1$, 4-Cl, 5-CH$_3$ | OCH$_3$ | H |
| 1191 | 2-Cl, 4-NO$_2$ | OCH$_3$ | H |
| 1192 | 2-NO$_2$, 4-Cl | OCH$_3$ | H |
| 1193 | 2-OCH$_3$, 5-NO$_2$ | OCH$_3$ | H |
| 1194 | 2,4-Cl$_2$, 5-NO$_2$ | OCH$_3$ | H |
| 1195 | 2,4-Cl$_2$, 6-NO$_2$ | OCH$_3$ | H |
| 1196 | 2,6-Cl$_2$, 4-NO$_2$ | OCH$_3$ | H |
| 1197 | 2,6-Br$_2$, 4-NO$_2$ | OCH$_3$ | H |
| 1198 | 2,6-I$_2$, 4-NO$_2$ | OCH$_3$ | H |
| 1199 | 2-CH$_3$, 5-i-C$_3$H$_7$, 4-Cl | OCH$_3$ | H |
| 1200 | 2-CO$_2$CH$_3$ | OCH$_3$ | H |
| 1201 | 3-CO$_2$CH$_3$ | OCH$_3$ | H |
| 1202 | 4-CO$_2$CH$_3$ | OCH$_3$ | H |
| 1203 | 2-CH$_2$—OCH$_3$ | OCH$_3$ | H |
| 1204 | 3-CH$_2$—OCH$_3$ | OCH$_3$ | H |
| 1205 | 4-CH$_2$—OCH$_3$ | OCH$_3$ | H |
| 1206 | 2-Me-4-CH$_3$—CH(CH$_3$)—CO | OCH$_3$ | H |
| 1207 | 2-CH$_3$-4-(CH$_3$—C=NOCH$_3$) | OCH$_3$ | H |
| 1208 | 2-CH$_3$-4-(CH$_3$—C=NOC$_2$H$_5$) | OCH$_3$ | H |
| 1209 | 2-CH$_3$-4-(CH$_3$—C=NO-n-C$_3$H$_7$) | OCH$_3$ | H |
| 1210 | 2-CH$_3$-4-(CH$_3$—C=NO-i-C$_3$H$_7$) | OCH$_3$ | H |
| 1211 | 2,5-(CH$_3$)2-4-(CH$_3$—C=NOCH$_3$) | OCH$_3$ | H |
| 1212 | 2,5-(CH$_3$)2-4-(CH$_3$—C=NOC$_2$H$_5$) | OCH$_3$ | H |
| 1213 | 2,5-(CH$_3$)$_2$-4-(CH$_3$—C=NO-n-C$_3$H$_7$) | OCH$_3$ | H |
| 1214 | 2,5-(CH$_3$)$_2$-4-(CH$_3$—C=NO-i-C$_3$H$_7$) | OCH$_3$ | H |
| 1215 | 2-C$_6$H$_5$ | OCH$_3$ | H |
| 1216 | 3-C$_6$H$_5$ | OCH$_3$ | H |
| 1217 | 4-C$_6$H$_5$ | OCH$_3$ | H |
| 1218 | 2-(2'-F—C$_6$H$_4$) | OCH$_3$ | H |
| 1219 | 2-CH$_3$, 5-Br | OCH$_3$ | H |
| 1220 | 2-CH$_3$, 6-Br | OCH$_3$ | H |
| 1221 | 2-Cl, 3-CH$_3$ | OCH$_3$ | H |
| 1222 | 2-Cl, 4-CH$_3$ | OCH$_3$ | H |
| 1223 | 2-Cl, 5-CH$_3$ | OCH$_3$ | H |
| 1224 | 2-F, 3-CH$_3$ | OCH$_3$ | H |
| 1225 | 2-F, 4-CH$_3$ | OCH$_3$ | H |
| 1226 | 2-F, 5-CH$_3$ | OCH$_3$ | H |
| 1227 | 2-Br, 3-CH$_3$ | OCH$_3$ | H |
| 1228 | 2-Br, 4-CH$_3$ | OCH$_3$ | H |
| 1229 | 2-Br, 5-CH$_3$ | OCH$_3$ | H |
| 1230 | 3-CH$_3$, 4-Cl | OCH$_3$ | H |
| 1231 | 3-CH$_3$, 5-Cl | OCH$_3$ | H |
| 1232 | 3-CH$_3$, 4-F | OCH$_3$ | H |
| 1233 | 3-CH$_3$, 5-F | OCH$_3$ | H |
| 1234 | 3-CH$_3$, 4-Br | OCH$_3$ | H |
| 1235 | 3-CH$_3$, 5-Br | OCH$_3$ | H |
| 1236 | 3-F, 4-CH$_3$ | OCH$_3$ | H |
| 1237 | 3-Cl, 4-CH$_3$ | OCH$_3$ | H |
| 1238 | 3-Br, 4-CH$_3$ | OCH$_3$ | H |
| 1239 | 2-Cl, 4,5-(CH$_3$)$_2$ | OCH$_3$ | H |
| 1240 | 2-Br, 4,5-(CH$_3$)$_2$ | OCH$_3$ | H |
| 1241 | 2-Cl, 3,5-(CH$_3$)$_2$ | OCH$_3$ | H |
| 1242 | 2-Br, 3,5-(CH$_3$)$_2$ | OCH$_3$ | H |
| 1243 | 2,6-Cl$_2$, 4-CH$_3$ | OCH$_3$ | H |
| 1244 | 2,6-F$_2$, 4-CH$_3$ | OCH$_3$ | H |
| 1245 | 2,6-Br$_2$, 4-CH$_3$ | OCH$_3$ | H |
| 1246 | 2,4-Br$_2$, 6-CH$_3$ | OCH$_3$ | H |
| 1247 | 2,4-F$_2$, 6-CH$_3$ | OCH$_3$ | H |
| 1248 | 2,4-Br$_2$, 6-CH$_3$ | OCH$_3$ | H |

TABLE A-continued

| Number | $R_m$ | $R^2$ | $R^1_n$ |
|---|---|---|---|
| 1249 | 2,6-(CH$_3$)$_2$, 4-F | OCH$_3$ | H |
| 1250 | 2,6-(CH$_3$)$_2$, 4-Cl | OCH$_3$ | H |
| 1251 | 2,6-(CH$_3$)$_2$, 4-Br | OCH$_3$ | H |
| 1252 | 3,5-(CH$_3$)$_2$, 4-F | OCH$_3$ | H |
| 1253 | 3,5-(CH$_3$)$_2$, 4-Cl | OCH$_3$ | H |
| 1254 | 3,5-(CH$_3$)$_2$, 4-Br | OCH$_3$ | H |
| 1255 | 2-CF$_3$ | OCH$_3$ | H |
| 1256 | 3-CF$_3$ | OCH$_3$ | H |
| 1257 | 4-CF$_3$ | OCH$_3$ | H |
| 1258 | 2-OCF$_3$ | OCH$_3$ | H |
| 1259 | 3-OCF$_3$ | OCH$_3$ | H |
| 1260 | 4-OCF$_3$ | OCH$_3$ | H |
| 1261 | 3-OCH$_2$CHF$_2$ | OCH$_3$ | H |
| 1262 | 2-NO$_2$ | OCH$_3$ | H |
| 1263 | 3-NO$_2$ | OCH$_3$ | H |
| 1264 | 4-NO$_2$ | OCH$_3$ | H |
| 1265 | 2-CN | OCH$_3$ | H |
| 1266 | 3-CN | OCH$_3$ | H |
| 1267 | 4-CN | OCH$_3$ | H |
| 1268 | 2-CH$_3$, 3-Cl | OCH$_3$ | H |
| 1269 | 2-CH$_3$, 4-Cl | OCH$_3$ | H |
| 1270 | 2-CH$_3$, 5-Cl | OCH$_3$ | H |
| 1271 | 2-CH$_3$, 6-Cl | OCH$_3$ | H |
| 1272 | 2-CH$_3$, 3-F | OCH$_3$ | H |
| 1273 | 2-CH$_3$, 4-F | OCH$_3$ | H |
| 1274 | 2-CH$_3$, 5-F | OCH$_3$ | H |
| 1275 | 2-CH$_3$, 6-F | OCH$_3$ | H |
| 1276 | 2-CH$_3$, 3-Br | OCH$_3$ | H |
| 1277 | 2-CH$_3$, 4-Br | OCH$_3$ | H |
| 1278 | 2-Pyridyl-2' | OCH$_3$ | H |
| 1279 | 3-Pyridyl-3' | OCH$_3$ | H |
| 1280 | 4-Pyridyl-4' | OCH$_3$ | H |
| 1281 | 2-CO—CH$_3$ | OCH$_3$ | H |
| 1282 | 3-CO—CH$_3$ | OCH$_3$ | H |
| 1283 | 4-CO—CH$_3$ | OCH$_3$ | H |
| 1284 | 2-C(=N—OCH$_3$)—CH$_3$ | OCH$_3$ | H |
| 1285 | 3-C(=N—OCH$_3$)—CH$_3$ | OCH$_3$ | H |
| 1286 | 4-C(=N—OCH$_3$)—CH$_3$ | OCH$_3$ | H |
| 1287 | 2-F | CH$_3$ | 5-CH$_3$ |
| 1288 | 3-F | CH$_3$ | 5-CH$_3$ |
| 1289 | 4-F | CH$_3$ | 5-CH$_3$ |
| 1290 | 2,4-F$_2$ | CH$_3$ | 5-CH$_3$ |
| 1291 | 2,4,6-F$_3$ | CH$_3$ | 5-CH$_3$ |
| 1292 | 2,3,4,5,6-F$_5$ | CH$_3$ | 5-CH$_3$ |
| 1293 | 2,3-F$_2$ | CH$_3$ | 5-CH$_3$ |
| 1294 | 2-Cl | CH$_3$ | 5-CH$_3$ |
| 1295 | 3-Cl | CH$_3$ | 5-CH$_3$ |
| 1296 | 4-Cl | CH$_3$ | 5-CH$_3$ |
| 1297 | 2,3-Cl$_2$ | CH$_3$ | 5-CH$_3$ |
| 1298 | 2,4-Cl$_2$ | CH$_3$ | 5-CH$_3$ |
| 1299 | 2,5-Cl$_2$ | CH$_3$ | 5-CH$_3$ |
| 1300 | 2,6-Cl$_2$ | CH$_3$ | 5-CH$_3$ |
| 1301 | 3,4-Cl$_2$ | CH$_3$ | 5-CH$_3$ |
| 1302 | 3,5-Cl$_2$ | CH$_3$ | 5-CH$_3$ |
| 1303 | 2,3,4-Cl$_3$ | CH$_3$ | 5-CH$_3$ |
| 1304 | 2,3,5-Cl$_3$ | CH$_3$ | 5-CH$_3$ |
| 1305 | 2,3,6-Cl$_3$ | CH$_3$ | 5-CH$_3$ |
| 1306 | 2,4,5-Cl$_3$ | CH$_3$ | 5-CH$_3$ |
| 1307 | 2,4,6-Cl$_3$ | CH$_3$ | 5-CH$_3$ |
| 1308 | 3,4,5-Cl$_3$ | CH$_3$ | 5-CH$_3$ |
| 1309 | 2,3,4,6-Cl$_4$ | CH$_3$ | 5-CH$_3$ |
| 1310 | 2,3,5,6-Cl$_4$ | CH$_3$ | 5-CH$_3$ |
| 1311 | 2,3,4,5,6-Cl$_5$ | CH$_3$ | 5-CH$_3$ |
| 1312 | 2-Br | CH$_3$ | 5-CH$_3$ |
| 1313 | 3-Br | CH$_3$ | 5-CH$_3$ |
| 1314 | 4-Br | CH$_3$ | 5-CH$_3$ |
| 1315 | 2,4-Br$_2$ | CH$_3$ | 5-CH$_3$ |
| 1316 | 2,5-Br$_2$ | CH$_3$ | 5-CH$_3$ |
| 1317 | 2,6-Br$_2$ | CH$_3$ | 5-CH$_3$ |
| 1318 | 2,4,6-Br$_3$ | CH$_3$ | 5-CH$_3$ |
| 1319 | 2,3,4,5,6-Br$_5$ | CH$_3$ | 5-CH$_3$ |
| 1320 | 2-I | CH$_3$ | 5-CH$_3$ |
| 1321 | 3-I | CH$_3$ | 5-CH$_3$ |
| 1322 | 4-I | CH$_3$ | 5-CH$_3$ |
| 1323 | 2,4-I$_2$ | CH$_3$ | 5-CH$_3$ |
| 1324 | 2-Cl, 3-F | CH$_3$ | 5-CH$_3$ |
| 1325 | 2-Cl, 4-F | CH$_3$ | 5-CH$_3$ |
| 1326 | 2-Cl, 5-F | CH$_3$ | 5-CH$_3$ |
| 1327 | 2-Cl, 6-F | CH$_3$ | 5-CH$_3$ |
| 1328 | 2-Cl, 3-Br | CH$_3$ | 5-CH$_3$ |
| 1329 | 2-Cl, 4-Br | CH$_3$ | 5-CH$_3$ |
| 1330 | 2-Cl, 5-Br | CH$_3$ | 5-CH$_3$ |
| 1331 | 2-Cl, 6-Br | CH$_3$ | 5-CH$_3$ |
| 1332 | 2-Br, 3-Cl | CH$_3$ | 5-CH$_3$ |
| 1333 | 2-Br, 4-Cl | CH$_3$ | 5-CH$_3$ |
| 1334 | 2-Br, 5-Cl | CH$_3$ | 5-CH$_3$ |
| 1335 | 2-Br, 3-F | CH$_3$ | 5-CH$_3$ |
| 1336 | 2-Br, 4-F | CH$_3$ | 5-CH$_3$ |
| 1337 | 2-Br, 5-F | CH$_3$ | 5-CH$_3$ |
| 1338 | 2-Br, 6-F | CH$_3$ | 5-CH$_3$ |
| 1339 | 2-F, 3-Cl | CH$_3$ | 5-CH$_3$ |
| 1340 | 2-F, 4-Cl | CH$_3$ | 5-CH$_3$ |
| 1341 | 2-F, 5-Cl | CH$_3$ | 5-CH$_3$ |
| 1342 | 3-Cl, 4-F | CH$_3$ | 5-CH$_3$ |
| 1343 | 3-Cl, 5-F | CH$_3$ | 5-CH$_3$ |
| 1344 | 3-Cl, 4-Br | CH$_3$ | 5-CH$_3$ |
| 1345 | 3-Cl, 5-Br | CH$_3$ | 5-CH$_3$ |
| 1346 | 3-F, 4-Cl | CH$_3$ | 5-CH$_3$ |
| 1347 | 3-F, 4-Br | CH$_3$ | 5-CH$_3$ |
| 1348 | 3-Br, 4-Cl | CH$_3$ | 5-CH$_3$ |
| 1349 | 3-Br, 4-F | CH$_3$ | 5-CH$_3$ |
| 1350 | 2,6-Cl$_2$, 4-Br | CH$_3$ | 5-CH$_3$ |
| 1351 | 2-CH$_3$ | CH$_3$ | 5-CH$_3$ |
| 1352 | 3-CH$_3$ | CH$_3$ | 5-CH$_3$ |
| 1353 | 4-CH$_3$ | CH$_3$ | 5-CH$_3$ |
| 1354 | 2,3-(CH$_3$)$_2$ | CH$_3$ | 5-CH$_3$ |
| 1355 | 2,4-(CH$_3$)$_2$ | CH$_3$ | 5-CH$_3$ |
| 1356 | 2,5-(CH$_3$)$_2$ | CH$_3$ | 5-CH$_3$ |
| 1357 | 2,6-(CH$_3$)$_2$ | CH$_3$ | 5-CH$_3$ |
| 1358 | 3,4-(CH$_3$)$_2$ | CH$_3$ | 5-CH$_3$ |
| 1359 | 3,5-(CH$_3$)$_2$ | CH$_3$ | 5-CH$_3$ |
| 1360 | 2,3,5-(CH$_3$)$_3$ | CH$_3$ | 5-CH$_3$ |
| 1361 | 2,3,4-(CH$_3$)$_3$ | CH$_3$ | 5-CH$_3$ |
| 1362 | 2,3,6-(CH$_3$)$_3$ | CH$_3$ | 5-CH$_3$ |
| 1363 | 2,4,5-(CH$_3$)$_3$ | CH$_3$ | 5-CH$_3$ |
| 1364 | 2,4,6-(CH$_3$)$_3$ | CH$_3$ | 5-CH$_3$ |
| 1365 | 3,4,5-(CH$_3$)$_3$ | CH$_3$ | 5-CH$_3$ |
| 1366 | 2,3,4,6-(CH$_3$)$_4$ | CH$_3$ | 5-CH$_3$ |
| 1367 | 2,3,5,6-(CH$_3$)$_4$ | CH$_3$ | 5-CH$_3$ |
| 1368 | 2,3,4,5,6-(CH$_3$)$_5$ | CH$_3$ | 5-CH$_3$ |
| 1369 | 2-C$_2$H$_5$ | CH$_3$ | 5-CH$_3$ |
| 1370 | 3-C$_2$H$_5$ | CH$_3$ | 5-CH$_3$ |
| 1371 | 4-C$_2$H$_5$ | CH$_3$ | 5-CH$_3$ |
| 1372 | 2,4-(C$_2$H$_5$)$_2$ | CH$_3$ | 5-CH$_3$ |
| 1373 | 2,6-(C$_2$H$_5$)$_2$ | CH$_3$ | 5-CH$_3$ |
| 1374 | 3,5-(C$_2$H$_5$)$_2$ | CH$_3$ | 5-CH$_3$ |
| 1375 | 2,4,6-(C$_2$H$_5$)$_3$ | CH$_3$ | 5-CH$_3$ |
| 1376 | 2-n-C$_3$H$_7$ | CH$_3$ | 5-CH$_3$ |
| 1377 | 3-n-C$_3$H$_7$ | CH$_3$ | 5-CH$_3$ |
| 1378 | 4-n-C$_3$H$_7$ | CH$_3$ | 5-CH$_3$ |
| 1379 | 2-i-C$_3$H$_7$ | CH$_3$ | 5-CH$_3$ |
| 1380 | 3-i-C$_3$H$_7$ | CH$_3$ | 5-CH$_3$ |
| 1381 | 4-i-C$_3$H$_7$ | CH$_3$ | 5-CH$_3$ |
| 1382 | 2,4-(i-C$_3$H$_7$)$_2$ | CH$_3$ | 5-CH$_3$ |
| 1383 | 2,6-(i-C$_3$H$_7$)$_2$ | CH$_3$ | 5-CH$_3$ |
| 1384 | 3,5-(i-C$_3$H$_7$)$_2$ | CH$_3$ | 5-CH$_3$ |
| 1385 | 2-s-C$_4$H$_9$ | CH$_3$ | 5-CH$_3$ |
| 1386 | 3-s-C$_4$H$_9$ | CH$_3$ | 5-CH$_3$ |
| 1387 | 4-s-C$_4$H$_9$ | CH$_3$ | 5-CH$_3$ |
| 1388 | 2-t-C$_4$H$_9$ | CH$_3$ | 5-CH$_3$ |
| 1389 | 3-t-C$_4$H$_9$ | CH$_3$ | 5-CH$_3$ |
| 1390 | 4-t-C$_4$H$_9$ | CH$_3$ | 5-CH$_3$ |
| 1391 | 4-n-C$_6$H$_{19}$ | CH$_3$ | 5-CH$_3$ |
| 1392 | 2-CH$_3$, 4-t-C$_4$H$_9$ | CH$_3$ | 5-CH$_3$ |
| 1393 | 2-CH$_3$, 6-t-C$_4$H$_9$ | CH$_3$ | 5-CH$_3$ |
| 1394 | 2-CH$_3$, 4-i-C$_3$H$_7$ | CH$_3$ | 5-CH$_3$ |
| 1395 | 2-CH$_3$, 5-i-C$_3$H$_7$ | CH$_3$ | 5-CH$_3$ |
| 1396 | 3-CH$_3$, 4-i-C$_3$H$_7$ | CH$_3$ | 5-CH$_3$ |
| 1397 | 2-cyclo-C$_6$H$_{11}$ | CH$_3$ | 5-CH$_3$ |
| 1398 | 3-cyclo-C$_6$H$_{11}$ | CH$_3$ | 5-CH$_3$ |
| 1399 | 4-cyclo-C$_6$H$_{11}$ | CH$_3$ | 5-CH$_3$ |
| 1400 | 2-Cl, 4-C$_6$H$_5$ | CH$_3$ | 5-CH$_3$ |
| 1401 | 2-Br, 4-C$_6$H$_5$ | CH$_3$ | 5-CH$_3$ |
| 1402 | 2-OCH$_3$ | CH$_3$ | 5-CH$_3$ |

TABLE A-continued

| Number | $R_m$ | $R^2$ | $R^1_n$ |
|---|---|---|---|
| 1403 | 3-OCH$_3$ | CH$_3$ | 5-CH$_3$ |
| 1404 | 4-OCH$_3$ | CH$_3$ | 5-CH$_3$ |
| 1405 | 2-OC$_2$H$_5$ | CH$_3$ | 5-CH$_3$ |
| 1406 | 3-O—C$_2$H$_5$ | CH$_3$ | 5-CH$_3$ |
| 1407 | 4-O—C$_2$H$_5$ | CH$_3$ | 5-CH$_3$ |
| 1408 | 2-O-n-C$_3$H$_7$ | CH$_3$ | 5-CH$_3$ |
| 1409 | 3-O-n-C$_3$H$_7$ | CH$_3$ | 5-CH$_3$ |
| 1410 | 4-O-n-C$_3$H$_7$ | CH$_3$ | 5-CH$_3$ |
| 1411 | 2-O-i-C$_3$H$_7$ | CH$_3$ | 5-CH$_3$ |
| 1412 | 3-O-i-C$_3$H$_7$ | CH$_3$ | 5-CH$_3$ |
| 1413 | 4-O-i-C$_3$H$_7$ | CH$_3$ | 5-CH$_3$ |
| 1414 | 2-O-n-C$_6$H$_{13}$ | CH$_3$ | 5-CH$_3$ |
| 1415 | 3-O-n-C$_6$H$_{13}$ | CH$_3$ | 5-CH$_3$ |
| 1416 | 4-O-n-C$_6$H$_{13}$ | CH$_3$ | 5-CH$_3$ |
| 1417 | 2-O—CH$_2$C$_6$H$_5$ | CH$_3$ | 5-CH$_3$ |
| 1418 | 3-O—CH$_2$C$_6$H$_5$ | CH$_3$ | 5-CH$_3$ |
| 1419 | 4-O—CH$_2$C$_6$H$_5$ | CH$_3$ | 5-CH$_3$ |
| 1420 | 2-O—(CH$_2$)$_3$C$_6$H$_5$ | CH$_3$ | 5-CH$_3$ |
| 1421 | 4-O—(CH$_2$)$_3$C$_6$H$_5$ | CH$_3$ | 5-CH$_3$ |
| 1422 | 2,3-(OCH$_3$)$_2$ | CH$_3$ | 5-CH$_3$ |
| 1423 | 2,4-(OCH$_3$)$_2$ | CH$_3$ | 5-CH$_3$ |
| 1424 | 2,5-(OCH$_3$)$_2$ | CH$_3$ | 5-CH$_3$ |
| 1425 | 2,6-(OCH$_3$)$_2$ | CH$_3$ | 5-CH$_3$ |
| 1426 | 3,4-(OCH$_3$)$_2$ | CH$_3$ | 5-CH$_3$ |
| 1427 | 3,5-(OCH$_3$)$_2$ | CH$_3$ | 5-CH$_3$ |
| 1428 | 2-O-t-C$_4$H$_9$ | CH$_3$ | 5-CH$_3$ |
| 1429 | 3-O-t-C$_4$H$_9$ | CH$_3$ | 5-CH$_3$ |
| 1430 | 4-O-t-C$_4$H$_9$ | CH$_3$ | 5-CH$_3$ |
| 1431 | 3-(3'-Cl—C$_6$H$_4$) | CH$_3$ | 5-CH$_3$ |
| 1432 | 4-(4'-CH$_3$—C$_6$H$_4$) | CH$_3$ | 5-CH$_3$ |
| 1433 | 2-O—C$_6$H$_5$ | CH$_3$ | 5-CH$_3$ |
| 1434 | 3-O—C$_6$H$_5$ | CH$_3$ | 5-CH$_3$ |
| 1435 | 4-O—C$_6$H$_5$ | CH$_3$ | 5-CH$_3$ |
| 1436 | 2-O-(2'-F—C$_6$H$_4$) | CH$_3$ | 5-CH$_3$ |
| 1437 | 3-O-(3'-Cl—C$_6$H$_4$) | CH$_3$ | 5-CH$_3$ |
| 1438 | 4-O-(4'-CH$_3$—C$_6$H$_4$) | CH$_3$ | 5-CH$_3$ |
| 1439 | 2,3,6-(CH$_3$)$_3$, 4-F | CH$_3$ | 5-CH$_3$ |
| 1440 | 2,3,6-(CH$_3$)$_3$, 4-Cl | CH$_3$ | 5-CH$_3$ |
| 1441 | 2,3,6-(CH$_3$)$_3$, 4-Br | CH$_3$ | 5-CH$_3$ |
| 1442 | 2,4-(CH$_3$)$_2$, 6-F | CH$_3$ | 5-CH$_3$ |
| 1443 | 2,4-(CH$_3$)$_2$, 6-Cl | CH$_3$ | 5-CH$_3$ |
| 1444 | 2,4-(CH$_3$)$_2$, 6-Br | CH$_3$ | 5-CH$_3$ |
| 1445 | 2-i-CH$_3$H$_1$, 4-Cl, 5-CH$_3$ | CH$_3$ | 5-CH$_3$ |
| 1446 | 2-Cl, 4-NO$_2$ | CH$_3$ | 5-CH$_3$ |
| 1447 | 2-NO$_2$, 4-Cl | CH$_3$ | 5-CH$_3$ |
| 1448 | 2-OCH$_3$, 5-NO$_2$ | CH$_3$ | 5-CH$_3$ |
| 1449 | 2,4-Cl$_2$, 5-NO$_2$ | CH$_3$ | 5-CH$_3$ |
| 1450 | 2,4-Cl$_2$, 6-NO$_2$ | CH$_3$ | 5-CH$_3$ |
| 1451 | 2,6-Cl$_2$, 4-NO$_2$ | CH$_3$ | 5-CH$_3$ |
| 1452 | 2,6-Br$_2$, 4-NO$_2$ | CH$_3$ | 5-CH$_3$ |
| 1453 | 2,6-I$_2$, 4-NO$_2$ | CH$_3$ | 5-CH$_3$ |
| 1454 | 2-CH$_3$, 5-i-CH$_3$H$_7$, 4-Cl | CH$_3$ | 5-CH$_3$ |
| 1455 | 2-CO$_2$CH$_3$ | CH$_3$ | 5-CH$_3$ |
| 1456 | 3-CO$_2$CH$_3$ | CH$_3$ | 5-CH$_3$ |
| 1457 | 4-CO$_2$CH$_3$ | CH$_3$ | 5-CH$_3$ |
| 1458 | 2-CH$_2$—OCH$_3$ | CH$_3$ | 5-CH$_3$ |
| 1459 | 3-CH$_2$—OCH$_3$ | CH$_3$ | 5-CH$_3$ |
| 1460 | 4-CH$_2$—OCH$_3$ | CH$_3$ | 5-CH$_3$ |
| 1461 | 2-Me-4-CH$_3$—CH(CH$_3$)—CO | CH$_3$ | 5-CH$_3$ |
| 1462 | 2-CH$_3$-4-(CH$_3$—C=NOCH$_3$) | CH$_3$ | 5-CH$_3$ |
| 1463 | 2-CH$_3$-4-(CH$_3$—C=NOC$_2$H$_5$) | CH$_3$ | 5-CH$_3$ |
| 1464 | 2-CH$_3$-4-(CH$_3$—C=NO-n-C$_3$H$_7$) | CH$_3$ | 5-CH$_3$ |
| 1465 | 2-CH$_3$-4-(CH$_3$—C=NO-i-C$_3$H$_7$) | CH$_3$ | 5-CH$_3$ |
| 1466 | 2,5-(CH$_3$)$_2$-4-(CH$_3$—C=NOCH$_3$) | CH$_3$ | 5-CH$_3$ |
| 1467 | 2,5-(CH$_3$)$_2$-4-(CH$_3$—C=NOC$_2$H$_5$) | CH$_3$ | 5-CH$_3$ |
| 1468 | 2,5-(CH$_3$)$_2$-4-(CH$_3$—C=NO-n-C$_3$H$_7$) | CH$_3$ | 5-CH$_3$ |
| 1469 | 2,5-(CH$_3$)$_2$-4-(CH$_3$—C=NO-i-C$_3$H$_7$) | CN | 5-CH$_3$ |
| 1470 | 2-C$_6$H$_5$ | CH$_3$ | 5-CH$_3$ |
| 1471 | 3-C$_6$H$_5$ | CH$_3$ | 5-CH$_3$ |
| 1472 | 4-C$_6$H$_5$ | CH$_3$ | 5-CH$_3$ |
| 1473 | 2-(2'-F—C$_6$H$_4$) | CH$_3$ | 5-CH$_3$ |
| 1474 | 2-CH$_3$, 5-Br | CH$_3$ | 5-CH$_3$ |
| 1475 | 2-CH$_3$, 6-Br | CH$_3$ | 5-CH$_3$ |
| 1476 | 2-Cl, 3-CH$_3$ | CH$_3$ | 5-CH$_3$ |
| 1477 | 2-Cl, 4-CH$_3$ | CH$_3$ | 5-CH$_3$ |
| 1478 | 2-Cl, 5-CH$_3$ | CH$_3$ | 5-CH$_3$ |
| 1479 | 2-F, 3-CH$_3$ | CH$_3$ | 5-CH$_3$ |
| 1480 | 2-F, 4-CH$_3$ | CH$_3$ | 5-CH$_3$ |
| 1481 | 2-F, 5-CH$_3$ | CH$_3$ | 5-CH$_3$ |
| 1482 | 2-Br, 3-CH$_3$ | CH$_3$ | 5-CH$_3$ |
| 1483 | 2-Br, 4-CH$_3$ | CH$_3$ | 5-CH$_3$ |
| 1484 | 2-Br, 5-CH$_3$ | CH$_3$ | 5-CH$_3$ |
| 1485 | 3-CH$_3$, 4-Cl | CH$_3$ | 5-CH$_3$ |
| 1486 | 3-CH$_3$, 5-Cl | CH$_3$ | 5-CH$_3$ |
| 1487 | 3-CH$_3$, 4-F | CH$_3$ | 5-CH$_3$ |
| 1488 | 3-CH$_3$, 5-F | CH$_3$ | 5-CH$_3$ |
| 1489 | 3-CH$_3$, 4-Br | CH$_3$ | 5-CH$_3$ |
| 1490 | 3-CH$_3$, 5-Br | CH$_3$ | 5-CH$_3$ |
| 1491 | 3-F, 4-CH$_3$ | CH$_3$ | 5-CH$_3$ |
| 1492 | 3-Cl, 4-CH$_3$ | CH$_3$ | 5-CH$_3$ |
| 1493 | 3-Br, 4-CH$_3$ | CH$_3$ | 5-CH$_3$ |
| 1494 | 2-Cl, 4,5-(CH$_3$)$_2$ | CH$_3$ | 5-CH$_3$ |
| 1495 | 2-Br, 4,5-(CH$_3$)$_2$ | CH$_3$ | 5-CH$_3$ |
| 1496 | 2-Cl, 3,5-(CH$_3$)$_2$ | CH$_3$ | 5-CH$_3$ |
| 1497 | 2-Br, 3,5-(CH$_3$)$_2$ | CH$_3$ | 5-CH$_3$ |
| 1498 | 2,6-Cl$_2$, 4-CH$_3$ | CH$_3$ | 5-CH$_3$ |
| 1499 | 2,6-F$_2$, 4-CH$_3$ | CH$_3$ | 5-CH$_3$ |
| 1500 | 2,6-Br$_2$, 4-CH$_3$ | CH$_3$ | 5-CH$_3$ |
| 1501 | 2,4-Br$_2$, 6-CH$_3$ | CH$_3$ | 5-CH$_3$ |
| 1502 | 2,4-F$_2$, 6-CH$_3$ | CH$_3$ | 5-CH$_3$ |
| 1503 | 2,4-Br$_2$, 6-CH$_3$ | CH$_3$ | 5-CH$_3$ |
| 1504 | 2,6-(CH$_3$)$_2$, 4-F | CH$_3$ | 5-CH$_3$ |
| 1505 | 2,6-(CH$_3$)$_2$, 4-Cl | CH$_3$ | 5-CH$_3$ |
| 1506 | 2,6-(CH$_3$)$_2$, 4-Br | CH$_3$ | 5-CH$_3$ |
| 1507 | 3,5-(CH$_3$)$_2$, 4-F | CH$_3$ | 5-CH$_3$ |
| 1508 | 3,5-(CH$_3$)$_2$, 4-Cl | CH$_3$ | 5-CH$_3$ |
| 1509 | 3,5-(CH$_3$)$_2$, 4-Br | CH$_3$ | 5-CH$_3$ |
| 1510 | 2-CF$_3$ | CH$_3$ | 5-CH$_3$ |
| 1511 | 3-CF$_3$ | CH$_3$ | 5-CH$_3$ |
| 1512 | 4-CF$_3$ | CH$_3$ | 5-CH$_3$ |
| 1513 | 2-OCF$_3$ | CH$_3$ | 5-CH$_3$ |
| 1514 | 3-OCF$_3$ | CH$_3$ | 5-CH$_3$ |
| 1515 | 4-OCF$_3$ | CH$_3$ | 5-CH$_3$ |
| 1516 | 3-OCH$_2$CHF$_2$ | CH$_3$ | 5-CH$_3$ |
| 1517 | 2-NO$_2$ | CH$_3$ | 5-CH$_3$ |
| 1518 | 3-NO$_2$ | CH$_3$ | 5-CH$_3$ |
| 1519 | 4-NO$_2$ | CH$_3$ | 5-CH$_3$ |
| 1520 | 2-CN | CH$_3$ | 5-CH$_3$ |
| 1521 | 3-CN | CH$_3$ | 5-CH$_3$ |
| 1522 | 4-CN | CH$_3$ | 5-CH$_3$ |
| 1523 | 2-CH$_3$, 3-Cl | CH$_3$ | 5-CH$_3$ |
| 1524 | 2-CH$_3$, 4-Cl | CH$_3$ | 5-CH$_3$ |
| 1525 | 2-CH$_3$, 5-Cl | CH$_3$ | 5-CH$_3$ |
| 1526 | 2-CH$_3$, 6-Cl | CH$_3$ | 5-CH$_3$ |
| 1527 | 2-CH$_3$, 3-F | CH$_3$ | 5-CH$_3$ |
| 1528 | 2-CH$_3$, 4-F | CH$_3$ | 5-CH$_3$ |
| 1529 | 2-CH$_3$, 5-F | CH$_3$ | 5-CH$_3$ |
| 1530 | 2-CH$_3$, 6-F | CH$_3$ | 5-CH$_3$ |
| 1531 | 2-CH$_3$, 3-Br | CH$_3$ | 5-CH$_3$ |
| 1532 | 2-CH$_3$, 4-Br | CH$_3$ | 5-CH$_3$ |
| 1533 | 2-Pyridyl-2' | CH$_3$ | 5-CH$_3$ |
| 1534 | 3-Pyridyl-3' | CH$_3$ | 5-CH$_3$ |
| 1535 | 4-Pyridyl-4' | CH$_3$ | 5-CH$_3$ |
| 1536 | 2-CO—CH$_3$ | CH$_3$ | 5-CH$_3$ |
| 1537 | 3-CO—CH$_3$ | CH$_3$ | 5-CH$_3$ |
| 1538 | 4-CO—CH$_3$ | CH$_3$ | 5-CH$_3$ |
| 1539 | 2-C(=N—OCH$_3$)—CH$_3$ | CH$_3$ | 5-CH$_3$ |
| 1540 | 3-C(=N—OCH$_3$)—CH$_3$ | CH$_3$ | 5-CH$_3$ |
| 1541 | 4-C(=N—OCH$_3$)—CH$_3$ | CH$_3$ | 5-CH$_3$ |

The compounds of the formula I according to the invention are suitable for controlling harmful fungi and animal pests of the insects, arachnids and nematodes classes. They can be employed as fungicides and pesticides in crop protection and in the hygiene, stored material protection and veterinary sectors.

The harmful insects include:
from the order of the butterflies (Lepidoptera), for example, *Adoxophyes orana*, *Agrotis ypsilon*, *Agrotis segetum*, *Alabama argillacea*, *Anticarsia gemmatalis*, *Argyresthia conjugella*, *Autographa gamma*, *Cacoecia murinana*, *Capua reticulana*, *Choristoneura* fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis, further Galleria mellonella and Sitotroga cerealella, Ephestia cautella, Tineola bisselliella;

from the order of the beetles (Coleoptera), for example, Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, further Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;

from the order of the dipterous insects (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa, further Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia cuprina, Lucilia sericata, Musca domestica, Muscina stabulans, Oestrus ovis, Tabanus bovinus, Simulium damnosum;

from the order of the thrips (Thysanoptera), for example, Frankliniella fusca, Frankliniella occidentalis, Frankliniella tritici, Haplothrips tritici, Scirtothrips citri, Thrips oryzae, Thrips palmi, Thrips tabaci;

from the order of the hymenopterous insects (Hymenoptera), for example, Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the bugs (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the plant-sucking insects (Homoptera), for example, Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;

from the order of the termites (Isoptera), for example, Calotermes flavicollis, Leucotermes flavipes, Macrotermes subhyalinus, Odontotermes formosanus, Reticulitermes lucifugus, Termes natalensis;

from the order of the orthopterous insects (Orthoptera), for example, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, further Acheta domestica, Blatta orientalis, Blattella germanica, Periplaneta americana;

from the order of the Arachnoidea, for example, phytophagous mites such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranychus pacificus, Tetranychus

*urticae,* ticks such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus everts* ias well as animal-parasitic mites such as *Dermanyssus gallinae, Psoroptes ovis* and *Sarcoptes scabiei;* from the class of the nematodes, for example, root gall nematodes, eg. *Meloidogyne hapla, Meloidogyne incognita, Meloidogyne javanica,* cyst-forming nematodes, eg. *Globodera pallida, Globodera rostochiensis, Heterodera avenae, Heterodera glycines, Heterodera schachtii,* migratory endoparasites and semi-endoparasitic nematodes, eg. *Heliocotylenchus multicinctus, Hirschmanniella oryzae, Hoplolaimus spp, Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans,* stem and leaf nematodes eg. *Anguina tritici, Aphelenchoides besseyi, Ditylenchus angustus, Ditylenchus dipsaci,* virus vectors, eg. *Longidorus spp., Trichodorus christei, Trichodorus viruliferus, Xiphinema index, Xiphinema mediterraneum.*

The compounds I can be applied as such, in the form of their formulations or the application forms prepared therefrom, eg. in the form of directly sprayable solutions, powders, suspensions or dispersions, emulsions, oil dispersions, pastes, dust compositions, scattering compositions or granules, by spraying, atomizing, dusting, scattering or watering. The application forms depend entirely on the intended uses; in each case they should if possible guarantee the finest dispersion of the active compounds according to the invention.

The compounds of the formula I are in some cases systemically active as fungicides. They can be employed as foliar and soil fungicides against a broad spectrum of phytopathogenic fungi, in particular from the Ascomycetes, Deuteromycetes, Phycomycetes and Basidiomycetes classes.

They are of particular importance for controlling a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for controlling the following plant diseases:

*Erysiphe graminis*(powdery mildew) in cereals,

*Erysiphe cichoracearum* and *Sphaerotheca fuliginea* on cucurbits,

*Podosphaera leucotricha* on apples,

*Uncinula necator* on vines,

*Puccinia* species on cereals,

*Rhizoctonia* species on cotton and grass,

*Ustilago species on cereals and sugar cane,*

*Venturia inaequalis*(scab) on apples,

*Helminthosporium* species on cereals,

*Septoria nodorum* on wheat,

*Botrytis cinerea*(gray mold) on strawberries, vines,

*Cercospora arachidicola* on groundnuts,

*Pseudocercosporella herpotrichoides* on wheat, barley,

*Pyricularia oryzae* on rice,

*Phytophthora infestans* on potatoes and tomatoes,

*Fusarium* and *Verticillium* species on various plants,

*Plasmopara viticola* on vines,

*Alternaria* species on vegetables and fruit.

The novel compounds can also be employed in the protection of materials, eg. for the protection of wood, paper and textiles eg. against *Paecilomyces variotii.*

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:

solvents such as aromatics (eg. xylene), chlorinated aromatics (eg. chlorobenzenes), paraffins (eg. petroleum fractions), alcohols (eg. -methanol, butanol), ketones (eg. cyclohexanone), amines (eg. ethanolamine, dimethylformamide) and water;

carriers such as ground natural minerals (eg. kaolins, argil-laceous earths, talc, chalk) and ground synthetic minerals (eg. highly disperse silica, silicates);

emulsifiers such as nonionic and anionic emulsifiers (eg. polyoxyethylene fatty alcohol ethers, alkylsulfonates and arylsulfonates) and dispersants such as lignin-sulfite waste liquors and methyl-cellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl-and alkylarylsulfonates, alkyl, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ether, ethoxylated isooctyl-, octyl- or nonylphenol, alkylphenyl or tributylphenyl polyglycol ether, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substrates can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, broadcasting and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, of active compound are suitable.

The active compounds are normally employed in a purity of from 90% to 100%, preferably from 95% to 100% (according to NMR spectrum).

EXAMPLES OF SUCH PREPARATIONS ARE

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

III. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a mineral oil fraction of boiling point from 210 to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray mixture is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adherence;

VIII. a stable aqueous dispersion of 40 parts by weight of a compound I according to the invention, 10 parts by weight of the sodium salt of a phenolsulfonic acid/urea/formal-dehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the fungi or the seed, plants, materials or the soil to be protected from fungal attack with a fungicidally active amount of the active compounds.

They are applied before or after the infection of the materials, plants or seed by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha of active compound.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even only immediately before use (tank mix). On mixing with fungicides or insecticides, in many cases an increase in the fungicidal spectrum of action is obtained here.

The following list of fungicides with which the compounds according to the invention can be applied jointly is intended to illustrate the combination possibilities, but not to restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis(thiocarbamoyl) disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis(dimethylamino)-phosphinyl ]-3-phenyl-1,2,4-triazole, 2,3-dicyano-1,4-dithioanthraquinone, 2-thio-1,3-dithiolo-β-[4,5-b] quinoxaline, methyl 1-(butylcarbamoyl)-2-benzimidazolecarbamate, 2-methoxycarbonylaminobenzimidazole, 2-(fur-2-yl)benzimidazole, 2-(thiazol-4-yl)-benzimidazole, N-(1,1,2,2-tetrachloroethylthio)tetrahydrophthalimide, N-trichloro-methylthiotetrahydrophthalimide, N-trichloro-methylthiophthalimide, N-dichlorofluoromethylthio-N-',N'-dimethyl-N-phenylsulfamide, 5-ethoxy-3-trichloro-methyl-1,2,3-thiadiazole, 2-thiocyanato-methylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3 -dihydro-5-carboxanilido-6-methyl-1,4-oxathiin 4,4-dioxide, 2-methyl-5,6 -dihydro-4H-pyran-3-carboxanilide, 2-methylfuran-3-carboxanilide, 2,5-dimethylfuran-3-carboxanilide, 2,4,5-tri-methylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis 1(2,2,2-trichloroethyl)) formamide, 1-(3,4-dichloroanilino)(1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl] piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl 1-(1H-1,2,4-triazol 1-yl)-2-butanone, 1-(4-chlorophenoxy)-3,3-dimethyl 1-(1H-1,2,4-triazol 1-yl)-2-butanol, α-(2-chlorophenyl)-α-(4-chlorophenyl)-5-pyrimidine-methanol, 5-butyl-2-dimethylamino-4-hydroxy-6-methylpyrimidine, bis(p-chlorophenyl)-3-pyridine-methanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine,
3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino ]-acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoro-methylphenyl)-5-trifluoro-methyl-3-chloro-2-aminopyridine, 1-((bis(4-fluorophenyl)-methylsilyl)-methyl)-1H-1,2,4-triazole.

Synthesis examples

The procedures described in the synthesis examples below were used with appropriate modification of the starting compounds to obtain further compounds I. The compounds thus obtained are listed with physical data in the following table.

1. Methyl N-methoxy-N-(2-(4'-(2"-fluorophenyl)-2'-methoxyphe-noxymethyl)phenyl)carbamate

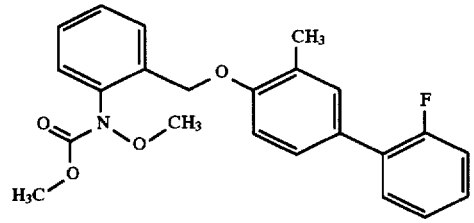

A mixture of 1 g (2.6 mmol) of -methyl N-methoxy-N-(2-(4'-bromo-2'-methylphenoxymethyl)phenyl)carbamate (preparation in the same way as in WO 93/15046), 0.55 g (3.9 mmol) of 2-fluorophenylboronic acid and 0.33 g (3.9 mmol) of NaHCO₃ is refluxed and stirred in 4 ml of dimethoxyethane/water 1:1 for about 5 hours. The reaction mixture is then cooled and diluted with water, and the aqueous phase is extracted three times with -methylene chloride. The combined organic phases are extracted with water, dried over MgSO₄ and concentrated. The residue obtained is 1 g (95%) of the title compound as pale yellow crystals (m.p. =71° C.).

¹H-NMR (CDCl₃; δ in ppm): 7.7(d,1H,phenyl); 7.35(m, 8H,phenyl); 6.95(m,2H,phenyl); 5.2(s,2H,OCH₂); 3.82(s, 3H,OCH₃); 3.75(s,3H,OCH₃); 2.4(s,3H,CH₃)

TABLE B

| | | Physical data of some compounds | | |
|---|---|---|---|---|
| No. | R_m | R² | R_n¹ | M.p.[°C.] or NMR (CDCl₃; δ in ppm) |
| 1 | 4-F | F | H | 3.8(s, 3H); 3.73(s, 3H) |
| 2 | 2-F | CH₃ | H | 71 |
| 3 | 3-OCH₃ | CH₃ | H | 3.85(s, 3H); 3.8(s, 3H); 3.73(s, 3H) |
| 4 | 2-CH₃ | CH₃ | H | 3.8(s, 3H); 3.73(s, 3H) |
| 5 | 2,4-Cl₂ | CH₃ | H | 3.82(s, 3H); 3.75(s, 3H) |
| 6 | 4-OCH₃ | CH₃ | H | 113 |
| 7 | 2-OCH₃ | CH₃ | H | 3.8(2s, each 3H); 3.75(s, 3H) |
| 8 | 3,4-Cl₂ | CH₃ | H | 3.8(s, 3H); 3.73(s, 3H) |
| 9 | 3,5-Cl₂ | CH₃ | H | 3.83(s, 3H); 3.77(s, 3H) |
| 10 | 4-CH₃ | CH₃ | H | 3.7(s, 3H); 3.66(s, 3H) (in DMSO-d₆) |

Examples of the action against harmful fungi

It was possible to show the fungicidal action of the compounds of the formula I by the following tests:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and diluted with water according to the concentration desired.

Activity against Plasmopara viticola

Potted vines (variety: Muller Thurgau) were sprayed with the active compound preparation until dripping wet. After 8 days, the plants were sprayed with a zoospore suspension of the fungus Plasmopara viticola and kept at high atmospheric humidity for 5 days at 20°–30° C. Before assessment, the plants were then kept at high atmospheric humidity for 16 h. Assessment was carried out visually.

In this test, the plants treated with the active compounds 2, 3, 4, 5, 6, 7, 9 and 10 according to the invention showed a fungal attack of 5% or less, while the untreated plants (control test) were attacked to 70%.

Activity against Puccinia recondita (brown rust of wheat)

Leaves of wheat seedlings (Kanzler variety) were dusted with spores of brown rust (Puccinia recondita). The plants treated in this way were incubated for 24 h at 20°–22° C. and a relative atmospheric humidity of 90–95% and then treated with the aqueous active compound preparation. After a further 8 days at 20°–22° C. and 65–70% relative atmospheric humidity, the extent of the fungal development was determined. Assessment was carried out visually. In this test, the plants treated with the active compounds 1, 2, 3, 4, 5, 6, 7, 8, 9 and 10 according to the invention showed a fungal attack of 5% or less, while the untreated plants (control test) were attacked to 65%.

Examples of the action against animal pests

It was possible to show the action of the compounds of the general formula I against animal pests by the following tests: The active compounds were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor®EL (Emulan® EL, emulsifier based on ethoxylated fatty alcohols)

and diluted with acetone in the case of a) or with water in the case of b) according to the desired concentration.

After conclusion of the tests, the lowest concentration at which the compounds still caused an 80–100% inhibition or mortality in comparison with untreated control tests was determined in each case (activity threshold or minimum concentration).

We claim:

1. A 2-[4-biphenyloxymethylene]anilide of the formula I

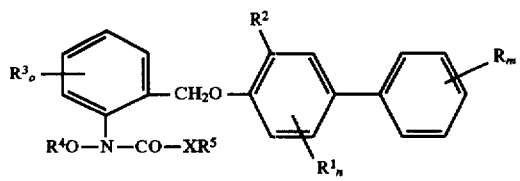

where the indices and the substituents have the following meanings:

R is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_1$–$C_4$-alkylcarbonyl, $C_1$–$C_4$-alkoxycarbonyl, $C_1$–$C_4$-alkylaminocarbonyl, di($C_1$–$C_4$-alkyl)aminocarbonyl, $C_1$–$C_4$-alkylcarbonylamino, $C_1$–$C_4$-alkylcarbonyl($C_1$–$C_4$-alkylamino), $C_2$–$C_4$-alkenyl, $C_3$–$C_4$-alkenyloxy, $C_2$–$C_4$-alkynyl, $C_3$–$C_4$-alkynyloxy, $C_3$–$C_6$-cycloalkyl or $C(R^a)$=$NOR^b$;

$R^a$ and $R^b$ are hydrogen, alkyl, alkenyl, alkynyl, cycloalkyl or cycloalkenyl;

m is 1, 2, 3, 4 or 5, it being possible for the radicals R to be different if m is greater than 1;

$R^1$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_1$–$C_4$-alkylcarbonyl, $C_1$–$C_4$-alkoxycarbonyl, $C_1$–$C_4$-alkylaminocarbonyl, di($C_1$–$C_4$-alkyl)aminocarbonyl, $C_1$–$C_4$-alkylcarbonylamino, $C_1$–$C_4$-alkylcarbonyl($C_1$–$C_4$-alkylamino), $C_2$–$C_4$-alkenyl, $C_3$–$C_4$-alkenyloxy, $C_2$–$C_4$-alkynyl, $C_3$–$C_4$-alkynyloxy, $C_3$–$C_6$-cycloalkyl or $C(R^a)$=$NOR^b$;

n is 0, 1 or 2, it being possible for the radicals $R^1$ to be different if n is 2;

$R^2$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_1$–$C_4$-alkylcarbonyl, $C_1$–$C_4$-alkoxycarbonyl, $C_1$–$C_4$-alkylaminocarbonyl, di($C_1$–$C_4$-alkyl)aminocarbonyl, $C_1$–$C_4$-alkylcarbonylamino, $C_1$–$C_4$-alkylcarbonyl($C_1$–$C_4$-alkylamino), $C_2$–$C_4$-alkenyl, $C_3$–$C_4$-alkenyloxy, $C_2$–$C_4$-alkynyl, $C_3$–$C_4$-alkynyloxy, $C_3$–$C_6$-cycloalkyl or $C(R^a)$=$NOR^b$;

$R^3$ is nitro, cyano, halogen, unsubst. or subst. alkyl, alkenyl, alkynyl, alkoxy, alkenyloxy, alkynyloxy or $C_1$–$C_4$-alkylcarbonyl, $C_1$–$C_4$-alkoxycarbonyl, $C_1$–$C_4$-alkylaminocarbonyl, di($C_1$–$C_4$-alkyl)aminocarbonyl, $C_1$–$C_4$-alkylcarbonylamino, $C_1$–$C_4$-alkylcarbonyl($C_1$–$C_4$-alkylamino), $C(R^a)$=$NOR^b$ or in the case where o is greater than 1, is additional an unsubst. or subst. bridge bonded to two adjacent ring atoms, which can carry three to four members from the group consisting of 3 or 4 carbon atoms, and 2 or 3 carbon atoms and 1 or 2 nitrogen, oxygen and/or sulfur atoms, it being possible for this bridge, together with the ring to which it is bonded, to form a partially unsaturated or aromatic radical;

o is 0, 1, 2, 3 or 4, it being possible for the substituents $R^3$ to be different if n is greater than 1;

$R^4$ is hydrogen, unsubst. or subst. alkyl, alkenyl, alkynyl, cycloalkyl, cycloalkenyl, alkylcarbonyl or alkoxycarbonyl;

X is a direct bond or $CH_2$, O or $NR^c$;

$R^c$ is hydrogen, alkyl, alkenyl, alkynyl, cycloalkyl or cycloalkenyl;

$R^5$ is alkyl, alkenyl, alkynyl, cycloalkyl or cycloalkenyl, or or in the case where X is $NR^c$, is additionally hydrogen.

2. A process for preparing the compounds of the formula I as claimed in claim 1, where $R^4$ is hydrogen and X is a direct bond or oxygen, which comprises converting a benzyl derivative of the formula II

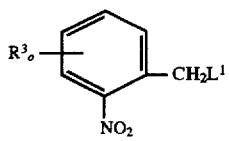

where $L^1$ is a nucleophilically replaceable group,

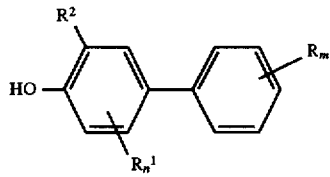

into the corresponding 2-[4-biphenyloxymethylene] nitrobenzene of the formula IV

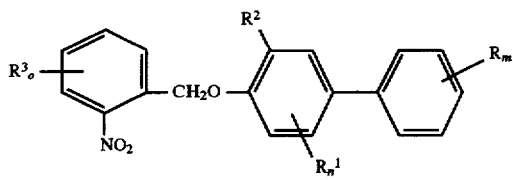

in the presence of a base using a 4-biphenol of the formula III, then reducing IV to the N-hydroxyaniline of the formula Va

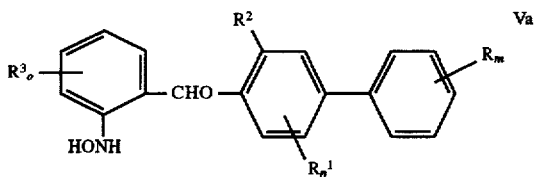

and converting Va into I using a carbonyl compound of the formula VI

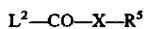    VI where $L^2$ is halogen.

3. A process for preparing the compounds of the formula I as claimed in claim 1, where $R^4$ is not hydrogen, which comprises reducing a benzyl derivative of the formula IIa

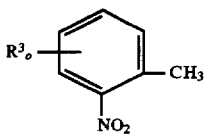

first to the corresponding N-hydroxyaniline of the formula Vb

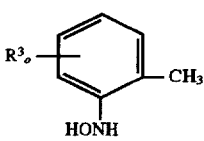

converting Vb into the corresponding anilide of the formula VII

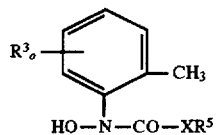

using a carbonyl compound of the formula VI as set forth in claim 2 and then converting VII using a compound VIII

    VIII where $L^3$ is a nucleophilically replaceable group and $R^4$ is not hydrogen, into the amide of the formula IX

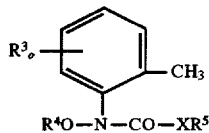

then converting IX into the corresponding benzyl halide of the formula X

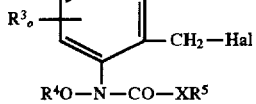

where Hal is a halogen atom, and converting X into I in the presence of a base using a 4-biphenol of the formula III as set forth in claim 2.

4. A process for preparing the compounds I as claimed in claim 1, where $R^4$ is not hydrogen, which comprises reacting a corresponding compound of the formula I where $R^4$ is hydrogen with an appropriate compound of the formula VIII as set forth in claim 3.

5. A process for preparing the compounds of the formula I where X is $NR^c$, which comprises converting a benzanilide of the formula IXa

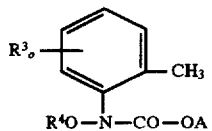

where A is alkyl or phenyl, into the corresponding benzyl halide of the formula Xa

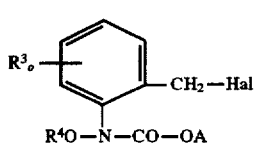

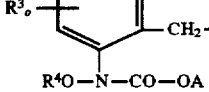

where Hal is a halogen atom, converting Xa into a compound of the formula I.A

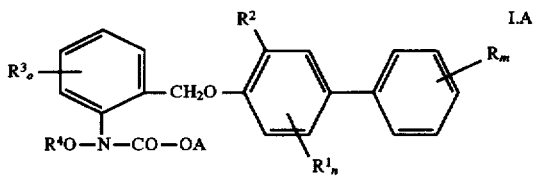

in the presence of a base using a 4-biphenol of the formula III as set forth in claim 2 and then reacting I.A with an amine of the formula XIa or XIb

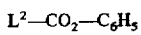   XIa

HNR$^c$ R$^5$   XIb to give I.

6. A process for preparing compounds of the formula I.A as set forth in claim 5, where A is phenyl, which comprises converting an N-hydroxyaniline of the formula VA as set forth in claim 2 using a phenyl carbonate of the formula VIA

L$^2$—CO$_2$—C$_6$H$_5$   VIA where L$^2$ is a halogen atom, into the corresponding N-hydroxycarbamate of the formula IB

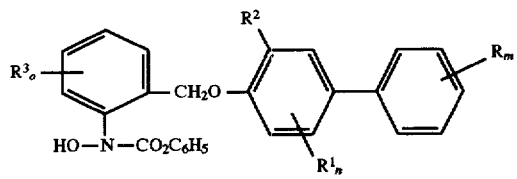

and then reacting IB with a compound VIII as set forth in claim 3 to give I.A.

7. A process for preparing the compound I as claimed in claim 1, which comprises reacting a compound of the formula XIV

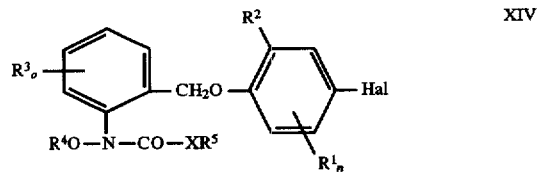

where Hal is a halogen atom, with an organometallic compound of the formula XV

where L-M is a metal-containing radical, in the presence of a palladium catalyst.

8. An intermediate of the formula XII

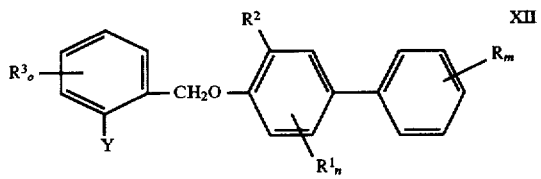

where Y is NO$_2$, NHOH, NHOR$^4$, N(OH)—CO$_2$C$_6$H$_5$ or N(OR$^4$)—CO$_2$C$_6$H$_5$ and the indices m, n and o and the substituents R, R$^1$, R$^2$, R$^3$ and R$^4$ have the meanings given in claim 1.

9. A composition suitable for controlling animal pests or harmful fungi, containing a solid or liquid carrier and a compound of the general formula I as claimed in claim 1.

10. The use of the compounds I as claimed in claim 1 for preparing a composition suitable for controlling animal pests or harmful fungi.

11. A method of controlling animal pests or harmful fungi, which comprises treating the pests or fungi to be controlled or the materials, plants, soil or seed to be protected from them with an effective amount of a compound of the general formula I as claimed in claim 1.

12. The 2-[4-biphenyloxymethylene]anilide of the formula I as set forth in claim 1, wherein R$_m$ is 2,4-dichloro;

n is 0;

R$^2$ is methyl;

o is 0;

R$^4$ and R$^5$ are methyl, and

X is oxygen.

* * * * *